(12) United States Patent
Xiong et al.

(10) Patent No.: US 12,380,963 B2
(45) Date of Patent: Aug. 5, 2025

(54) GENE EXPRESSION SIGNATURE OF HYPERPROGRESSIVE DISEASE (HPD) IN PATIENTS AFTER ANTI-PD-1 IMMUNOTHERAPY

(71) Applicant: The Medical College of Wisconsin, Inc., Milwaukee, WI (US)

(72) Inventors: Donghai Xiong, Franklin, WI (US); Ming You, Elm Grove, WI (US); Yian Wang, Milwaukee, WI (US)

(73) Assignee: The Medical College of Wisconsin, Inc., Milwaukee, WI (US)

( * ) Notice: Subject to any disclaimer, the term of this patent is extended or adjusted under 35 U.S.C. 154(b) by 689 days.

(21) Appl. No.: 17/070,668

(22) Filed: Oct. 14, 2020

(65) Prior Publication Data

US 2021/0110886 A1 Apr. 15, 2021

Related U.S. Application Data

(60) Provisional application No. 62/914,652, filed on Oct. 14, 2019.

(51) Int. Cl.
*G16B 20/20* (2019.01)
*C07K 16/28* (2006.01)
*C12Q 1/6886* (2018.01)
*G16B 5/20* (2019.01)
*G16B 25/00* (2019.01)
*G16H 50/20* (2018.01)

(52) U.S. Cl.
CPC .......... *G16B 20/20* (2019.02); *C07K 16/2818* (2013.01); *C12Q 1/6886* (2013.01); *G16B 5/20* (2019.02); *G16B 25/00* (2019.02); *G16H 50/20* (2018.01); *C12Q 2600/106* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,595,048 B2 | 9/2009 | Honjo | |
| 8,008,449 B2 | 8/2011 | Korman | |
| 8,217,149 B2 | 7/2012 | Irving | |
| 8,354,509 B2 | 1/2013 | Carven | |
| 8,728,474 B2 | 5/2014 | Honjo | |
| 8,735,553 B1 | 5/2014 | Li | |
| 8,779,105 B2 | 7/2014 | Korman | |
| 8,900,587 B2 | 12/2014 | Carven | |
| 8,952,136 B2 | 2/2015 | Carven | |
| 9,067,999 B1 | 6/2015 | Honjo | |
| 9,073,994 B2 | 7/2015 | Honjo | |

FOREIGN PATENT DOCUMENTS

| | | |
|---|---|---|
| EP | 2170959 B1 | 4/2010 |
| WO | 2011066389 A1 | 6/2011 |
| WO | 2017097407 A1 | 6/2017 |

OTHER PUBLICATIONS

Shen et al. (2021) Hyperprogressive Disease in Cancers Treated With Immune Checkpoint Inhibitors. Front. Pharmacol. 12:678409. doi: 10.3389/fphar.2021.678409.*
Ribas et al. What does PD-L1 positive or negative mean? J. Exp. Med. 2016 vol. 213 No. 13 2835-2840.*
Xiong et al. Immunogenomic Landscape Contributes to Hyperprogressive Disease after Anti-PD-1 Immunotherapy for Cancer, iScience 9, 258-277 Nov. 30, 2018 ª 2018 https://doi.org/10.1016/j.isci.2018.10.021.*
Ferrara et al. teaches that hyperprogressive disease (HPD) is frequent in non-small cell lung cancer (NSCLC) patients (pts) treated with anti PD1/PD-L1 monoclonal antibodies (IO) NSCLC, metastatic vol. 28 | Supplement 5 | Sep. 2017.*
Champiat et al Hyperprogressive disease: recognizing a novel pattern to improve patient management Nature Reviews | Clinial Oncology Reviews vol. 15 | Dec. 2018 |.*
Xiong et al. Immunogenomic Landscape Contributes to Hyperprogressive Disease after Anti-PD-1 Immunotherapy for Cancer, iScience 9, 258-277 Nov. 30, 2018 ª 2018 The Authors. https://doi.org/10.1016/j.isci.2018.10.021.*
Abdin, S.M., et al. (2018). Tackling Cancer Resistance by Immunotherapy: Updated Clinical Impact and Safety of PD-1/PD-L1 Inhibitors. Cancers (Basel) 10.
Aguirre-Gamboa, R., et al. (2013). SurvExpress: an online biomarker validation tool and database for cancer gene expression data using survival analysis. PLoS One 8, e74250.
Anders S, et al. HTSeq—a Python framework to work with high-throughput sequencing data. Bioinformatics. 2015;31(2):166-169.
Angelova, M., et al. (2015). Characterization of the immunophenotypes and antigenomes of colorectal cancers reveals distinct tumor escape mechanisms and novel targets for immunotherapy. Genome Biol. 16, 64.
Ascierto, M. L. et al. Transcriptional Mechanisms of Resistance to Anti-PD-1 Therapy. Clin Cancer Res 23, 3168-3180 (2017).
Benson, D.M., Jr., et al. (2010). The PD-1/PD-L1 axis modulates the natural killer cell versus multiple myeloma effect: a therapeutic target for CT-011, a novel monoclonal anti-PD-1 antibody. Blood 116, 2286-2294.
Biton, J., et al. (2018). TP53, STK11 and EGFR mutations predict tumor immune profile and the response to anti-PD-1 in lung adenocarcinoma. Clin. Cancer Res. 9, 1-14.
Bjorklund, A.K., et al. (2016). The heterogeneity of human CD127(+) innate lymphoid cells revealed by single-cell RNA sequencing. Nat. Immunol. 17, 451-460.
Budczies J, et al. cancerclass: An R Package for development and validation of diagnostic tests from high-dimensional molecular data. J Stat Software. 2014;59(1):1-19.

(Continued)

*Primary Examiner* — Joseph Woitach
(74) *Attorney, Agent, or Firm* — Quarles & Brady LLP

(57) ABSTRACT

A method of determining a patient's HPD status comprising the steps of a) examining a patient tumor sample for the expression level of HPD-diagnostic biomarkers, and b) determining whether the signature of the biomarkers is similar to that of a HPD positive signature is disclosed.

14 Claims, 56 Drawing Sheets
(53 of 56 Drawing Sheet(s) Filed in Color)

(56) References Cited

OTHER PUBLICATIONS

Cerami, E., et al. (2012). The cBio cancer genomics portal: an open platform for exploring multidimensional cancer genomics data. Cancer Discov. 2, 401-404.
Champiat, S., et al. (2017). Hyperprogressive disease is a new pattern of progression in cancer patients treated by anti-PD-1/PD-L1. Clin. Cancer Res. 23, 1920-1928.
Charoentong, P., et al. (2017). Pan-cancer Immunogenomic Analyses Reveal Genotype—Immunophenotype Relationships and Predictors of Response to Checkpoint Blockade. Cell Rep 18, 248-262.
Chaussabel, D. et al. "Assessing the human immune system through blood transcriptomics." BMC biology 8.1 (2010): 1-14.
Dang, H.X., et al. (2017). ClonEvol: clonal ordering and visualization in cancer sequencing. Ann Oncol 28, 3076-3082.
Ferrara, R., et al. (2018). Hyperprogressive Disease in Patients With Advanced Non-Small Cell Lung Cancer Treated With PD-1/PD-L1 Inhibitors or With Single-Agent Chemotherapy. JAMA Oncol. 1543-1552.
Ford, D.J. et al. (2015). The cancer COMPASS: navigating the functions of MLL complexes in cancer. Cancer Genet. 208, 178-191.
Fried, I., et al. (2018). Preliminary results of immune modulating antibody MDV9300 (pidilizumab) treatment in children with diffuse intrinsic pontine glioma. J Neurooncol 136, 189-195.
Friedman J, et al. Regularization Paths for Generalized Linear Models via Coordinate Descent. J Stat Softw. 2010;33(1):1-22.
Fung, K.Y., et al. (2017). The expanding role of innate lymphoid cells and their T-cell counterparts in gastrointestinal cancers. Mol. Immunol. 11, 1-9.
Galdiero, M.R., et al. (2013). Tumor associated macrophages and neutrophils in cancer. Immunobiology 218, 1402-1410.
Gao, J., et al. (2013). Integrative analysis of complex cancer genomics and clinical profiles using the cBioPortal. Sci. Signal. 6, pl1.
Goksuluk D, et al. MLSeq: Machine learning interface for RNA-sequencing data. Comput Methods Programs Biomed. 2019;175:223-231.
Goncharova, E., et al. (2004). TSC2 modulates actin cytoskeleton and focal adhesion through TSC1-binding domain and the Rac1 GTPase. J. Cell Biol. 167, 1171-1182.
Goncharova, E.A., et al. (2006). Modulation of cell migration and invasiveness by tumor suppressor TSC2 in lymphangioleiomyomatosis. Am. J. Respir. Cell Mol. Biol. 34, 473-480.
Gong, J., et al. (2017). Response to PD-1 blockade in microsatellite stable metastatic colorectal cancer harboring a POLE mutation. J. Natl. Compr. Canc Netw. 15, 142-147.
Gossage, L., et al. (2015). VHL, the story of a tumour suppressor gene. Nat. Rev. Cancer 15, 55-64.
Gu, Z., et al. (2016). Complex heatmaps reveal patterns and correlations in multidimensional genomic data. Bioinformatics 32, 2847-2849.
Haas, B.J., et al. (2013). De novo transcript sequence reconstruction from RNA-seq using the Trinity platform for reference generation and analysis. Nat Protoc 8, 1494-1512.
Hakimi, A.A., et al. (2016). An Integrated Metabolic Atlas of Clear Cell Renal Cell Carcinoma. Cancer Cell 29, 104-116.
Hanley, J.A., et al. (1982). The meaning and use of the area under a receiver operating characteristic (ROC) curve. Radiology 143, 29-36.
Hanna, G.J., et al. (2018). Frameshift events predict anti-PD-1/L1 response in head and neck cancer. JCI Insight 3, 1-13.
Hanzelmann, S., Castelo, R., and Guinney, J. (2013). GSVA: gene set variation analysis for microarray and RNA-seq data. BMC Bioinformatics 14, 7.
Hepworth, M.R., et al. (2015). Immune tolerance. Group 3 innate lymphoid cells mediate intestinal selection of commensal bacteria-specific CD4(+) T cells. Science 348, 1031-1035.
Hugo, W. et al. Genomic and Transcriptomic Features of Response to Anti-PD-1 Therapy in Metastatic Melanoma. Cell 165, 35-44 (2016).
Irshad, S., et al. (2017). RORgammat(+) innate lymphoid cells promote lymph node metastasis of breast cancers. Cancer Res. 77, 1083-1096.
Jelinek, T., et al. (2016). PD-1/PD-L1 inhibitors in multiple myeloma: The present and the future. Oncoimmunology 5, e1254856.
Kammerer-Jacquet, S.F., et al. (2017). Independent association of PD-L1 expression with noninactivated VHL clear cell renal cell carcinoma—A finding with therapeutic potential. Int. J. Cancer 140, 142-148.
Kato S, et al. Hyperprogressors after Immunotherapy: Analysis of Genomic Alterations Associated with Accelerated Growth Rate. Clin Cancer Res. 2017;23(15):4242-50.
Kirchberger, S., et al. (2013). Innate lymphoid cells sustain colon cancer through production of interleukin-22 in a mouse model. J. Exp. Med. 210, 917-931.
Koboldt, D.C., et al. (2012). VarScan 2: somatic mutation and copy number alteration discovery in cancer by exome sequencing. Genome Res 22, 568-576.
Koyama, S., et al. (2016). Adaptive resistance to therapeutic PD-1 blockade is associated with upregulation of alternative immune checkpoints. Nat. Commun. 7, 10501.
Langmead B, et al. Ultrafast and memory-efficient alignment of short DNA sequences to the human genome. Genome Biol. 2009;10(3):R25.
Lazar-Molnar, E., et al. (2010). Programmed death-1 (PD-1)-deficient mice are extraordinarily sensitive to tuberculosis. Proc. Natl. Acad. Sci. U S A 107, 13402-13407.
Lee, J., et al. (2009). A tumor suppressive coactivator complex of p53 containing ASC-2 and histone H3-lysine-4 methyltransferase MLL3 or its paralogue MLL4. Proc. Natl. Acad. Sci. U S A 106, 8513-8518.
Levin, J. Z., et al. "Comprehensive comparative analysis of strand-specific RNA sequencing methods." Nature methods 7.9 (2010): 709-715.
Li, H., et al. (2009). Fast and accurate short read alignment with Burrows-Wheeler transform. Bioinformatics 25, 1754-1760.
Liberzon, A., et al. (2011). Molecular signatures database (MSigDB) 3.0. Bioinformatics 27, 1739-1740.
Liberzon, A., et al. (2015). The Molecular Signatures Database (MSigDB) hallmark gene set collection. Cell Syst 1, 417-425.
Love MI, et al. Moderated estimation of fold change and dispersion for RNA-seq data with DESeq2. Genome Biol. 2014;15(12):550.
Mariathasan, S., et al. (2018). TGFbeta attenuates tumour response to PD-L1 blockade by contributing to exclusion of T cells. Nature 554, 544-548.
Mckenna, A., et al. (2010). The Genome Analysis Toolkit: a MapReduce framework for analyzing next-generation DNA sequencing data. Genome Res 20, 1297-1303.
Menon, S., et al. (2014). Spatial control of the TSC complex integrates insulin and nutrient regulation of mTORC1 at the lysosome. Cell 156, 771-785.
Miao, D., et al. (2018). Genomic correlates of response to immune checkpoint therapies in clear cell renal cell carcinoma. Science 359, 801-806. 276 iScience 9, 258-277, Nov. 30, 2018.
Miller, C.A., et al. (2014). SciClone: inferring clonal architecture and tracking the spatial and temporal patterns of tumor evolution. PLoS Comput Biol 10, e1003665.
Miller, C.A., et al. (2016). Visualizing tumor evolution with the fishplot package for R. BMC Genomics 17, 880.
Mishalian, I., et al. (2013). Tumor-associated neutrophils (TAN) develop protumorigenic properties during tumor progression. Cancer Immunol. Immunother. 62, 1745-1756.
Mkrtichyan, M., et al. (2011). Anti-PD-1 synergizes with cyclophosphamide to induce potent anti-tumor vaccine effects through novel mechanisms. Eur J Immunol 41, 2977-2986.
Niknafs, N., et al. (2013). MuPIT interactive: webserver for mapping variant positions to annotated, interactive 3D structures. Hum Genet 132, 1235-1243.
Olsson, A., et al. (2016). Single-cell analysis of mixed-lineage states leading to a binary cell fate choice. Nature 537, 698-702.

(56) References Cited

OTHER PUBLICATIONS

Pei, M., et al. (2016). Identification and expression analysis of genes related to calyx persistence in Korla fragrant pear. BMC Genomics 17, 132.
Rabello, D.D.A., et al. (2018). MLL2/KMT2D and MLL3/KMT2C expression correlates with disease progression and response to imatinib mesylate in chronic myeloid leukemia. Cancer Cell Int. 18, 26.
Riaz, N., et al. (2017). Tumor and Microenvironment Evolution during Immunotherapy with Nivolumab. Cell 171, 934-949 e915.
Rizvi, N.A., et al. (2015). Mutational landscape determines sensitivity to PD-1 blockade in non-small cell lung cancer. Science 348, 124-128.
Robinson MD, et al. A scaling normalization method for differential expression analysis of RNA-seq data. Genome Biol. 2010;11(3):R25.
Rosenblatt, J., et al. (2011). PD-1 blockade by CT-011, anti-PD-1 antibody, enhances ex vivo T-cell responses to autologous dendritic cell/myeloma fusion vaccine. J Immunother 34, 409-418.
Saada-Bouzid, E., et al. (2017). Hyperprogression during anti-PD-1/PD-L1 therapy in patients with recurrent and/or metastatic head and neck squamous cell carcinoma. Ann Oncol 28, 1605-1611.
Sagiv, J.Y., et al. (2015). Phenotypic diversity and plasticity in circulating neutrophil subpopulations in cancer. Cell Rep. 10, 562-573.
Sharma, P., et al. (2015). Immune checkpoint targeting in cancer therapy: toward combination strategies with curative potential. Cell 161, 205-214.
Sharma, P., et al. (2017). Primary, adaptive, and acquired resistance to cancer immunotherapy. Cell 168, 707-723.
Spits, H., et al. (2013). Innate lymphoid cells—a proposal for uniform nomenclature. Nat. Rev. Immunol. 13, 145-149.
Subramanian, A., et al. (2005). Gene set enrichment analysis: a knowledge-based approach for interpreting genome-wide expression profiles. Proc Natl Acad Sci U S A 102, 15545-15550.
Tappeiner, E., et al. (2017). TIminer: NGS data mining pipeline for cancer immunology and immunotherapy. Bioinformatics 33, 3140-3141.
Tauriello, D.V.F., et al. (2018). TGFbeta drives immune evasion in genetically reconstituted colon cancer metastasis. Nature 554, 538-543.
Teo, M.Y., et al. (2018). Alterations in DNA damage response and repair genes as potential marker of clinical benefit from PD-1/PD-L1 blockade in advanced urothelial cancers. J. Clin. Oncol. 36, 1685-1694.
Tibshirani R, et al. Strong rules for discarding predictors in lasso-type problems. Journal of the Royal Statistical Society: Series B (Statistical Methodology). 2012;74(2):245-66.
Topalian, S.L., et al. (2012). Targeting the PD-1/B7-H1(PD-L1) pathway to activate anti-tumor immunity. Curr. Opin. Immunol. 24, 207-212.
Tuting, T., et al. (2016). Cancer. How neutrophils promote metastasis. Science 352, 145-146.
Van Beek, J.J.P., et al. (2016). Innate lymphoid cells in tumor immunity. Biomedicines 4, 7-21.
Wallrapp, A., et al. (2017). The neuropeptide NMU amplifies ILC2-driven allergic lung inflammation. Nature 549, 351-356.
Wang, K., et al. (2010). Annovar: functional annotation of genetic variants from high-throughput sequencing data. Nucleic Acids Res 38, e164.
Wang, X., et al. (2015). The developmental transcriptome of the synanthropic fly Chrysomya megacephala and insights into olfactory proteins. BMC Genomics 16, 20.
Wartewig, T., et al. (2017). PD-1 is a haploinsufficient suppressor of T cell lymphomagenesis. Nature 552, 121-125.
Westin, J.R., et al. (2014). Safety and activity of PD1 blockade by pidilizumab in combination with rituximab in patients with relapsed follicular lymphoma: a single group, open-label, phase 2 trial. Lancet Oncol 15, 69-77.
Xiong, D. et al. Immunogenomic Landscape Contributes to Hyperprogressive Disease after Anti-PD-1 Immunotherapy for Cancer. iScience 9, 258-277 (Nov. 30, 2018).
Xiong, D., et al. (2015). A recurrent mutation in PARK2 is associated with familial lung cancer. Am J Hum Genet 96, 301-308.
Yoshikawa, S., et al. (2017). Multi-omics profiling of patients with melanoma treated with Nivolumab in project HOPE. Anticancer Res. 37, 1321-1328.
Zaretsky, J.M., et al. (2016). Mutations associated with acquired resistance to PD-1 blockade in melanoma. N. Engl. J. Med. 375, 819-829.
Zhang, J., et al. (2017). CD13(hi) Neutrophil-like myeloid-derived suppressor cells exert immune suppression through Arginase 1 expression in pancreatic ductal adenocarcinoma. Oncoimmunology 6, e1258504.
Zoncu, R., et al. (2011). mTOR: from growth signal integration to cancer, diabetes and ageing. Nat. Rev. Mol. Cell Biol. 12, 21-35.

* cited by examiner

A. ILC1 population

B. ILC2 population

GENE EXPRESSION SIGNATURE OF HYPERPROGRESSIVE DISEASE (HPD) IN PATIENTS AFTER ANTI-PD-1 IMMUNOTHERAPY

CROSS-REFERENCE TO RELATED APPLICATIONS

This application claims priority to U.S. Provisional Application No. 62/914,652 filed on Oct. 14, 2019, the contents of which are incorporated by reference in its entirety.

STATEMENT REGARDING FEDERALLY SPONSORED RESEARCH

This invention was made with government support under NIH grant R01CA223804 and N01CN120015, awarded by the National Institutes of Health. The government has certain rights to the invention.

BACKGROUND

Immune checkpoint therapies including those targeting PD-1, or its primary ligand PD-L1, have demonstrated therapeutic responses across a broad range of cancer types (Sharma and Allison, 2015). Anti-PD-1 therapy blocks the interaction of PD-1, an inhibitory receptor on tumor-infiltrating T cells, with its ligands PD-L1 and PD-L2 that are predominantly expressed on tumor cells and antigen-presenting cells (APCs), respectively (Topalian et al., 2012). Despite the success of anti-PD-1 immunotherapy in approximately 20%-30% of patients with cancer, the majority of patients do not respond to this treatment (Sharma et al., 2017). In addition, increasing clinical evidence suggests that a significant subset of nonresponsive patients may experience acceleration of disease progression after treatment with anti-PD-1, a phenomenon known as hyperprogressive disease (HPD). Although accurate identification of the frequency of patients developing HPD has been limited by variability in diagnostic criteria, conservative estimates suggest that HPD may occur in as many as 10% of patients treated with anti-PD-1 (Champiat et al., 2017, Kato et al., 2017, Saada-Bouzid et al., 2017).

In contrast to identifying factors that predict responsiveness to PD-1-blocking therapies such as tumor expression of PD-L1, high tumor mutational burden, and the presence of tumor-infiltrating CD8+ T cells, little is known about the mechanisms underlying HPD. Although a pilot study suggested that some patients with MDM2 family amplification or EGFR aberrations developed HPD after treatment with PD-1 or PD-L1 inhibitors (Kato et al., 2017), it is likely that alterations beyond those identified in that study are important in facilitating accelerated disease progression.

SUMMARY OF THE INVENTION

As described in the Examples, the present invention comprehensively examine the mechanisms of HPD by performing whole-exome sequencing (WES) and RNA sequencing (RNA-seq) analyses of formalin-fixed paraffin-embedded (FFPE) samples of tumors before and after anti-PD-1 therapy in patients with clinical evidence of HPD. The inventors identified individual somatic mutations and mutation clusters associated with clonal evolution that may contribute to the accelerated tumor growth observed in HPD. The inventors also identified characteristic decreases in HPD tumor immunogenicity. The inventors also identified a gene signature that may be predictive of HPD development. These changes were HPD patient specific, and were not found in the tumors of anti-PD-1-treated patients without HPD phenotypes from previous studies. The present invention identified the genomics and immune features associated with HPD tumors after anti-PD-1 immunotherapy.

In one embodiment, the disclosure provides a method for processing a test sample to determine a likelihood that a patient develops hyperprogesssive disease (HPD) in response to anti-PD-1 immunotherapy in a patient, comprising: (a) receiving information indicative of an expression level of a plurality of biomarkers in a tumor sample extracted from the patient; (b) providing the plurality of biomarker levels as input to a classifier configured to predict likelihood that a patient develops hyperprogesssive disease in response to anti-PD-1 immunotherapy in a computer to classify the test sample, wherein the classifier was trained with a plurality of training samples comprising pre-therapy tumor expression data of known HPD patients and pre-therapy tumor expression data of known non-HPD patients; (c) receiving, from the classifier, an output report that identifies said classification as indicative of the likelihood that the patient develops hyperprogesssive disease in response to anti-PD-1 immunotherapy. In some embodiments, the method further comprises providing a treatment to said subject.

In another aspect, the kit for detecting the likelihood of a subject for developing HPD, the kit comprising a panel of 121-biomarker from Table 4 attached to a solid surface and an instructions for use.

In a further aspect, the disclosure provides a system for processing a test sample to determine a likelihood that a patient develops hyperprogesssive disease (HPD) in response to anti-PD-1 immunotherapy in a patient, comprising: (a) a computer capable of receiving input data of the expression of a plurality of biomarker levels, (b) a classifier configured to predict likelihood that a patient develops hyperprogesssive disease in response to anti-PD-1 immunotherapy to classify the test sample, and (c) an output report from the classifier that identifies said classification as indicative of the likelihood that the patient develops hyperprogesssive disease in response to anti-PD-1 immunotherapy.

In another aspect, the disclosure provides a kit for the diagnosis of a HPD positive tumor, wherein the kit comprises probes useful to detect the level of at least 10, 20, 30, 40, 50, 60, 70, 80, 90, 100, or 110 of the biomarkers listed in Table 4.

In yet another aspect, the disclosure provides a gene chip useful for the diagnosis of a HPD positive tumor, wherein the chip comprises probes useful to detect the level of at least 10, 20, 30, 40, 50, 60, 70, 80, 90, 100, or 110 of the biomarkers listed in Table 4.

Another aspect of the present disclosure provides all that is described and illustrated herein.

BRIEF DESCRIPTION OF DRAWINGS

The present document contains at least one drawing executed in color. Copies of this patent or patent application publication with color drawings will be provided by the Office upon request and payment of the necessary fee.

(B) Performances of the 121-gene set classifier and subset genes from the 121-gene in TCGA BRCA (Breast invasive carcinoma) dataset. Black line represents that all genes in genome are used as variables in prediction model. Red line represents that 121-gene set classifier is used as variables in prediction model. Green line represents that cancer type specific subset genes (given in Table 7) from the 121-gene are used as variables in prediction model. Blue and turquoise lines represent that different portions of cancer type specific subset genes are used as variables in prediction model.

Figure 27:
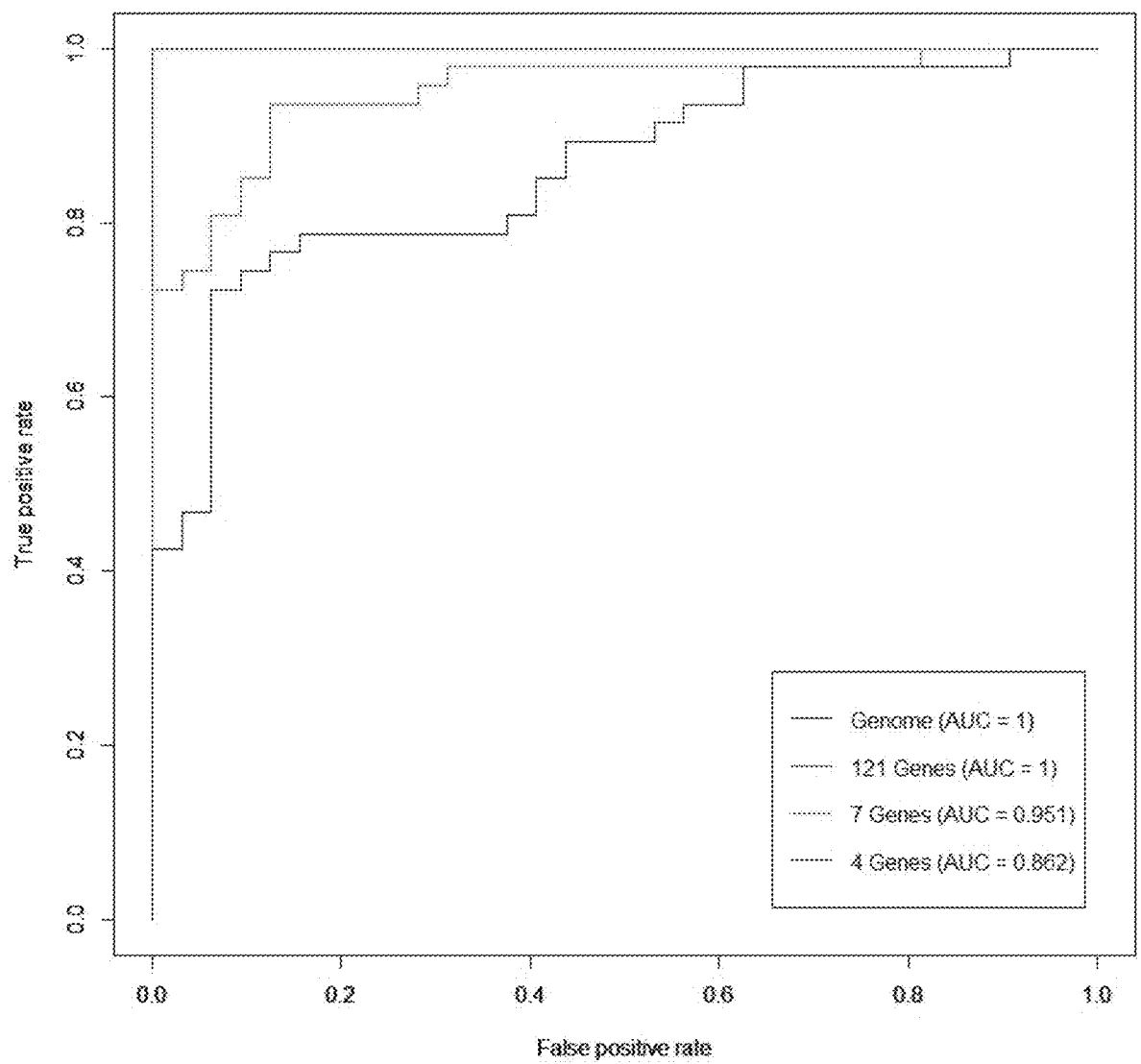

FIG. 27 Performances of the 121-gene set classifier and subset genes from the 121-gene in TCGA COAD (Colon adenocarcinoma) dataset. Black line represents that all genes in genome are used as variables in prediction model. Red line represents that 121-gene set classifier is used as variables in prediction model. Green line represents that cancer type specific subset genes (given in Table7) from the 121-gene are used as variables in prediction model. Blue and turquoise lines represent that different portions of cancer type specific subset genes are used as variables in prediction model.

Figure 28:
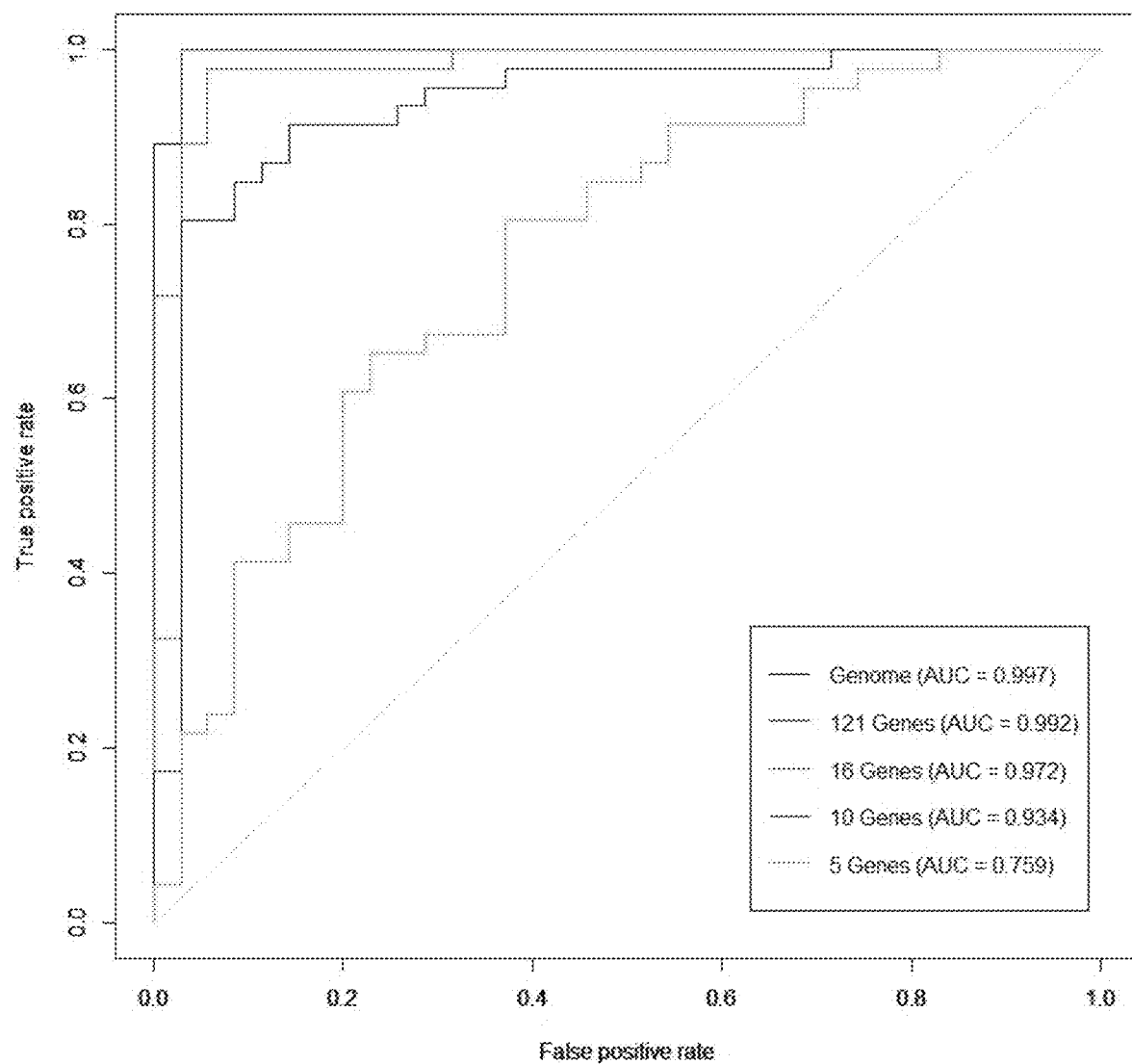

FIG. 28: Performances of the 121-gene set classifier and subset genes from the 121-gene in TCGA ESCA (Esophageal carcinoma) dataset. Black line represents that all genes in genome are used as variables in prediction model. Red line represents that 121-gene set classifier is used as variables in prediction model. Green line represents that cancer type specific subset genes (given in Table7) from the 121-gene are used as variables in prediction model. Blue and turquoise lines represent that different portions of cancer type specific subset genes are used as variables in prediction model.

Figure 29:
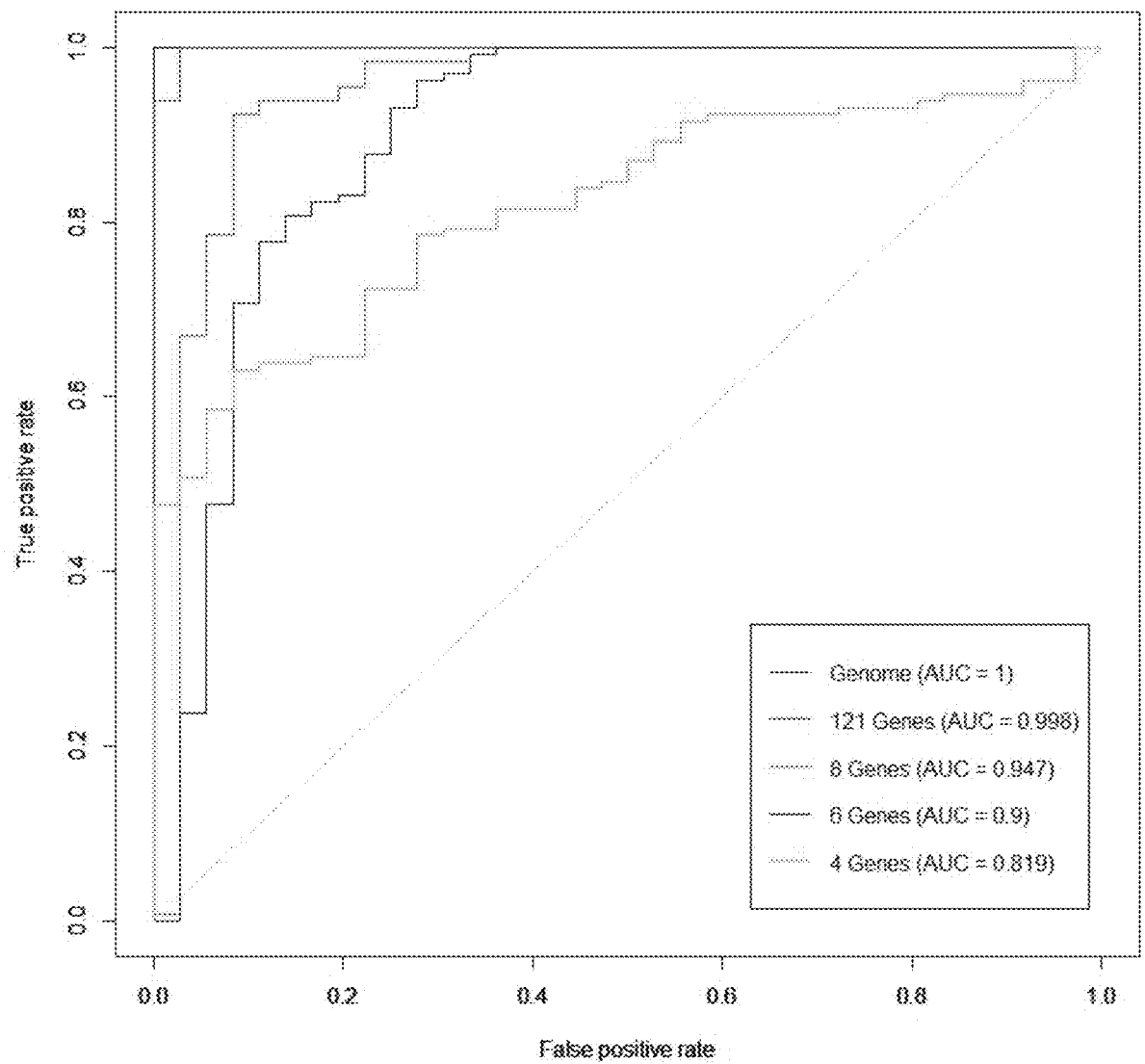

FIG. 29: Performances of the 121-gene set classifier and subset genes from the 121-gene in TCGA HNSC (Head and Neck squamous cell carcinoma) dataset. Black line represents that all genes in genome are used as variables in prediction model. Red line represents that 121-gene set classifier is used as variables in prediction model. Green line represents that cancer type specific subset genes (given in Table 7) from the 121-gene are used as variables in prediction model. Blue and turquoise lines represent that different portions of cancer type specific subset genes are used as variables in prediction model.

Figure 30:
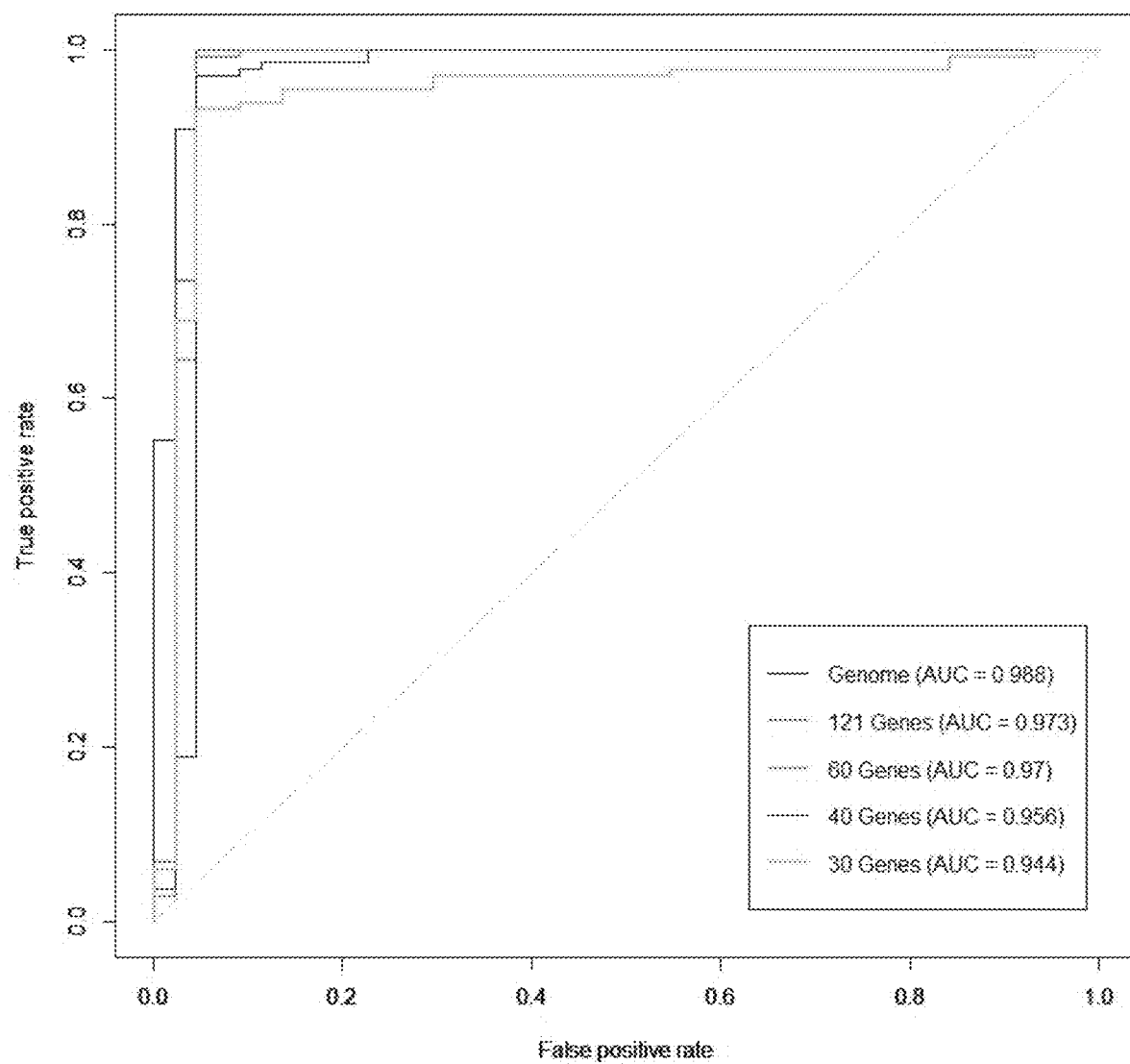

FIG. 30 Performances of the 121-gene set classifier and subset genes from the 121-gene in TCGA KIRC (Kidney renal clear cell carcinoma) dataset. Black line represents that all genes in genome are used as variables in prediction model. Red line represents that 121-gene set classifier is used as variables in prediction model. Green line represents that cancer type specific subset genes (given in Table 7) from the 121-gene are used as variables in prediction model. Blue and turquoise lines represent that different portions of cancer type specific subset genes are used as variables in prediction model.

Figure 31:
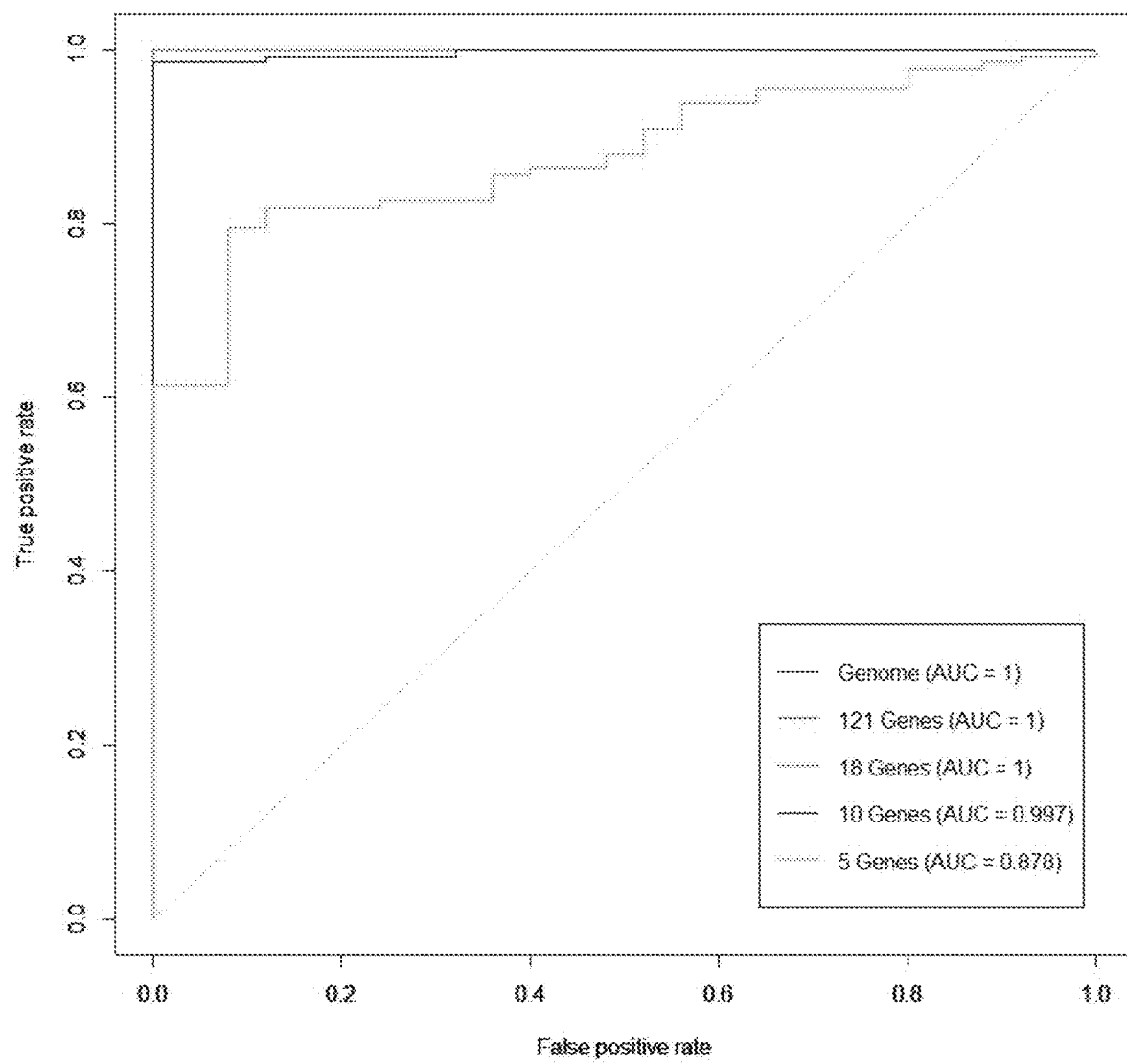

FIG. 31: Performances of the 121-gene set classifier and subset genes from the 121-gene in TCGA LGG (Brain Lower Grade Glioma) dataset. Black line represents that all genes in genome are used as variables in prediction model. Red line represents that 121-gene set classifier is used as variables in prediction model. Green line represents that cancer type specific subset genes (given in Table 7) from the 121-gene are used as variables in prediction model. Blue and turquoise lines represent that different portions of cancer type specific subset genes are used as variables in prediction model.

Figure 32:
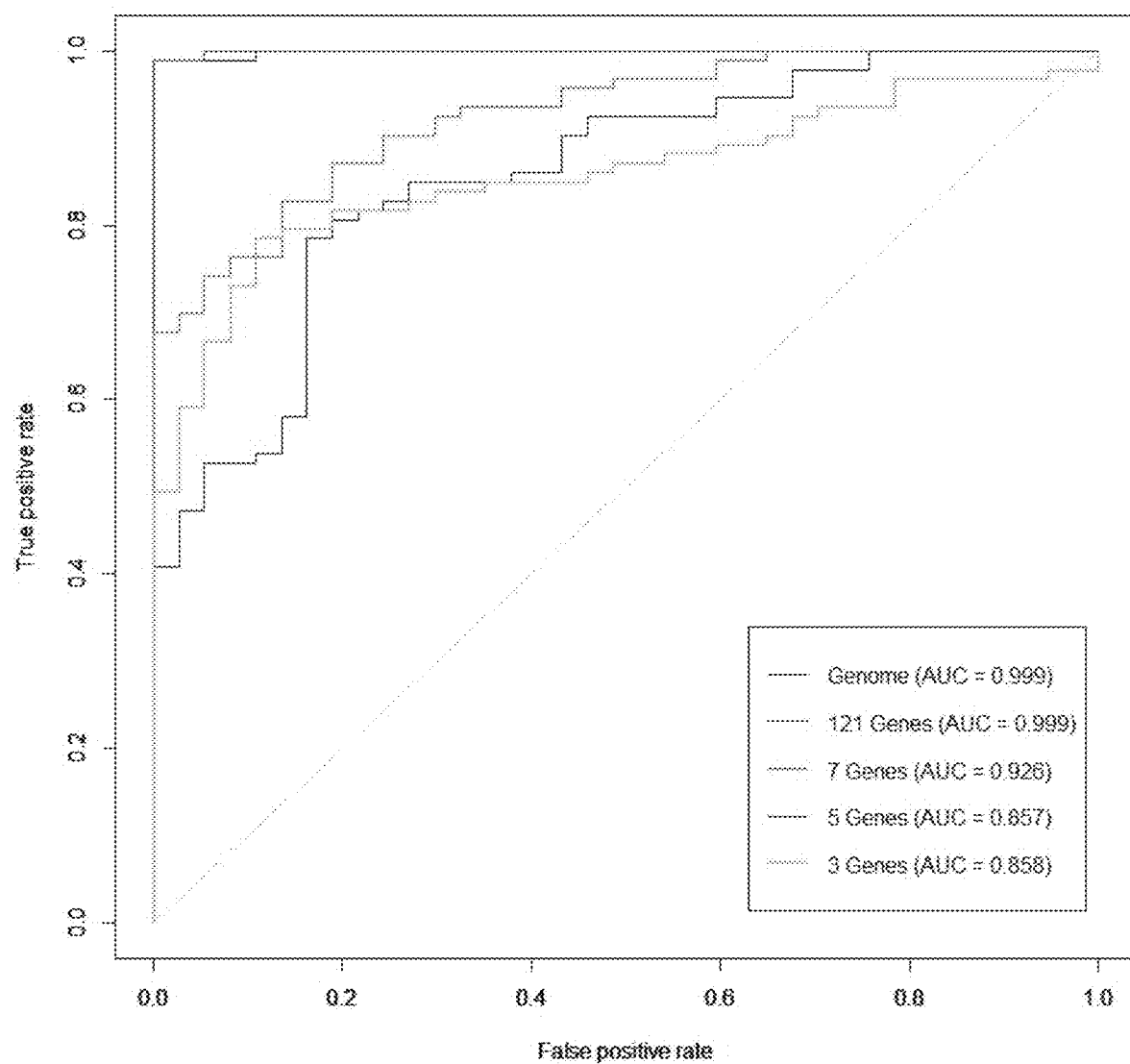

FIG. 32: Performances of the 121-gene set classifier and subset genes from the 121-gene in TCGA LIHC (Liver hepatocellular carcinoma) dataset. Black line represents that all genes in genome are used as variables in prediction model. Red line represents that 121-gene set classifier is used as variables in prediction model. Green line represents that cancer type specific subset genes (given in Table 7) from the 121-gene are used as variables in prediction model. Blue and turquoise lines represent that different portions of cancer type specific subset genes are used as variables in prediction model.

Figure 33:
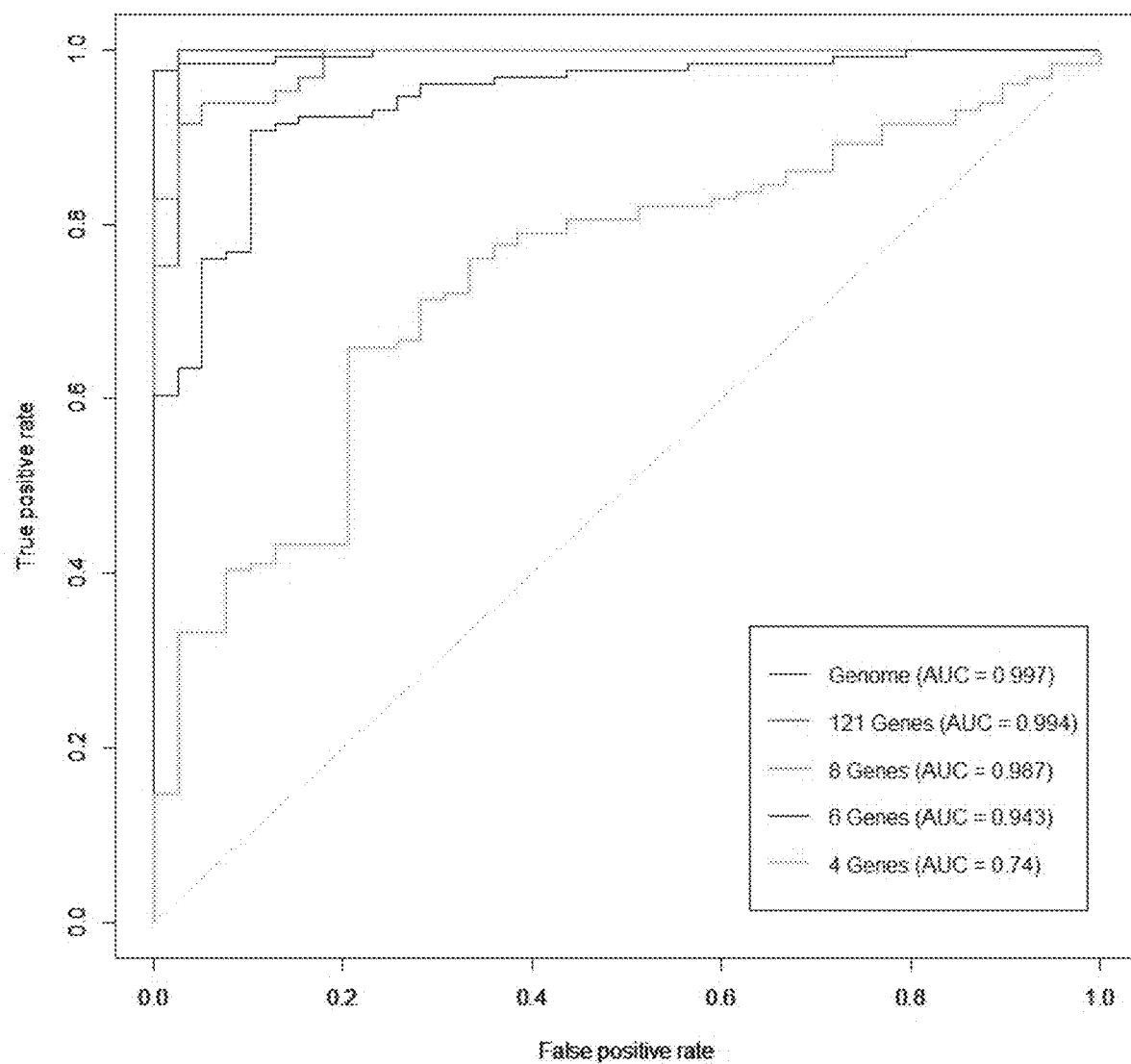

FIG. 33: Performances of the 121-gene set classifier and subset genes from the 121-gene in TCGA LUAD (Lung adenocarcinoma) dataset. Black line represents that all genes in genome are used as variables in prediction model. Red line represents that 121-gene set classifier is used as variables in prediction model. Green line represents that cancer type specific subset genes (given in Table 7) from the 121-gene are used as variables in prediction model. Blue and turquoise lines represent that different portions of cancer type specific subset genes are used as variables in prediction model.

Figure 34:
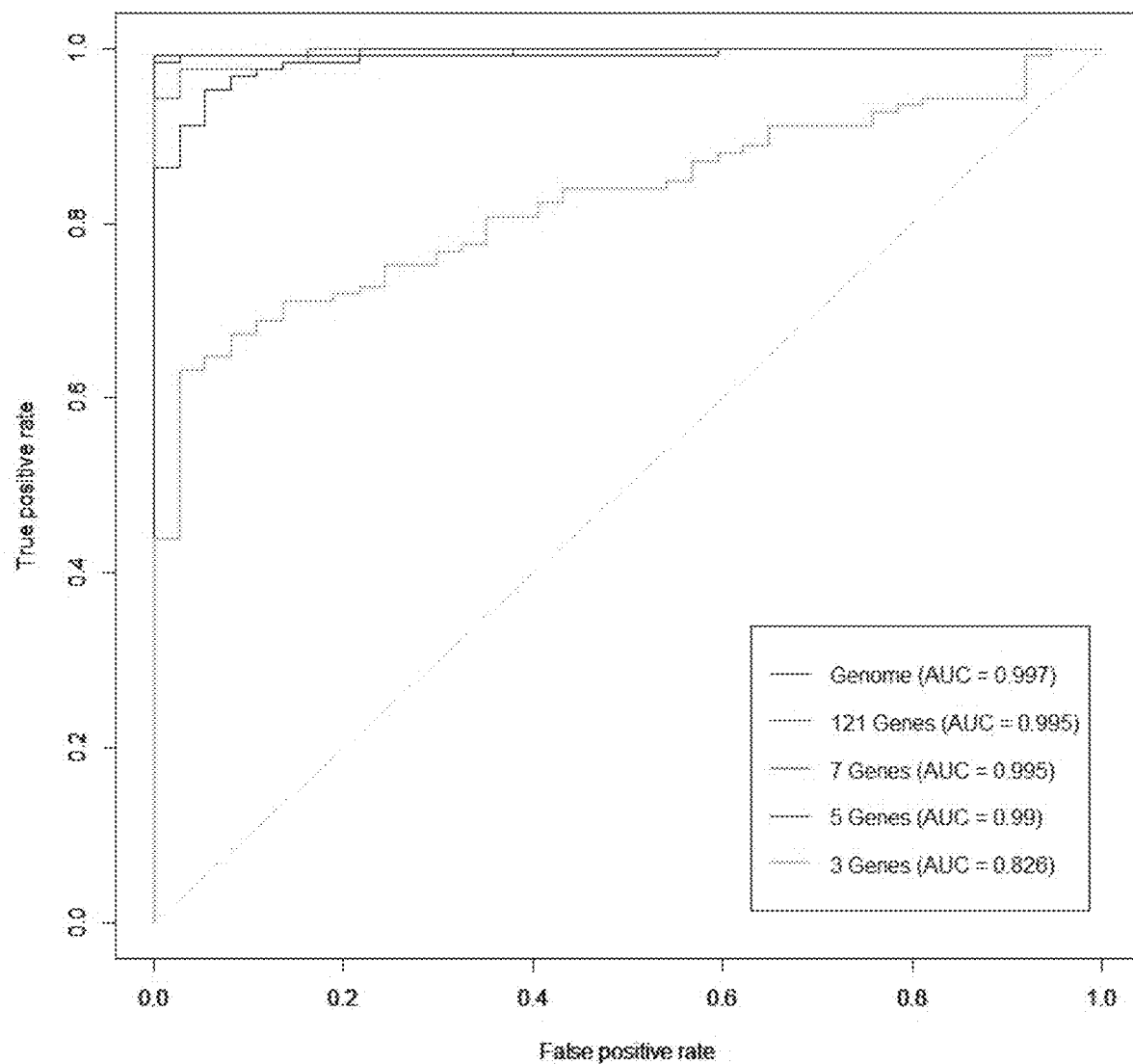

FIG. 34 Performances of the 121-gene set classifier and subset genes from the 121-gene in TCGA LUSC (Lung squamous cell carcinoma) dataset. Black line represents that all genes in genome are used as variables in prediction model. Red line represents that 121-gene set classifier is used as variables in prediction model. Green line represents that cancer type specific subset genes (given in Table 7) from the 121-gene are used as variables in prediction model. Blue and turquoise lines represent that different portions of cancer type specific subset genes are used as variables in prediction model.

Figure 35:
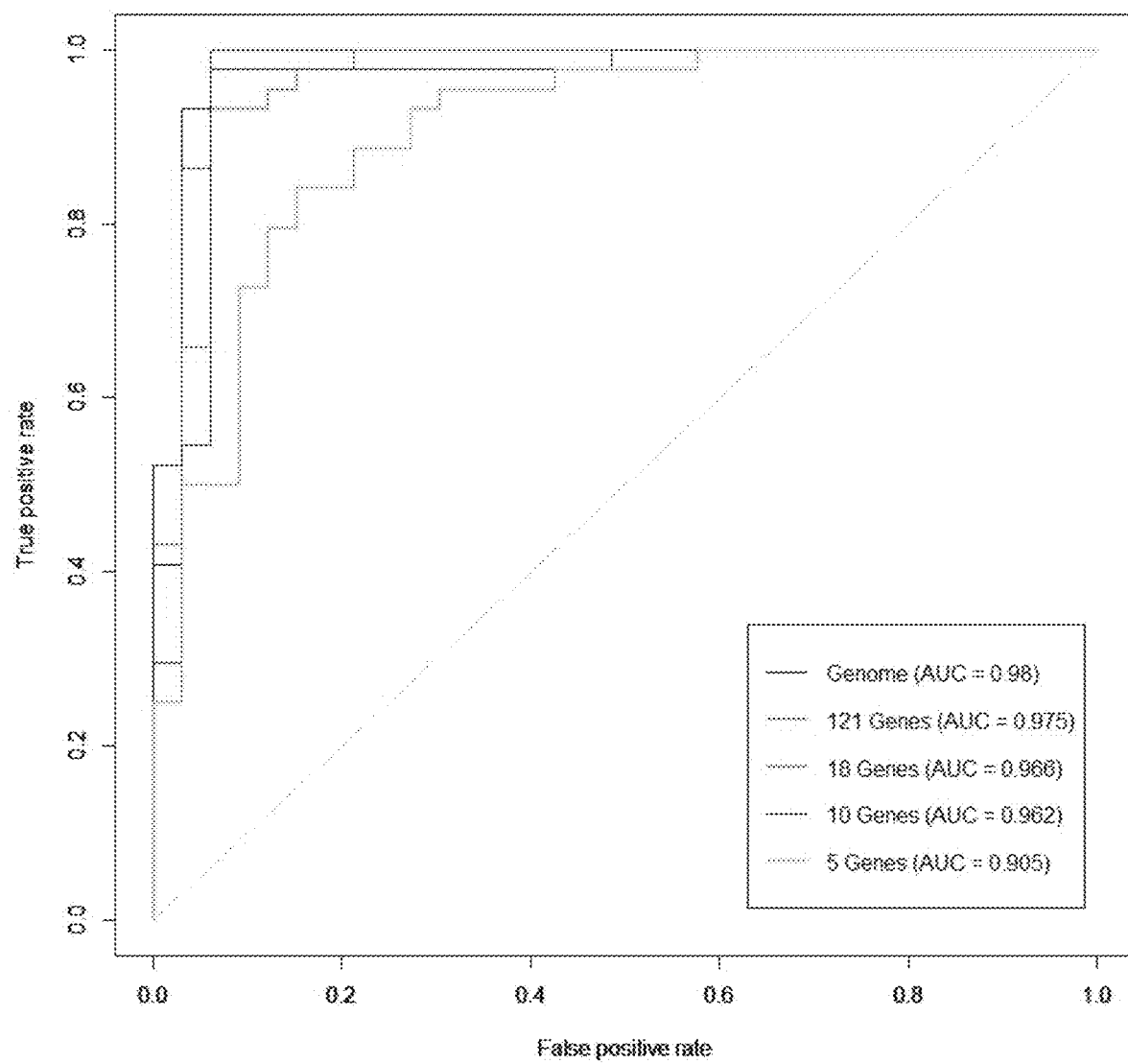

FIG. 35 Performances of the 121-gene set classifier and subset genes from the 121-gene in TCGA PAAD (Pancreatic adenocarcinoma) dataset. Black line represents that all genes in genome are used as variables in prediction model. Red line represents that 121-gene set classifier is used as variables in prediction model. Green line represents that cancer type specific subset genes (given in Table 7) from the 121-gene are used as variables in prediction model. Blue and turquoise lines represent that different portions of cancer type specific subset genes are used as variables in prediction model.

Figure 36:
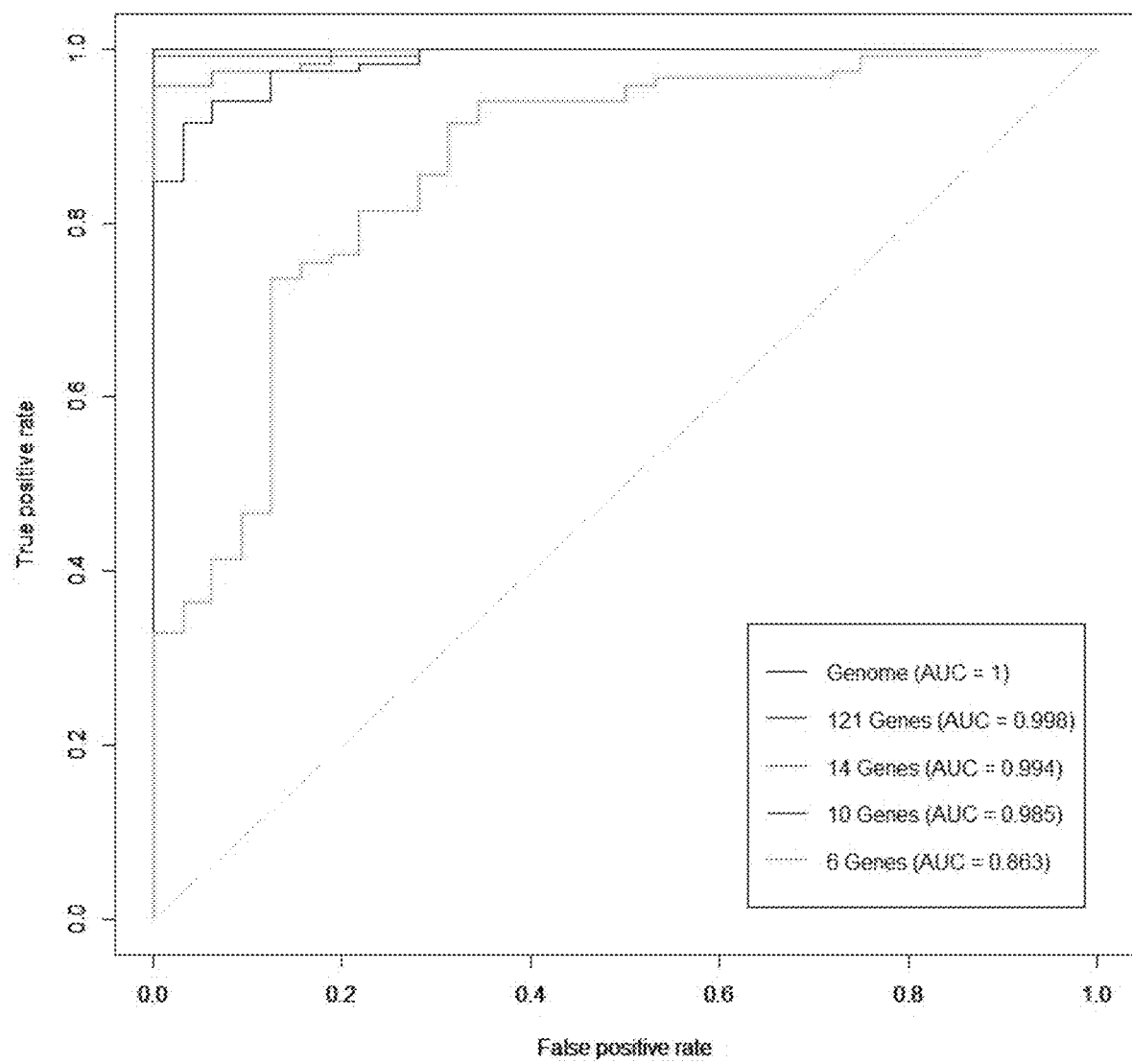

FIG. 36: Performances of the 121-gene set classifier and subset genes from the 121-gene in TCGA SKCM (Skin cutaneous melanoma) dataset. Black line represents that all genes in genome are used as variables in prediction model. Red line represents that 121-gene set classifier is used as variables in prediction model. Green line represents that cancer type specific subset genes (given in Table7) from the 121-gene are used as variables in prediction model. Blue and turquoise lines represent that different portions of cancer type specific subset genes are used as variables in prediction model.

Figure 37:
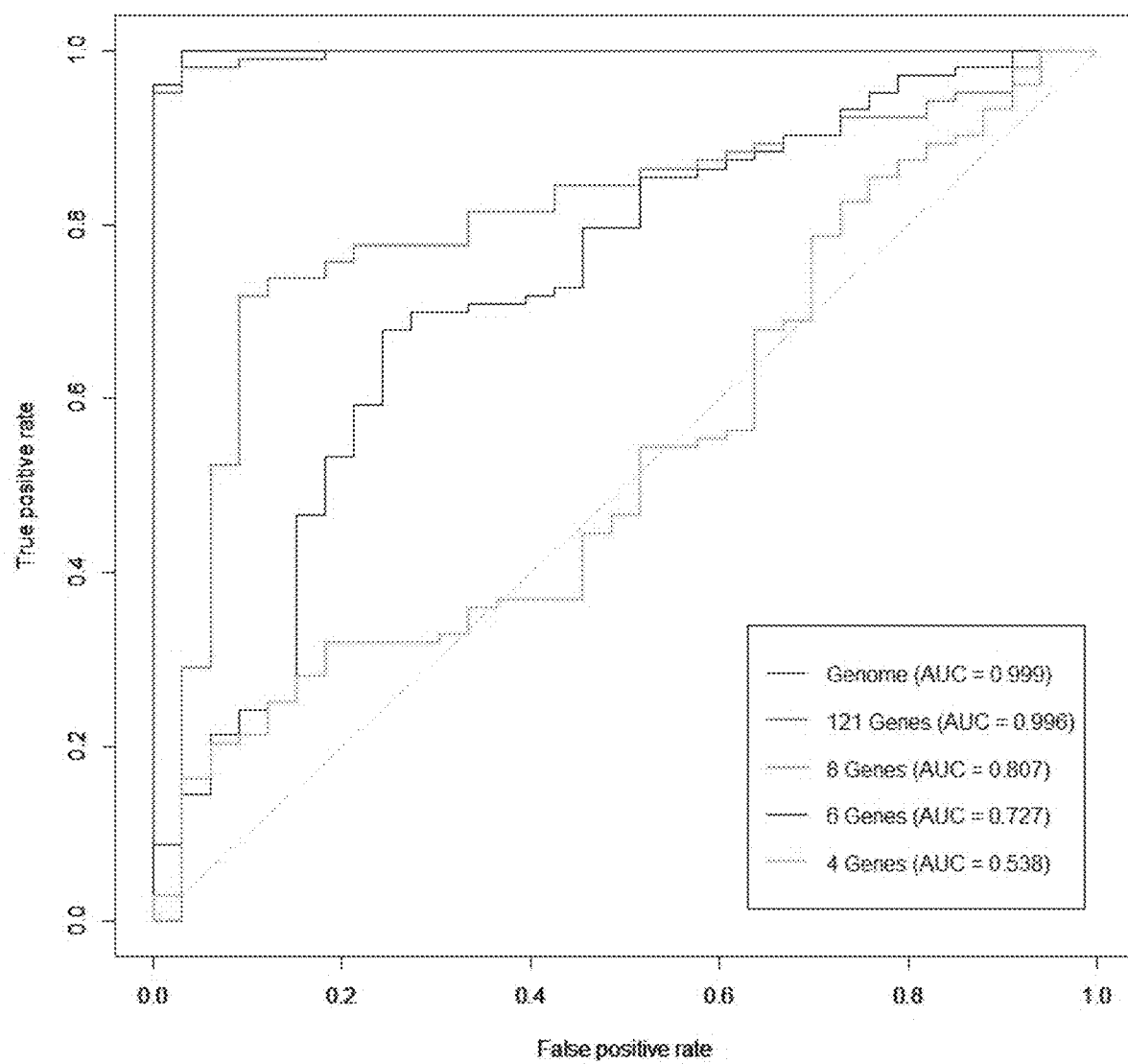

FIG. 37 Performances of the 121-gene set classifier and subset genes from the 121-gene in TCGA STAD (Stomach adenocarcinoma) dataset. Black line represents that all genes in genome are used as variables in prediction model. Red line represents that 121-gene set classifier is used as variables in prediction model. Green line represents that cancer type specific subset genes (given in Table 7) from the 121-gene are used as variables in prediction model. Blue and turquoise lines represent that different portions of cancer type specific subset genes are used as variables in prediction model.

Figure 38:
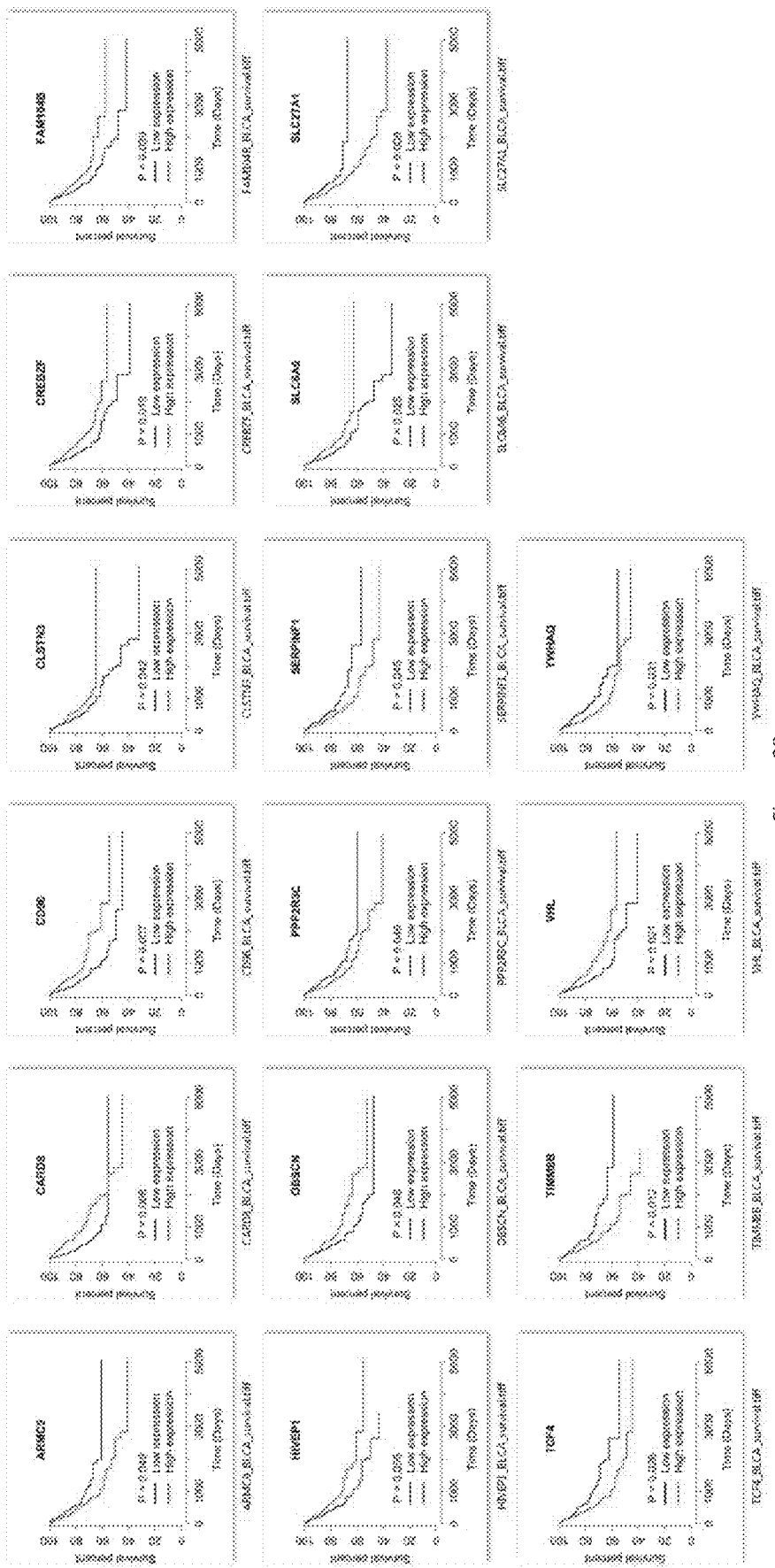

FIG. 38: Subset genes from the 121-gene anti-PD-1 HPD signature individually associated with TCGA BLCA (Bladder carcinoma) overall survival outcome.

Figure 39:
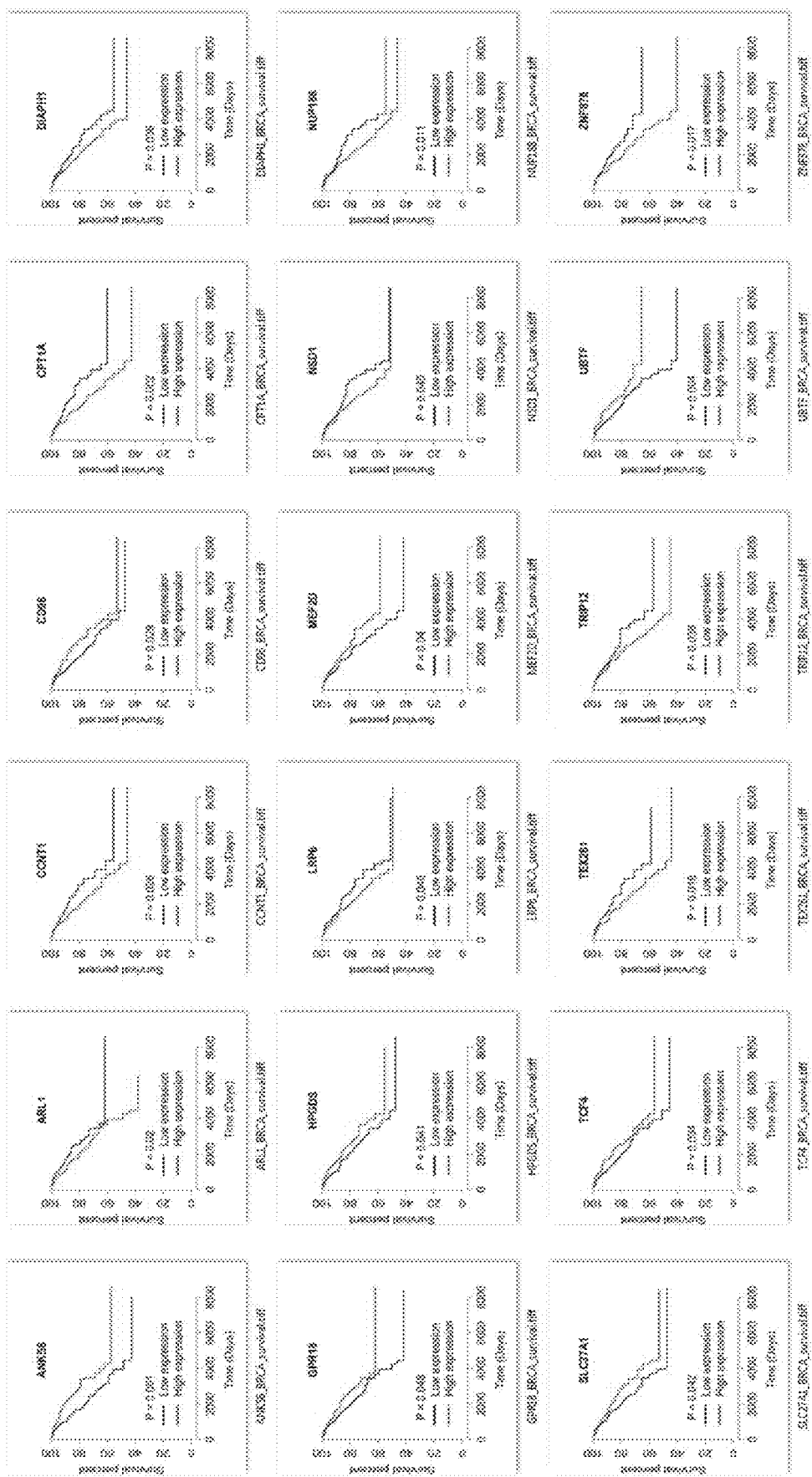

FIG. 39: Subset genes from the 121-gene anti-PD-1 HPD signature individually associated with TCGA BRCA (Breast invasive carcinoma) overall survival.

Figure 40:
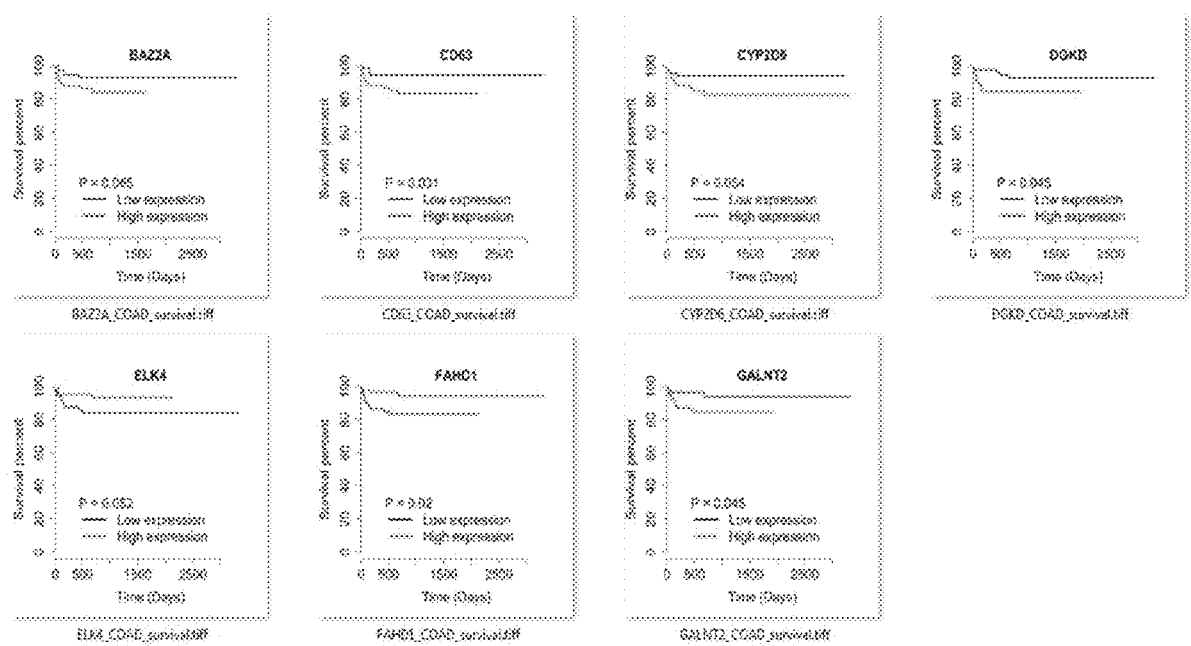

FIG. 40: Subset genes from the 121-gene anti-PD-1 HPD signature individually associated with TCGA COAD (Colon adenocarcinoma) overall survival.

Figure 41:
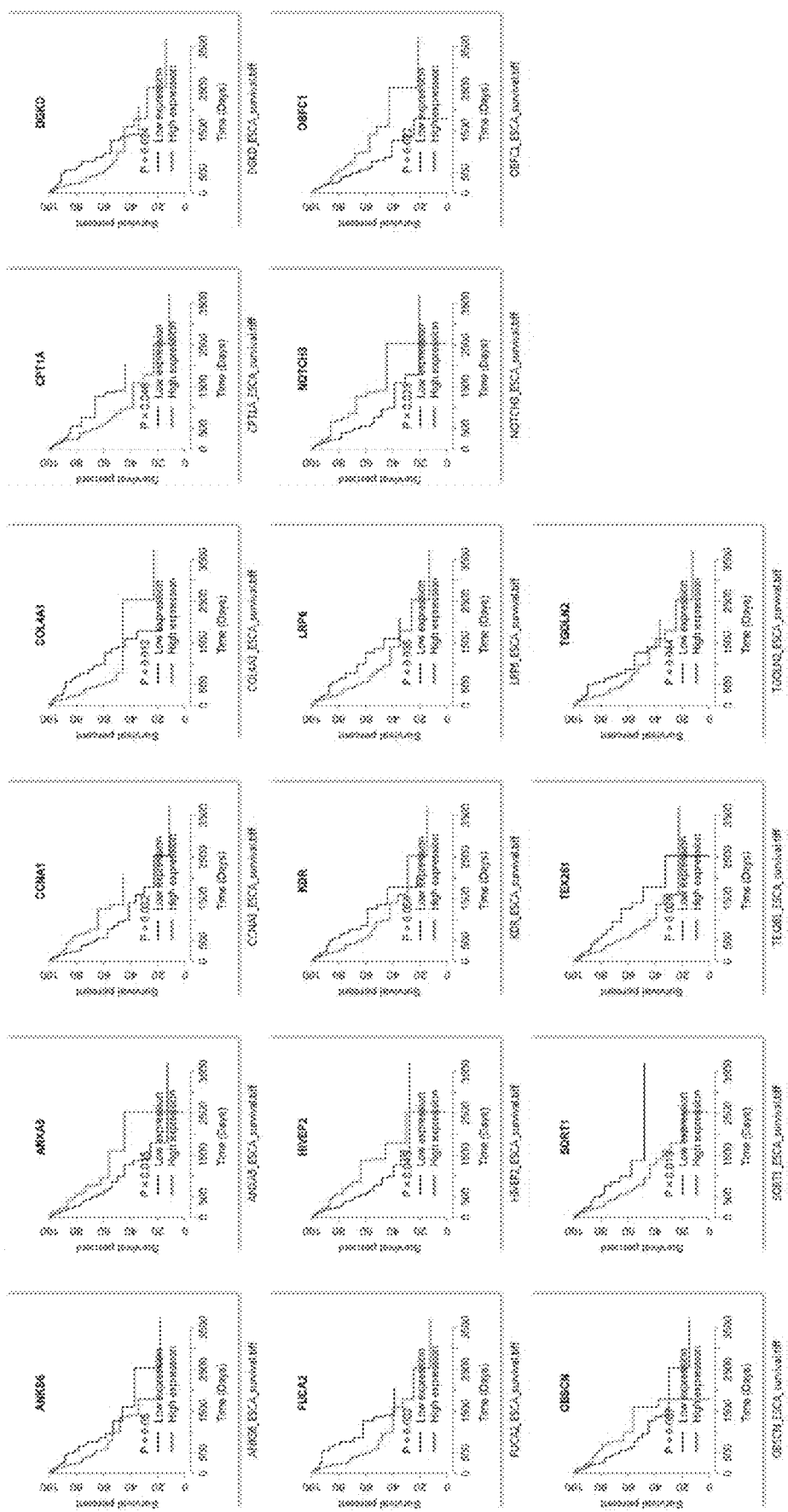

FIG. 41: Subset genes from the 121-gene anti-PD-1 HPD signature individually associated with TCGA ESCA (Esophageal carcinoma) overall survival.

Figure 42:
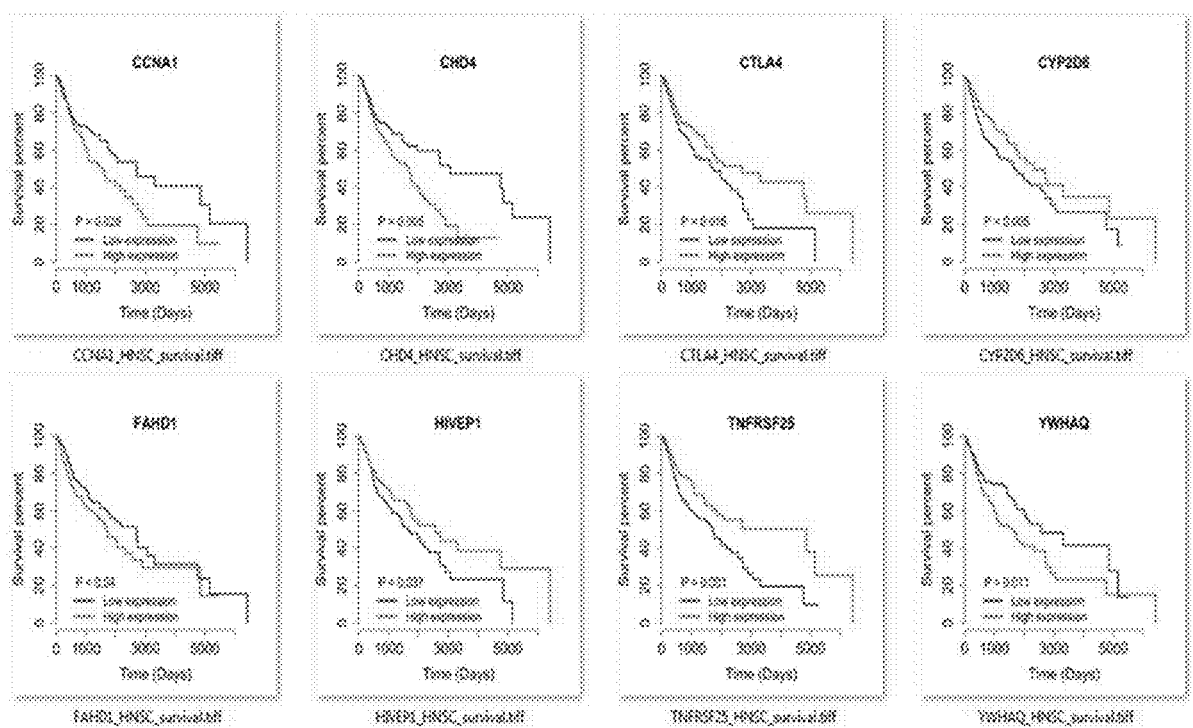

FIG. 42: Subset genes from the 121-gene anti-PD-1 HPD signature individually associated with TCGA HNSC (Head and Neck squamous cell carcinoma) overall survival.

Figure 43:
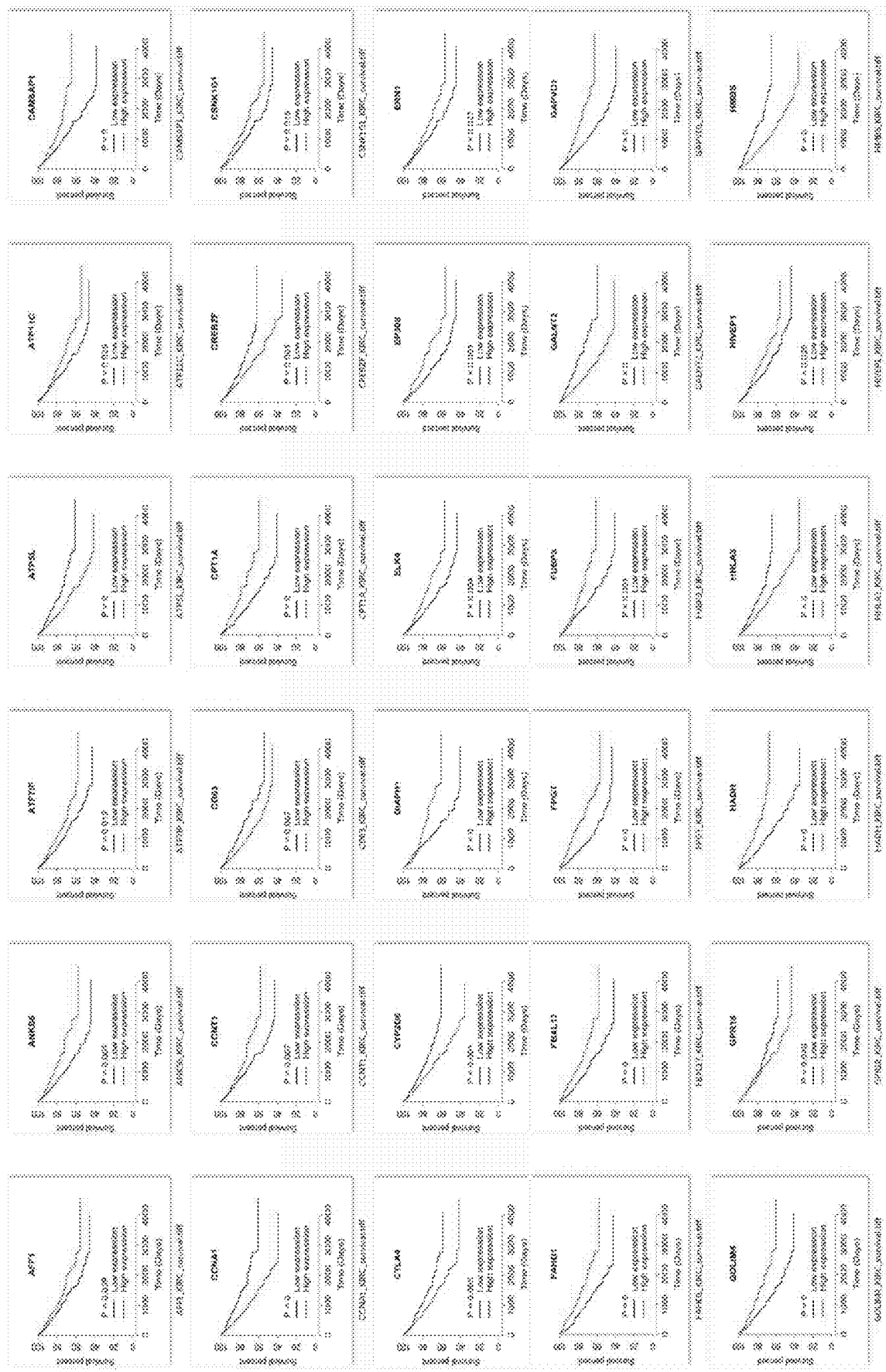
Figure 43:
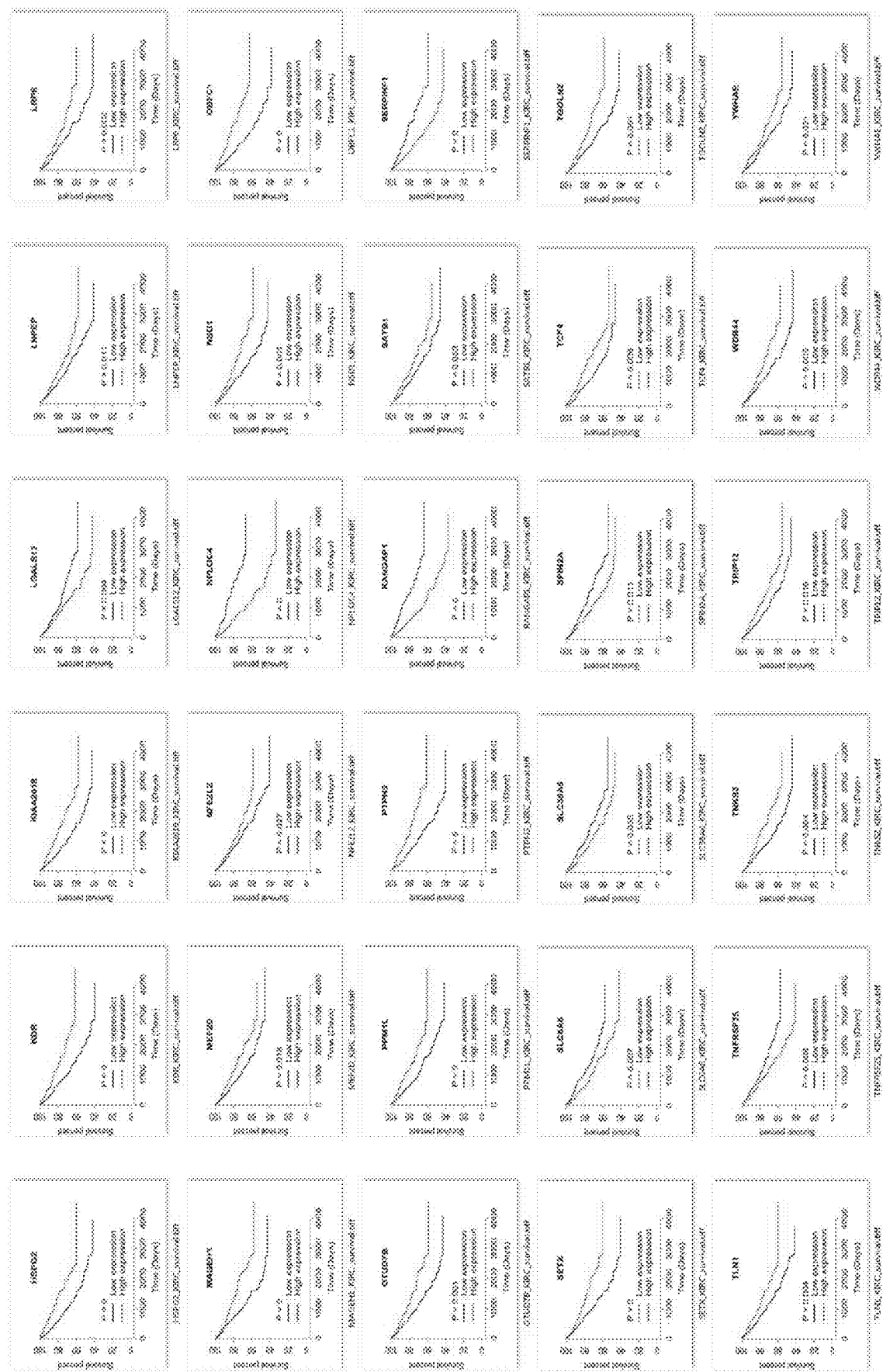

FIG. 43: Subset genes from the 121-gene HPD signature individually associated with TCGA KIRC (Kidney renal clear cell carcinoma) overall survival.

Figure 44:
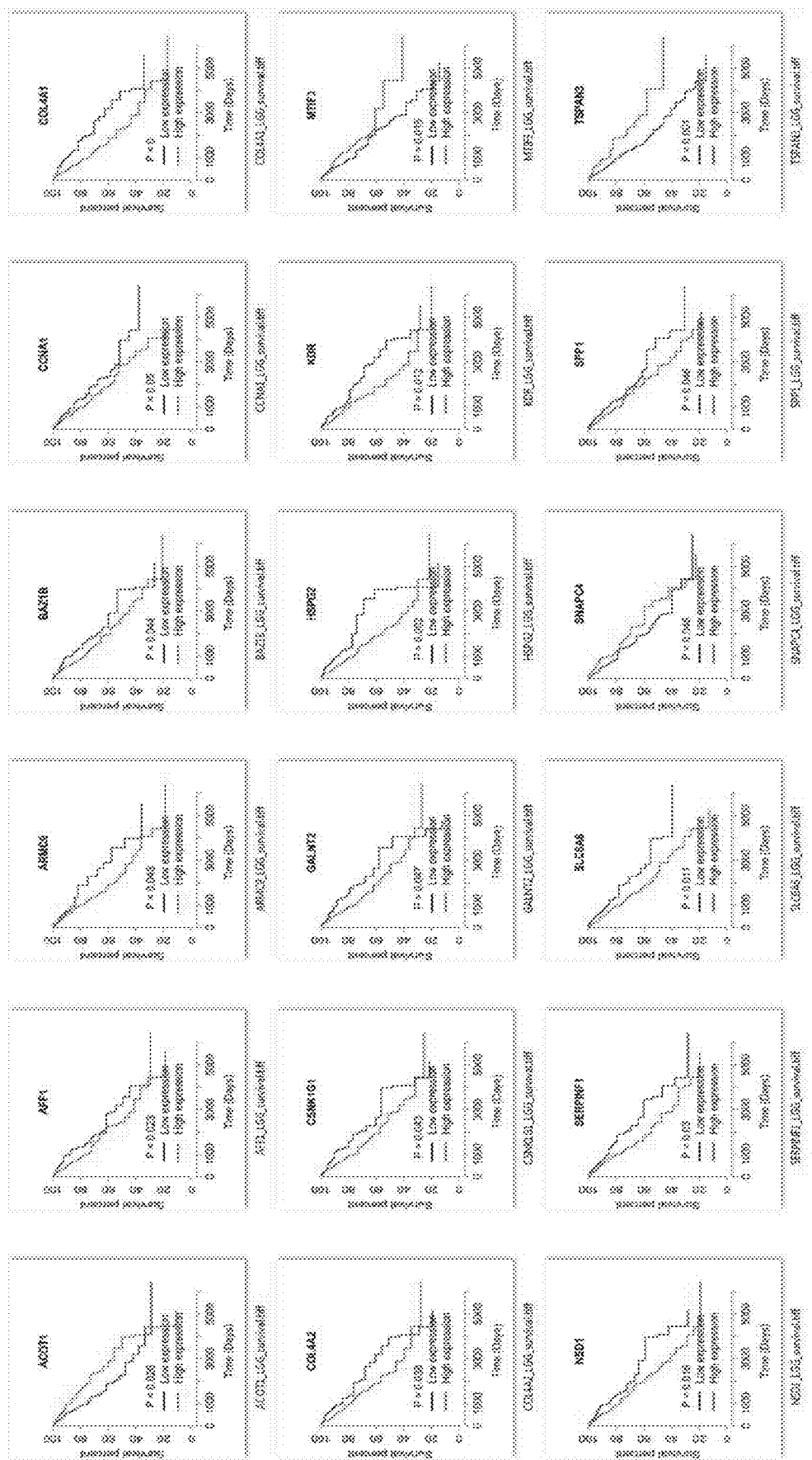

FIG. 44: Subset genes from the 121-gene HPD signature individually associated with TCGA LGG (Brain Lower Grade Glioma) overall survival.

Figure 45:
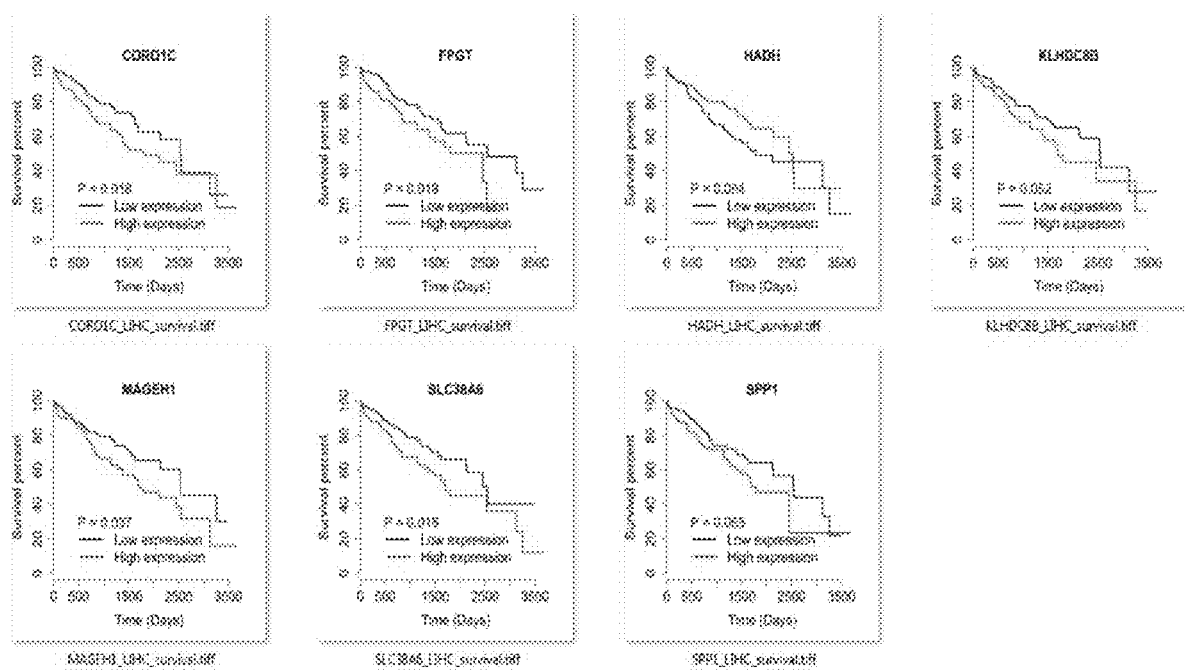

FIG. 45: Subset genes from the 121-gene HPD signature individually associated with TCGA LIHC (Liver hepatocellular carcinoma) overall survival.

Figure 46:
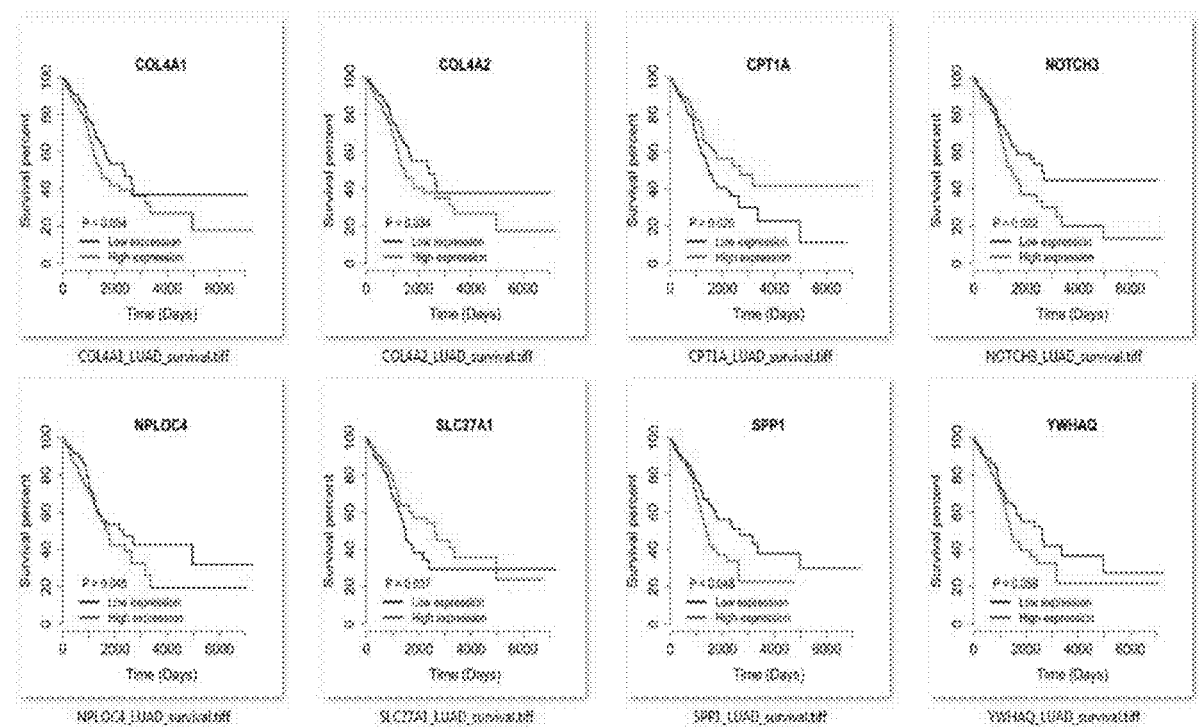

FIG. 46: Subset genes from the 121-gene HPD signature individually associated with TCGA LUAD (Lung adenocarcinoma) overall survival.

Figure 47:
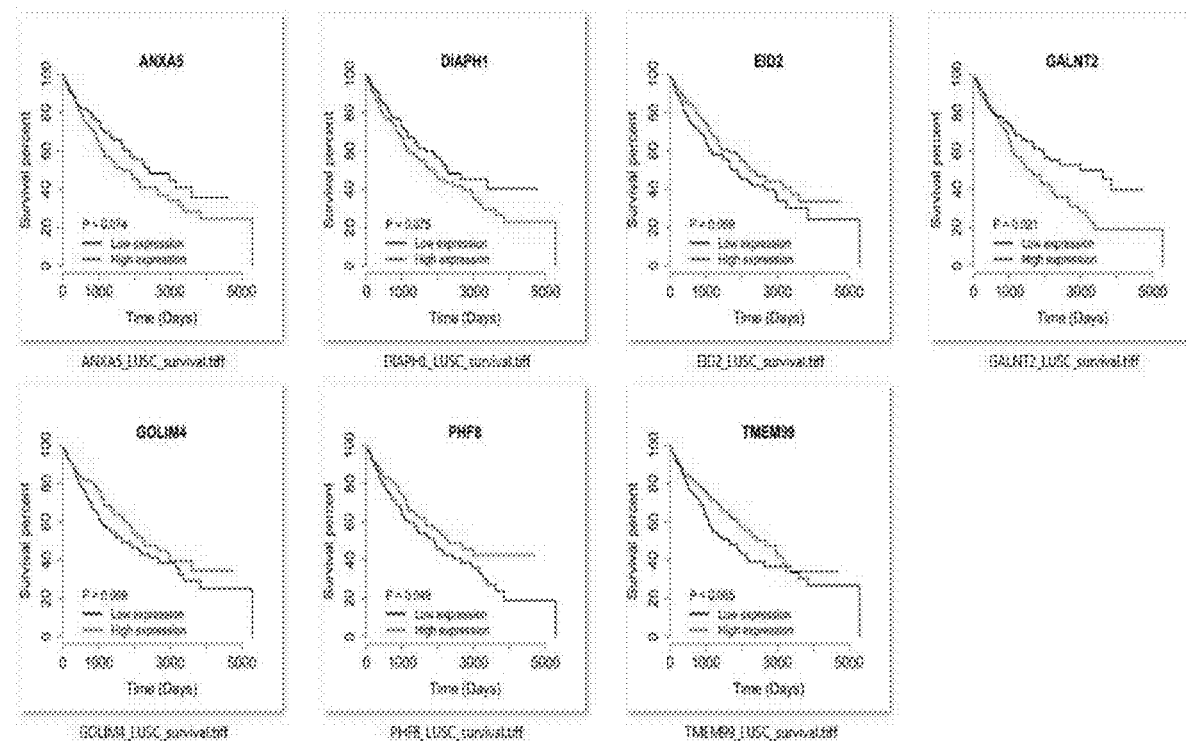

FIG. 47: Subset genes from the 121-gene HPD signature individually associated with TCGA LUSC (Lung squamous cell carcinoma) overall survival.

Figure 48:
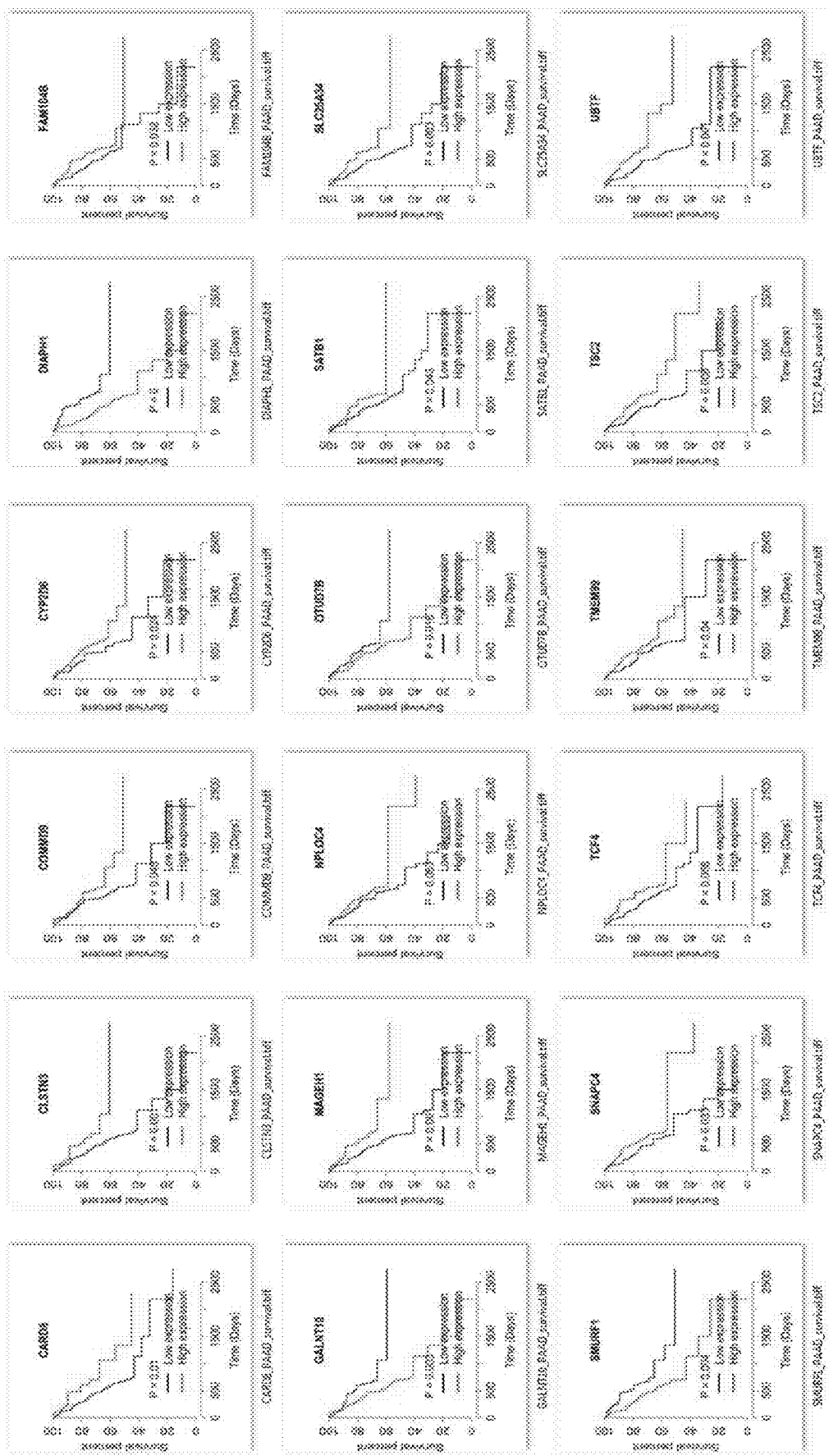

FIG. 48: Subset genes from the 121-gene HPD signature individually associated with TCGA PAAD (Pancreatic adenocarcinoma) overall survival.

Figure 49:
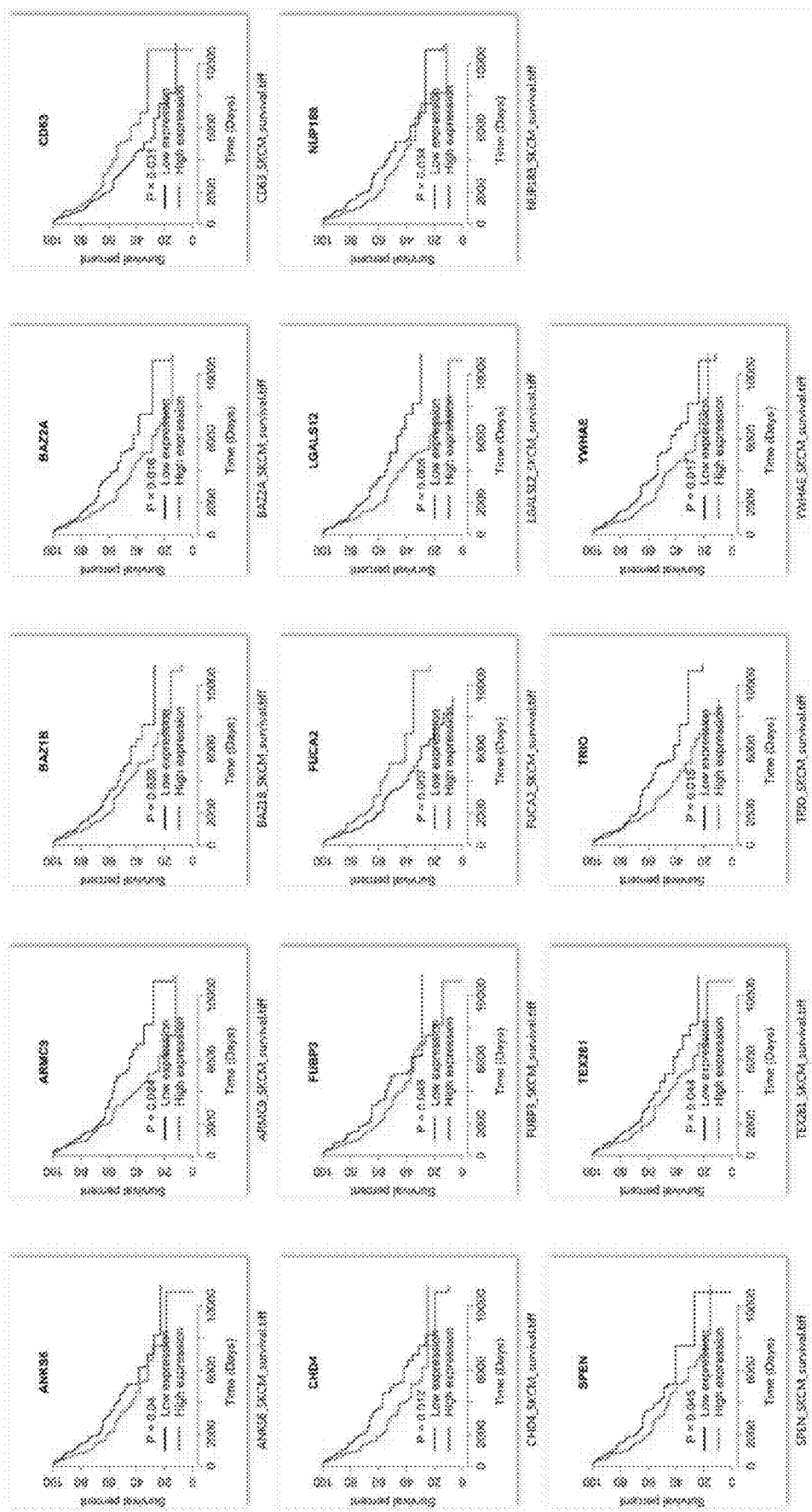

FIG. 49: Subset genes from the 121-gene HPD signature individually associated with TCGA SKCM (Skin cutaneous melanoma) overall survival.

Figure 50:
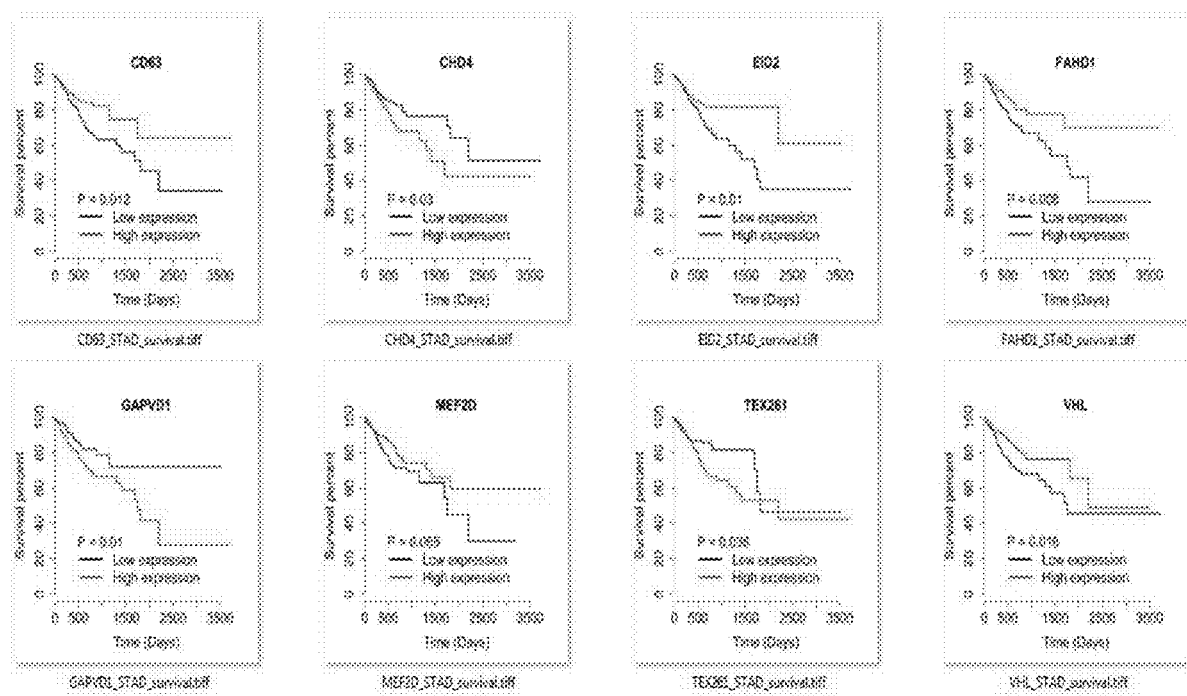

FIG. 50: Subset genes from the 121-gene HPD signature individually associated with TCGA STAD (Stomach adenocarcinoma) overall survival.

Figure 51:
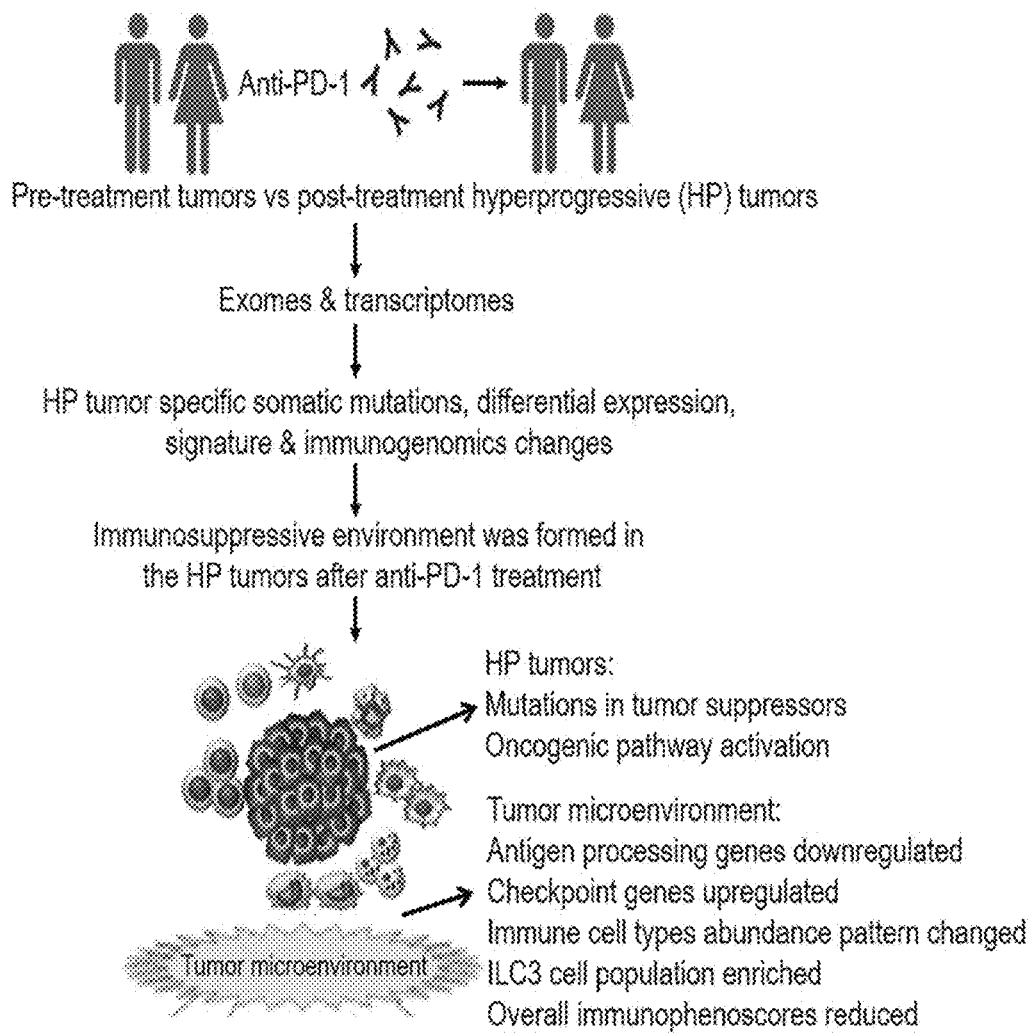

FIG. 51 is a cartoon depiction of the analysis described herein.

Figure 52:
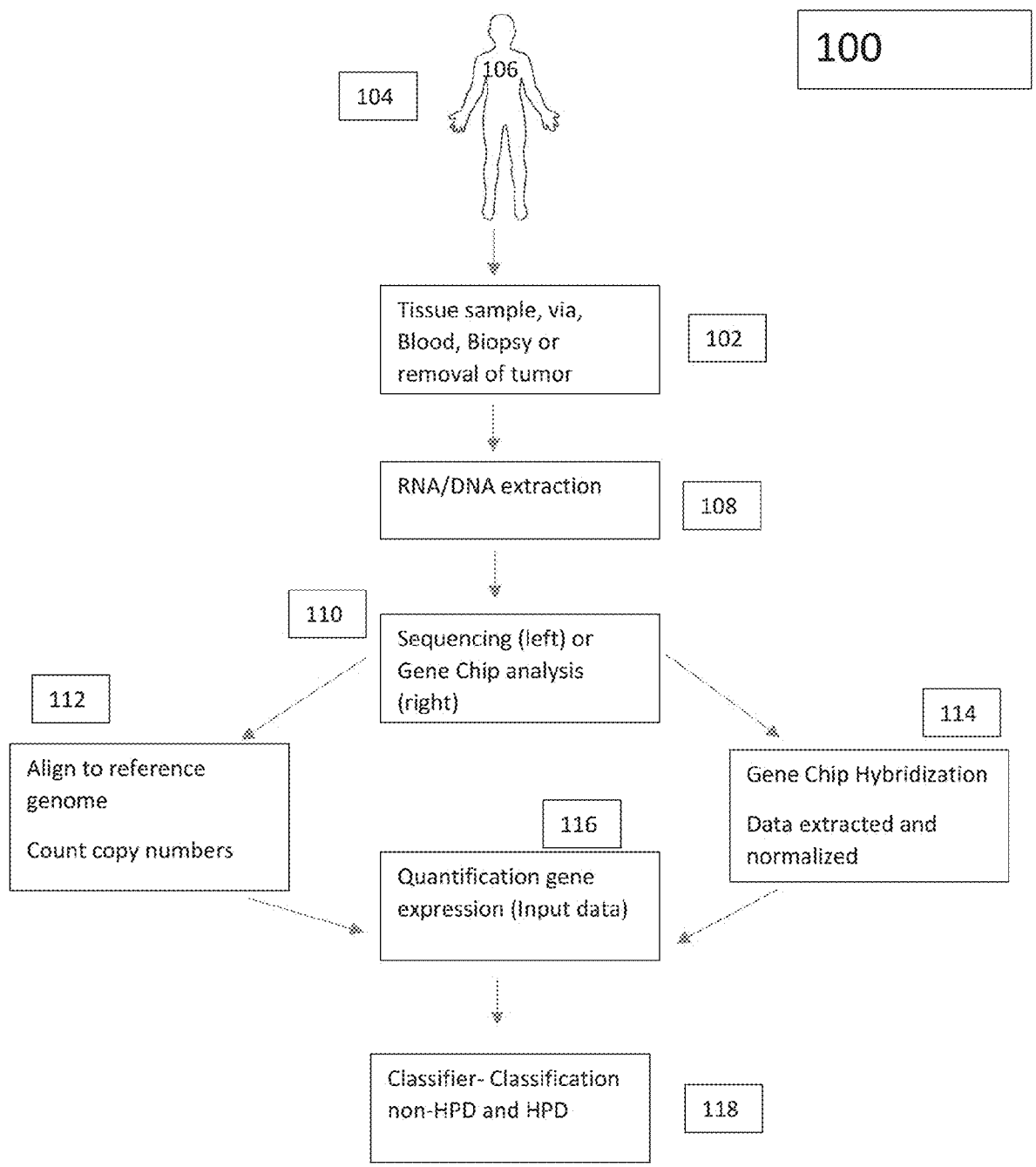

FIG. 52 is a diagram depicting RNA-seq for providing the input data.

Figure 53:
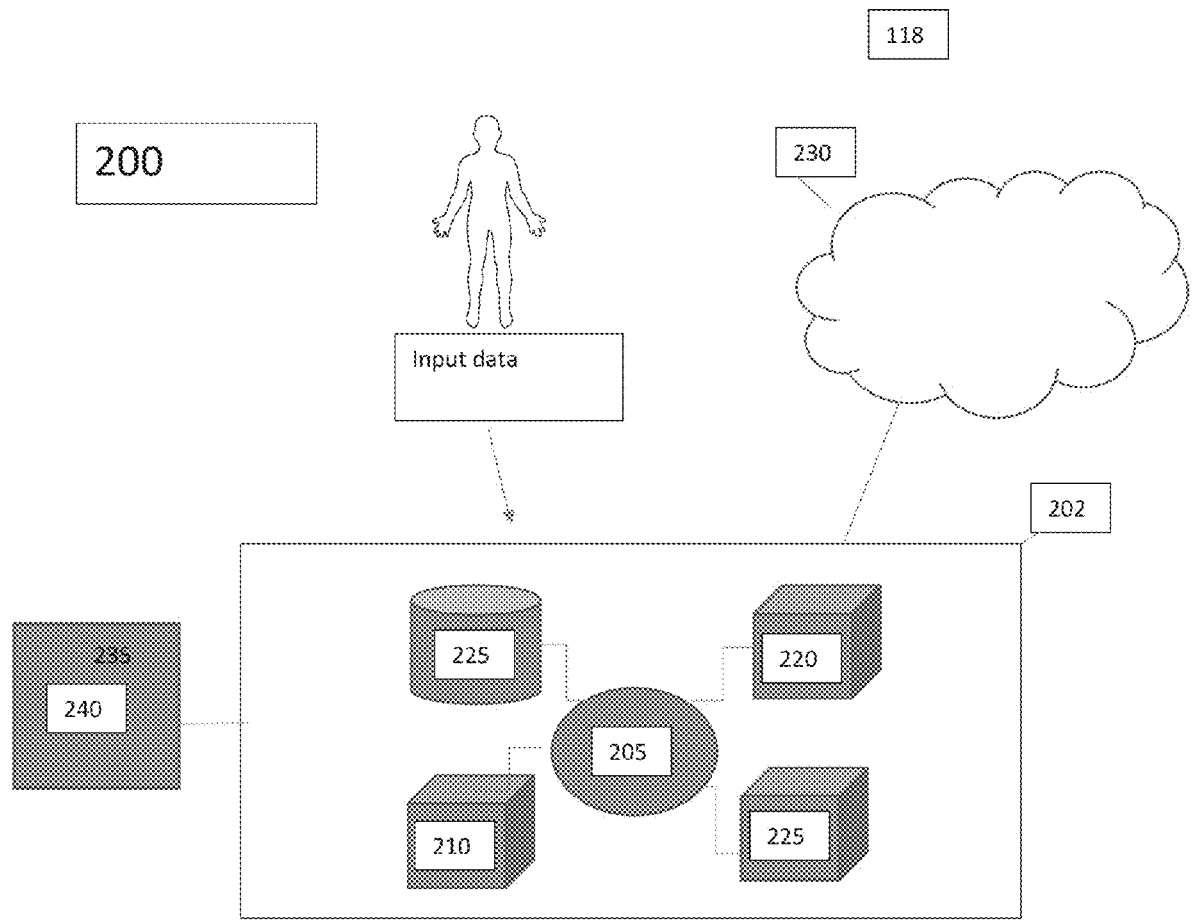

FIG. 53 is a diagram depicting the method of the current invention.

Figure 54:
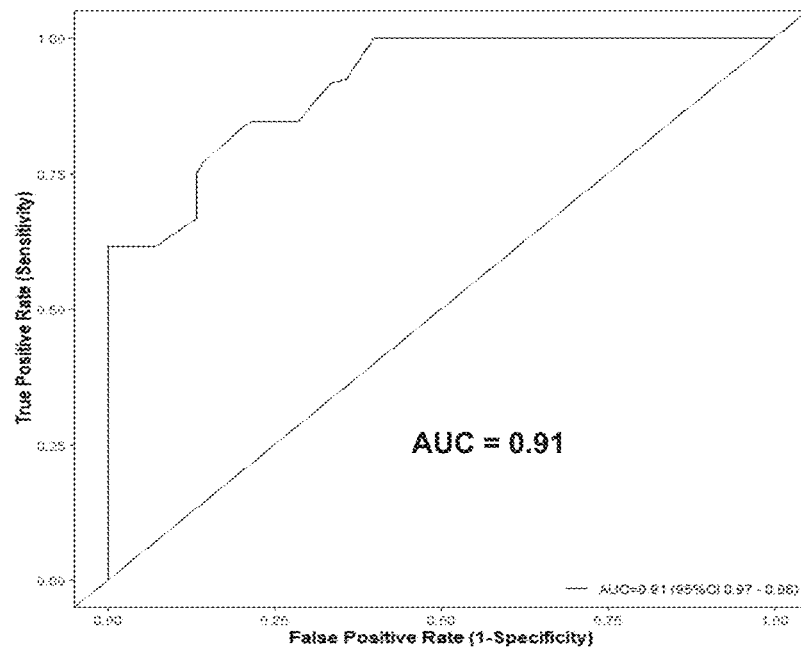

FIG. 54. Receiver operating characteristic (ROC) curves separating progressive melanoma patients from non-progressive patients in the validation dataset-GSE78220. There were 13 progressive vs 15 non-progressive melanoma patients in response to anti-PD-1 therapy. The prognostic AUC=0.91 (95% CI, 0.86-0.97).

Figure 55:
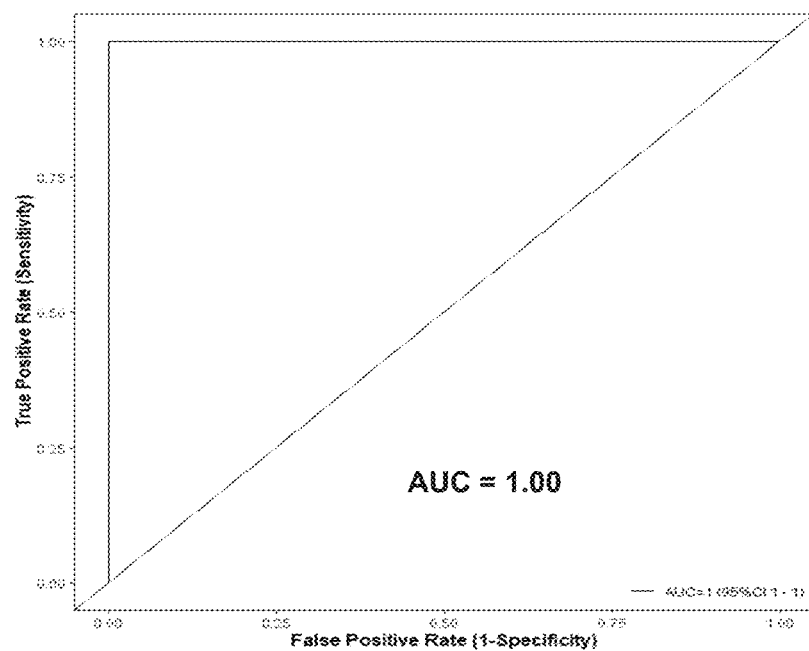

FIG. 55. Receiver operating characteristic (ROC) curves separating progressive melanoma from non-progressive melanoma samples in the validation dataset-GSE79691. There were 4 progressive vs 6 non-progressive melanoma tumors in response to anti-PD-1 therapy. The prognostic AUC=1.00 (95% CI, 1.00-1.00).

DETAILED DESCRIPTION OF THE INVENTION

In General

Although PD-1 blocking immunotherapies demonstrate significant therapeutic promise, a subset of the patients develop hyperprogressive disease (HPD) with accelerated tumor growth after anti-PD1 immunotherapy.

In this context, the inventors developed a gene expression signature predictive of HPD, which can help identify patients at risk of adverse clinical outcome after anti-PD-1 immunotherapy. The description below discloses embodiments of the present invention that are useful for patients being treated for various cancers. Referring to Example 1, based on the pre-therapy tumor expression data of Dataset_1 involving both our two samples and an outside study cohort, we developed a 121-gene set to differentiate HPD patients from non-HPD patients. The effectiveness of this 121-gene classifier in the identification of HPD patients was tested using the pre-therapy tumor expression data from Dataset_2 that was from another independent outside study cohort.

This classifier had an AUC value of 0.91 (95% confidence interval [CI], 0.87 to 0.96), a sensitivity of 71% (95% CI, 51% to 87%), and a specificity of 93% (95% CI, 80% to 99%) in predicting HPD patients in Dataset_2. Kaplan-Meier analysis of TCGA data showed that the 121-gene expression signature can significantly separate low-risk group from high-risk group in the thirteen major types of cancers including melanoma (SKCM), glioma, and carcinoma of the esophagus (ESCA), stomach (STAD), breast (BRCA), kidney (KIRC), bladder (BLCA), liver (LIHC), head and neck (HNSC), lung (LUAD & LUSC), colon (COAD) and pancreas (PAAD).

As described below in the more detailed description of the invention, it is expected that this novel 121-gene expression signature can be used to predict HPD patients after anti-PD-1 immunotherapy based on the pre-treatment tumor samples to avoid the adverse clinical outcomes following the anti-PD-1 therapy in these patients.

Development of the Present Invention

The main embodiment in this application was a gene expression profile-defined prognostic model able to predict the hyperprogressive disease (HPD) occurring in the cancer patients who developed accelerated tumor growth after anti-PD1 immunotherapy. Previously, no gene expression signature had been identified to predict which patients might develop HPD after receiving anti-PD-1 immunotherapy. This allows for the ability to avoid anti-PD-1 therapy in these patients and selecting a different cancer treatment, potentially reducing tumor volume and growth and extending patient survival.

To identify such predictors, we analyzed our own data set and the publicly available gene expression data sets of the anti-PD-1 immunotherapy studies that may contain subsets of patients who acquired HPD. Our own data set included two patients who received anti-PD-1 blockade immunotherapy. Paired tumor samples before and after anti-PD-1 treatment were obtained from a male patient with esophageal squamous cell carcinoma (Patient 1), and from a female patient with clear cell renal cell cancer (ccRCC) (Patient 2). Following anti-PD-1 treatment using pembrolizumab (Merck), these two patients demonstrated HPD, as defined by accelerated tumor growth rate and clinical deterioration using existing criteria (1). Each patient demonstrated progression at first radiologic evaluation (less than 2 months after anti-PD-1 therapy initiation).

We also searched for the outside publicly available data sets and identified two studies involving the cancer patients who were subjected to the anti-PD-1 treatment and containing a small fraction of patients that developed putative HPD. The first study (Accession #"GSE52562" in the GEO database) performed gene expression profiling of tumor biopsies before and after pidilizumab (a humanized anti-PD-1 monoclonal antibody, also called "CT-011") therapy in patients with relapsed follicular lymphoma (2). Two of eighteen follicular lymphoma patients from this study had PFS (progression free survival) less than two months after anti-PD-1 treatment. These two patients were classified as HPD patients, while the other sixteen were non-HPD patients. To develop an HPD-associated gene expression signature, the pre-therapy tumor expression data of our two HPD patients were combined with the pre-treatment tumor expression data of the two HPD patients and sixteen non-HPD patients from the GSE52562 study. This was used as the HPD signature discovery dataset (called "Dataset_1"). Another outside study (quoted as "CA209-038") assessed transcriptome changes in tumors from the patients with advanced melanoma before and after nivolumab immunotherapy (3). This CA209-038 study had 21 advanced melanoma patients having PFS<2 months after anti-PD-1 immunotherapy. Therefore, these 21 patients were classified as the HPD patients while the other 31 patients were classified as non-HPD patients. These 51 patients had pre-therapy gene expression data available, which were used as the validation dataset (called "Dataset_2").

Using the genome-wide expression data of Dataset_1 and Dataset_2, we developed and validated a 121-gene classifier using the cancerclass R package (4). The performance of the 121-gene set as a classifier was evaluated with the use of receiver-operating-characteristic curves, calculation of AUC (5), and estimates of sensitivity and specificity implemented in the cancerclass R package (6). This classification protocol starts with a feature selection step and continues with nearest-centroid classification. Fisher's exact test was used for categorical variables. All confidence intervals are reported as two-sided binomial 95% confidence intervals. Statistical analysis was performed with R software, version 3.2.3 (R Project for Statistical Computing).

Figure 9:
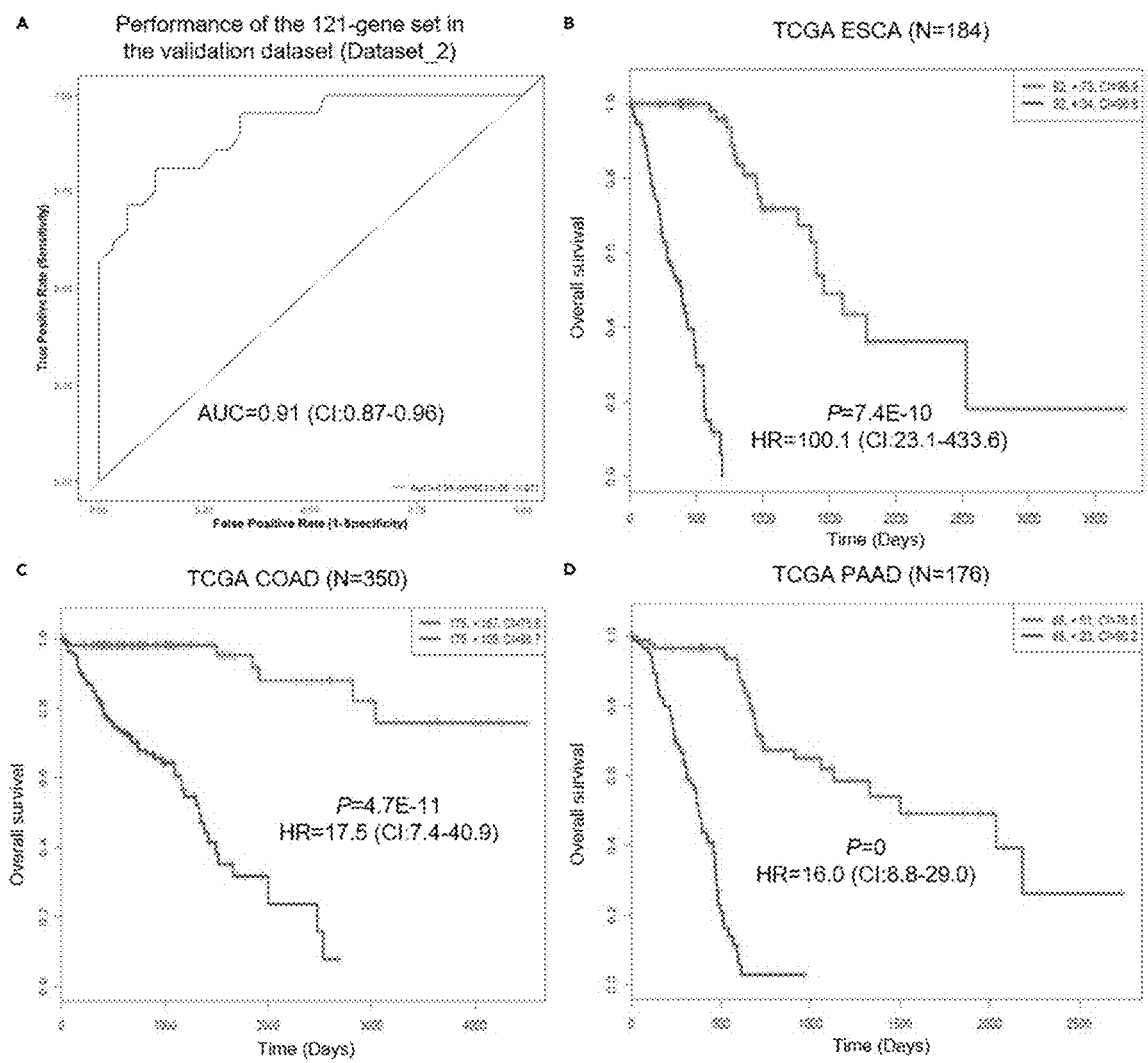
FIG. 9. Performance of the 121-Gene Set Classifier in the Validation Dataset and Its Effectiveness in the Prognosis of Worse Survival Outcome in the TCGA Datasets (A-D) (A) Receiver operating characteristic (ROC) curves shown for separating HPD patients from non-HPD patients in the validation dataset (Dataset_2, 21 HPD versus 30 non-HPD patients, AUC=0.91 (95% CI, 0.87-0.96]); Kaplan-Meier analysis showed that the 121-gene set classifier can separate significantly low- and high-risk groups in all of the 13 major TCGA cancers, of which the top three cancers with greatest hazard ratios (HRs) were shown in (B) ESCA (HR=100.1, 95% CI, 23.1-433.6); (C) COAD (HR=17.5, 95% CI, 7.4-40.9), and (D) PAAD datasets (HR=16.0, 95% CI, 8.8-29.0). See also FIGS. 18-21.
Figure 18:
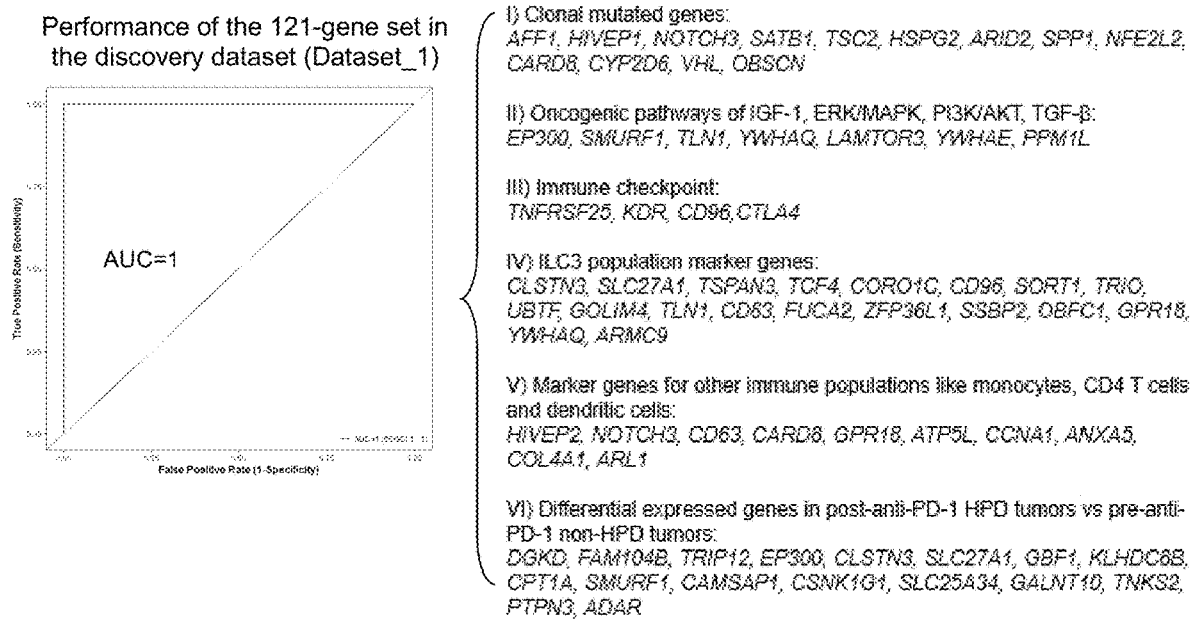
FIG. 18 Results of the 121-gene expression signature in the discovery data set (Dataset_1). Related to FIG. 9. ROC curves was shown for separating HPD patients from non-HPD patients in the discovery data set (4 HPD vs 16 non-HPD patients, AUC=1). The majority of these genes (70 of 121) belonged to the gene sets that we identified as significant to different aspects of the HPD tumors in our samples. Specifically, these genes were classified into the following six categories.
Figure 19:
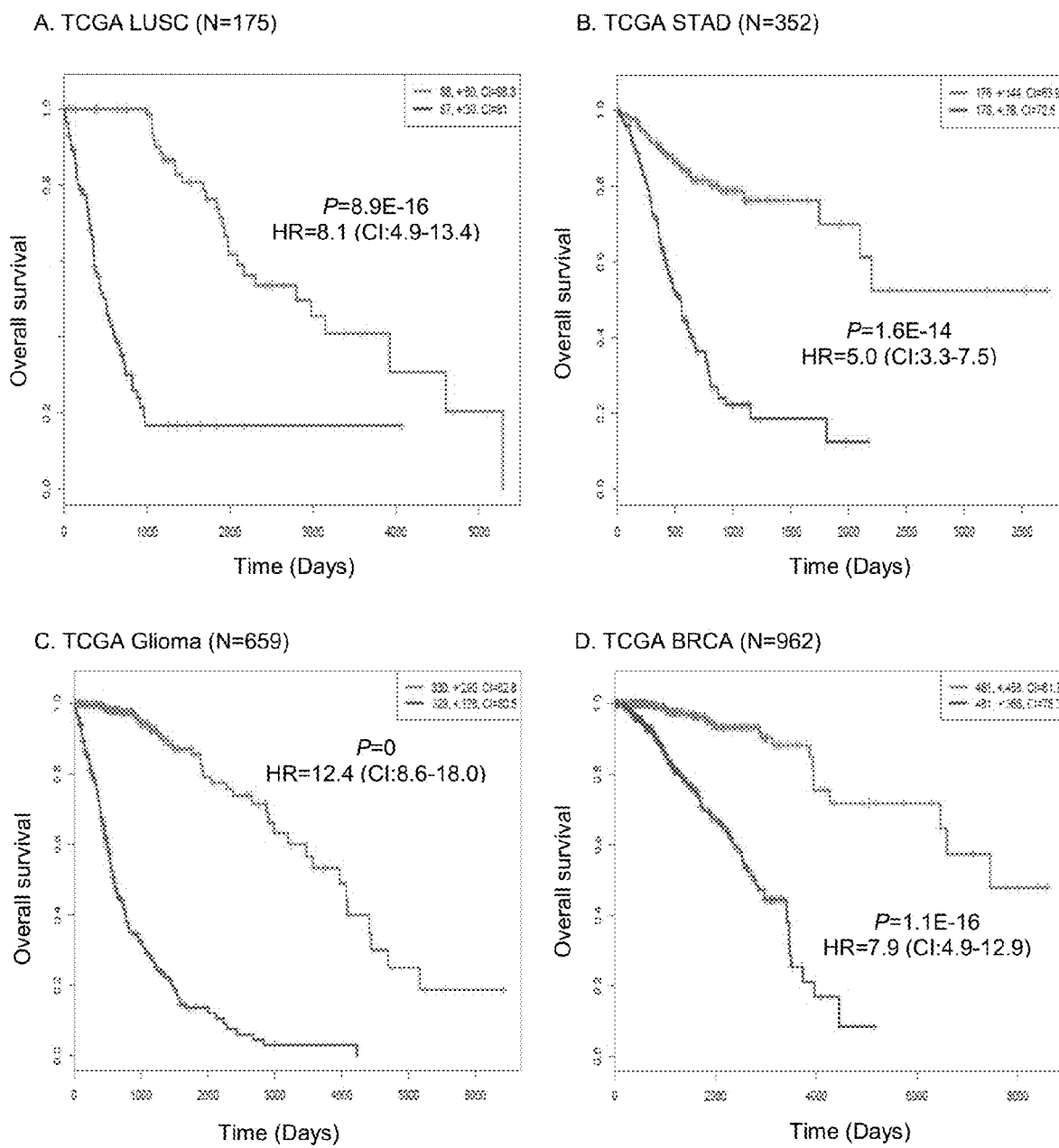
FIG. 19 Kaplan-Meier analysis showed that the 121-gene set classifier can separate significantly low- and high-risk groups in the 13 major TCGA cancers. Related to FIG. 9. The Kaplan-Meier curves of the TCGA cancer types of (A) LUSC, (B) STAD, (C) glioma, (D) BRCA were shown in this figure.
Figure 20:
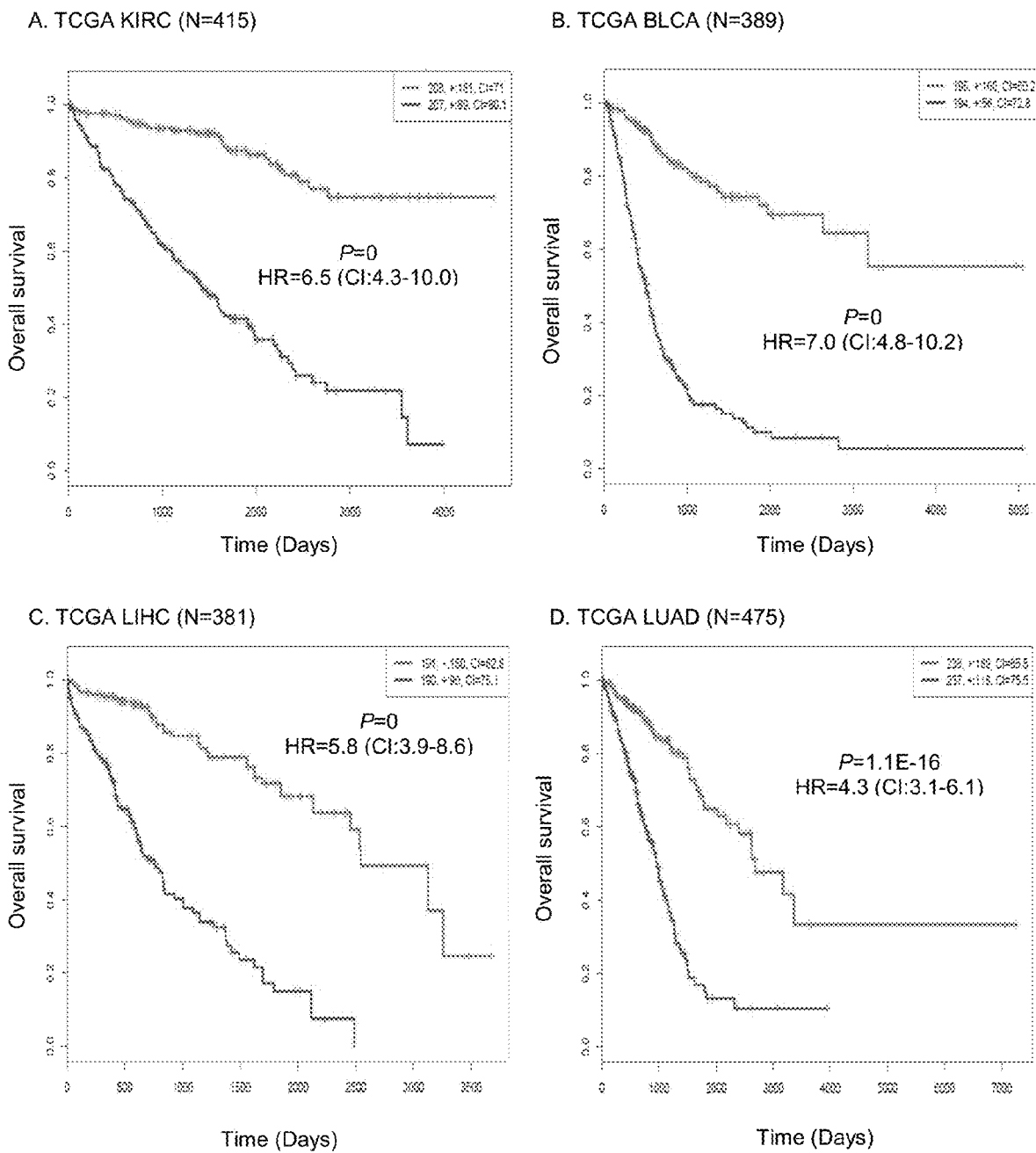
FIG. 20 Kaplan-Meier analysis showed that the 121-gene set classifier can separate significantly low- and high-risk groups in the 13 major TCGA cancers. Related to FIG. 9. The Kaplan-Meier curves of the TCGA cancer types of (A) KIRC, (B) BLCA, (C) LIHC, (D) LUAD were shown in this figure.
Figure 21:
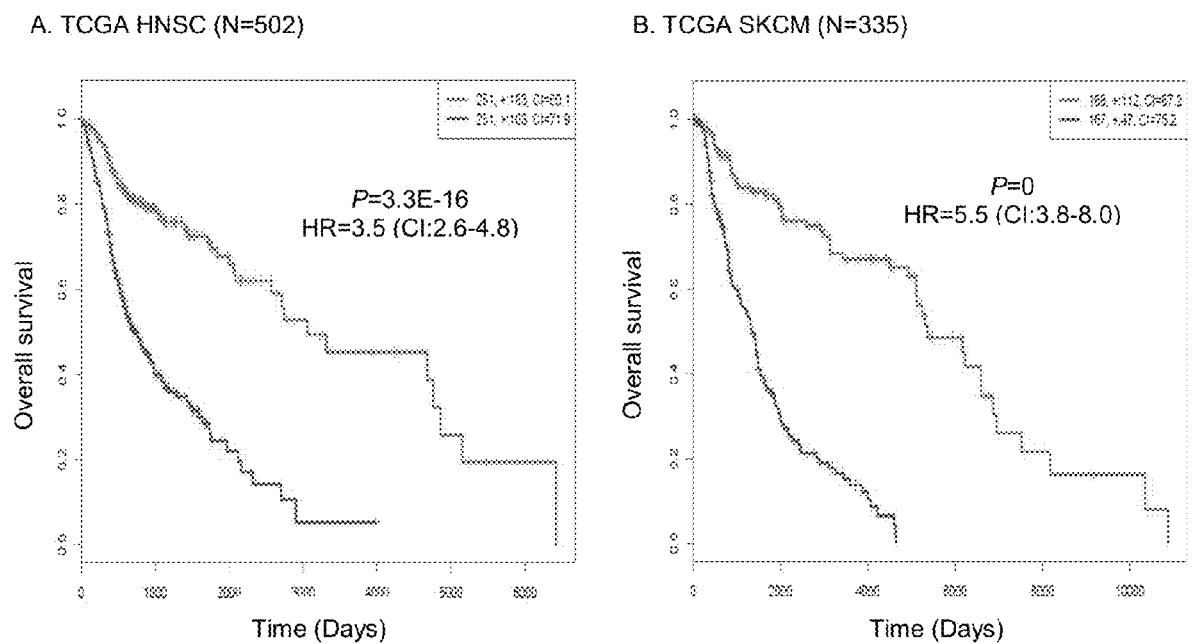
FIG. 21 Kaplan-Meier analysis showed that the 121-gene set classifier can separate significantly low- and high-risk groups in the 13 major TCGA cancers. Related to FIG. 9. The Kaplan-Meier curves of the TCGA cancer types of (A) HNSC, (B) SKCM were shown in this figure.

First, based on the pre-anti-PD-1 immunotherapy tumor expression data of Dataset_1, we developed a 121-gene set to differentiate HPD patients from non-HPD patients (FIG. 18, Table 4). Then the effectiveness of this 121-gene classifier in the identification of HPD patients was further validated using the pre-therapy tumor expression data from Dataset_2. This classifier had an AUC value of 0.91 (95% confidence interval [CI], 0.87 to 0.96), a sensitivity of 71% (95% CI, 51% to 87%), and a specificity of 93% (95% CI, 80% to 99%) in predicting HPD patients in Dataset_2 (FIG. 9).

The experimental procedures used in our own study were described as follows: At least five 10-mm Formalin-Fixed Paraffin-Embedded (FFPE) slides were used for each tumor specimen, from which RNA samples were extracted and subjected to RNA-seq after library construction and purification. The Illumina TruSeq RNA Access kit was used for the preparation of RNA-seq libraries that were sequenced to the average depth of 75 million reads in the paired end 100 bp (PE100) mode using the HiSeq 2500 system. Raw RNA-seq data quality was checked using the FastQC program via the Babraham Bioinformatics website. Raw sequence data reads in fasta format were first processed through Perl scripts (7).

Data were then refined by removing reads containing adapter, poly-N, or low-quality reads (8, 9). All downstream analyses were based on refined data. The "rsem prepare reference" script of the RSEM package was used to generate reference transcript sequences by using the gene annotation file (GTF) format and the full genome sequence (FASTA)

format of human GRCh37 assembly. All of the quality reads of different samples were mapped to generated reference transcript sequences using the Bowtie-2 program (10) to determine the identity between cDNA sequences and corresponding genomic exons in regions of exact matches. The "rsem calculate expression" script of RSEM was used to analyze both the alignment of reads against reference transcript sequences and the calculation of relative abundances. Normalized gene expression values were used as the input data for the construction of the gene expression signatures for HPD after anti-PD-1 immunotherapy.

One of skill in the art would typically adapt the procedure above to perform the methods of the present invention.

To understand whether this 121-gene expression signature or its subsets of genes can be used as biomarkers of specific cancer types, we also tested the prognostic performance of the 121-gene signature using gene expression data from the TCGA tumor samples in conjunction with the online biomarker validation tool and database—SurvExpress (11). First of all, Kaplan-Meier survival analyses were implemented to estimate the survival functions after the samples were classified into two risk groups according to their risk scores based on the 121-gene set. Differences in survival risk between the two risk groups were assessed using the Mantel-Haenszel log-rank test. It was found that the 121-gene signature derived risk scores significantly associated with overall survival in 13 TCGA cancer types, which included melanoma (SKCM), low grade glioma (LGG), and carcinoma of the esophagus (ESCA), stomach (STAD), breast (BRCA), kidney (KIRC), bladder (BLCA), liver (LIHC), head and neck (HNSC), lung (LUAD & LUSC), colon (COAD) and pancreas (PAAD) (FIG. 9, FIG. 19-21).

In addition to the overall 121-gene-expression signature for pan-cancer HPD, different subsets of the overall 121 genes were identified to classify each type of 13 TCGA studied cancers from normal controls. The expression of individual genes with overall survival in patients of each specific cancer type was also investigated.

Table 7 lists suitable gene subsets of the 121-gene signature that may serve as prognostic biomarkers for specific cancers and show significant association with overall survival in each of the 13 TCGA cancer types. The diagnostic value of these cancer subtype-specific biomarkers in predicting tumors is shown in FIGS. 26-37. The association with overall survival outcome was shown in FIGS. 28-50.

A combination of bioinformatics tools (classifier system) and clinical data is used to identify gene signatures for predicting the cancer occurrence. Some suitable classifier systems are described more below. Glmnet R package (12) is first used to verify the signature of 121-gene in prediction of the cancer occurrence. The clinical data from The Cancer Genome Atlas (TCGA) is downloaded to further refine the gene signature.

Glmnet is a package that fits a generalized linear model via penalized maximum likelihood (12). The basic concept of generalized linear model is to assign a coefficient (a) to each independent variable (x) to predict the dependent variable (y). In our case, we use least absolute shrinkage and selection operator (Lasso) (13) regression implemented in Glmnet package to generate the prediction signature. Lasso model performs both variable selection and regularization in order to enhance the prediction accuracy and interpretability of the statistical model it produces.

Assuming sample size=n and p genes detected in each sample, the goal of the Lasso algorithm is to minimize:

$$\sum_{i=1}^{n}\left(y_i - \sum_{j} x_{ij}\beta_j\right)^2 + \lambda \sum_{j=1}^{p} |\beta_j|$$

In the above model, left side represents the prediction error and right side represents the variable selection. A tuning parameter, $\lambda$ controls the strength of the penalty. $\lambda$ is basically the amount of shrinkage:
1. When $\lambda=0$, no parameters are eliminated. The estimate is equal to the one found with linear regression.
2. As $\lambda$ increases, more and more coefficients are set to zero and eliminated and bias increases.
3. As $\lambda$ decreases, variance increases. Glmnet will randomly divide the training dataset into 10 folds and perform cross-validation to generate the optimal $\lambda$ for the prediction model.

To evaluate the effect of gene signatures, we first assembled a pooled dataset of normal controls because several cancer types in the TCGA dataset do not have normal tissue gene expression data or only have very few normal samples. We randomly selected 100 normal samples from the 13 TCGA cancer types and combined them with tumor samples to get a pooled dataset for each cancer type. For a specific cancer type, 75 percent of the pooled dataset are randomly selected to be training dataset and the other 25 percent of the pooled dataset are the testing dataset. After generating the optimal X from training data, we perform receiver operating characteristic (ROC) analysis for testing dataset to assess the prediction model via R software. The area under the ROC curve (AUC) can be used as an accuracy measure of the ROC curve. A higher prediction accuracy is evidenced by a larger AUC.

We conducted the above analysis for each subset of the 121-gene signature listed in Table 7. FIGS. 26-37 showed that the 121-gene signature (red line) has the similar power for detecting the cancer occurrence comparing to using all genes in genome as variables (black line). The prediction accuracies are still very high (green line, AUC>0.9) when we only use the specific subset of the 121-gene signature for each cancer type given in Table 7, except for STAD (AUC=0.81). However, when we further reduce gene numbers in the subsets (blue and turquoise lines), the prediction accuracies significantly attenuate in all the 13 cancer types, especially in several cancer types such as BRCA, COAD, LIHC and STAD.

Embodiments of the Present Invention

As described above, one embodiment of the present invention involves examining a patient tumor for the gene expression profile of a set of biomarkers. In one embodiment, the set is the 121 member set disclosed below and as examined in FIGS. 9B-9D and 17-18.

One would examine the tumor's biomarker signature to evaluate whether the signature was similar to an HPD-positive signature. One would use statistical tools as described in the present application (or similar tools) to develop an expression signature. One may need to employ control or training samples in order to develop a diagnosis. Useful control samples would be tumor samples from patients who did not develop HPD and samples of tumors before the application of the immunotherapy.

All the members of the 121 gene set are listed in Table 4. The current 121 gene-set was derived based on a mixed types of cancers due to the very few HPD cases available. The gene expression signature of the 121 genes can serve as a reservoir based on which the likelihood of a patient to develop HPD can be calculated. The expression of these genes should be used as predictor variables in a statistical model such as Cox proportional hazard model to calculate the risk of having HPD. For the prognostic of HPD that is based on the overall expression pattern of these biomarkers, it is not important to address the question of whether the expression of these genes goes up or down or how much the expression level changes. Table 4 details the information of all the 121 genes. For prediction of HPD in the patient samples to be tested, the gene expression profiling may be conducted for this 121-gene set. Patients may be classified based on the quantitative expression profiles using any means known in the art. For example, the risk scores of a patient cohort may be generated using a Cox proportional hazard model incorporating the 121 genes as predictors. Patients with a risk score greater than the certain cutoff are defined as high risk of developing HPD, whereas patients with a risk score less than the cutoff are classified as low risk. Cutoffs must be defined for patient stratification based on specific clinical setting of the new samples.

A patient's prognostic categorization can also be determined by using a statistical model or a machine learning algorithm, which computes the probability of developing HPD based on this patient's gene expression profiles of the 121-gene set. Potential users can use the program we described such as the R programming environment that can be freely downloaded from the website to perform gene expression data analysis of these 121 genes to predict the likelihood of having HPD in new patients.

As described above, FIGS. 26-37 showed that the 121-gene signature (red line) has a similar power for detecting the cancer occurrence comparing to using all genes in genome as variables (black line). Therefore, one could use an examination of the entire 121 marker set to provide information on the HPD status of each of these tumor types.

In certain embodiments of the present invention, one would not use all 121 biomarkers for the examination. For example, one could use at fewer than 121 biomarkers and achieve a result of at least AUC greater than 0.90.

The prediction accuracies are still very high (green line, AUC>0.9) when we only use the specific subset of the 121-gene signature for each cancer type given in Table 7, except for STAD (AUC=0.81). However, when we further reduce gene numbers in the subsets (blue and turquoise lines), the prediction accuracies significantly attenuate in all the 13 cancer types especially in several cancer types such as BRCA, COAD, LIHC and STAD.

The method is still suitable for use if one uses less than the number of genes listed in Table 2. As stated before, the definition of a good value AUC is relative and not absolute. If we further reduced the number of genes in the subsets to below that listed in Table 7, the results of AUC will not be as predictive as those obtained using the subsets listed in Table 7 but may be suitable for some purposes.

Therefore, the biomarkers listed in Table 7 may be used as a smaller subset to examine a patient's tumor for HPD status. One would typically use all of the genes in the subset. In some embodiments, one would use fewer genes, such as removing 1, 2, 3 or 4 genes from the panel.

In one embodiment, the present disclosure provides a method for processing a test sample to determine a likelihood that a patient develops HPD in response to anti-PD-1 immunotherapy in a patient, comprising: (a) receiving information indicative of an expression level of a plurality of biomarkers in a tumor sample extracted from the patient; (b) providing the plurality of biomarker levels as input to a classifier configured to predict likelihood that a patient develops hyperprogesssive disease in response to anti-PD-1 immunotherapy in a computer to classify the test sample, wherein the classifier was trained with a plurality of training samples comprising pre-therapy tumor expression data of known HPD patients and pre-therapy tumor expression data of known non-HPD patients; and (c) receiving, from the classifier, an output report that identifies said classification as indicative of the likelihood that the patient develops hyperprogesssive disease in response to anti-pd-1 immunotherapy.

For step (a), input data can be derived from a tumor tissue sample from a subject or patient by any means known in the art to identify and quantify the gene expression signature within a sample. Suitable methods including, but are not limited to, for example, cDNA microarrays, various generations of Affymetrix gene chips (Affymetrix, Santa Clara, CA), real-time reverse transcription polymerase chain reactions (qPCR), RNA sequencing or other next generation sequencing methods known in the art. The method may further comprise detecting the expression level of the plurality of biomarkers by sequencing the nucleic acid molecules from the sample to yield data comprising one or more levels of gene expression producing is the sample. In one embodiment, RNA sequencing (RNA seq) is used to gather data input for the classifier. Processing of samples for RNA sequencing are known in the art and include, but are not limited to, one or more of the following steps e.g., RNA extraction, poly-A selection (e.g., via magnetic beads), fragmentation and random priming, first and second strand cDNA synthesis to produce a cDNA library, end-repair, phosphorylation and A-tailing, adapter ligation, PCT amplification and sequencing. Adaptors are specific constant sequences known in the art used for sequencing. The cDNA library is a collection that can be sequences using short-read sequencing which produces millions of short sequence reads that correspond to individual cDNA fragments. Suitable methods of RNA seq are described in the examples below, and can be found in the art. Methods of performing an RNA-seq experiment can be 1) random-primed cDNA synthesis from double-stranded cDNA or 2) RNA-ligation methods (reviewed and compared in Levin 2010, incorporated by reference in its entirety), for example, Illumina's TruSeq RNA-seq, which is a random-primed cDNA synthesis non-strand-specific protocol. Once a sequencing cDNA library is established, it is sequenced to a specified depth, and these reads are aligned to the genome or transcriptome and are counted to determine differential gene expression or further analyzed to determine splicing and isoform expression.

For step (b) a computer (200) may be used as a classifier to compare the input data from the patient with the classifier biomarker signature of the plurality of biomarkers described in Table 4. Suitable computer systems and methods of machine learning to establish the biomarker signature and classifier are described herein more below. Generally, machine learning algorithms are used to construct models that accurately assign class labels to examples based on the input features that describe the example. In some case it may be advantageous to employ machine learning and/or deep learning approaches for the methods described herein. The computer may run an algorithm that implements the classification, and done by machine learning. This determination, analysis or statistical classification is done by methods known in the art, including, but not limited to, for example, a wide variety of supervised and unsupervised data analysis, machine learning, deep learning, and clustering approaches including hierarchical cluster analysis (HCA), principal component analysis (PCA), Partial least squares Discriminant Analysis (PLS-DA), random forest, logistic regression, decision trees, support vector machine (SVM), k-nearest neighbors, naive bayes, linear regression, polynomial regression, SVM for regression, K-means clustering, and hidden Markov models, among others.

Tissue samples may be obtained from a patient, preferably a patient having cancer. Suitable tissue samples include, but are not limited to, for example, a blood sample (for leukemia), a biopsy sample, or a surgical resectioned tissue section, among others. Methods of obtaining a tumor samples are readily known by one skilled in the art, and include, for example, needle biopsy, and the like.

In some embodiments, the classifier has an accuracy of at least 85%. In some embodiments, the classifier sensitivity of at least 70%. In other embodiments, the classifier generates said classification at a specificity of at least about 90%. Methods of determining the accuracy, sensitivity and specificity are known in the art, and can be measured, for example, by determining the area under the curve. Preferably, in some embodiments, the area under the curve (AUC) has a value of 0.9 or greater.

In some embodiments, the plurality of biomarkers comprises 10, 20, 30, 40, 50, 60, 70, 80, 90, 100, 110, or 120 of the biomarkers listed in Table 4. In one embodiment, the classifier uses the input data from a plurality of biomarkers that consists of the 121 biomarkers in Table 4. In another embodiment, the classifier uses input data from a subset of the 121 biomarkers listed in Table 4 for classification, wherein the members of the subset are dependent on the type of cancer examined, and wherein the members of the subset and tumor types are listed in Table 7. Suitably, the classifier uses input from all the biomarkers listed in Table 7 associated with the suspected type of cancer.

The term subject or patient are used herein interchangeably, and are preferably a mammal, preferably a human, having cancer. Suitably, the patient or subject has a cancer that may be treated with PD-1 therapy. In some embodiments, the patient's tumor is of a type selected from the group consisting of bladder carcinoma, breast invasive carcinoma, colon adenocarcinoma, esophageal carcinoma, head and neck squamous cell carcinoma, kidney renal clear cell carcinoma, brain lower grade glioma, liver hepatocellular carcinoma, lung adenocarcinoma, lung squamous cell carcinoma, pancreatic adenocarcinoma, skin cutaneous melanoma, and stomach adenocarcinoma, among others.

In some embodiments, step (b) comprises identifying a copy number variation or a variant in the nucleotide input data.

Suitable sources to train the classifier are known in the art. A clinician skilled in the art would be able to determine known HPD samples, e.g., a cancer tissue sample from esophageal cancer, renal cell cancer, follicular lymphoma, or any combination thereof, in which the subject, after being treated with anti-PD-1 immunotherapy, developed HPD.

In some embodiments, the plurality of training samples further comprises a normal tissue sample. In one example, the validation samples comprise a melanoma tissue was from a patient that developed hyperprogressive disease (HPD), and wherein said classifier does classify said sample as likely to develop HPD. In another example, the validation sample is melanoma tissue from a patient treated with anti-PD-1 therapy that did not develop HPD, and wherein said classifier classifies said sample of melanoma tissue as not likely to develop HPD.

The methods described herein to classify the subject's likelihood to develop HPD is performed before the subject is treated with a PD-1 therapy. This in turn, allows the health care provide to avoid treatment with PD-1 therapy in a subject that has a high likelihood of developing HPD, and thus the care provider can select a different cancer treatment instead of PD-1 immunotherapy.

In some embodiments, the method further comprising: determining, based on the output, that the patient is unlikely to develop hyperprogesssive disease in response to anti-PD-1 immunotherapy; and administering anti-PD-1 immunotherapy to the patient based on the determination that the patient is unlikely to develop hyperprogesssive disease in response to anti-PD-1 immunotherapy.

Suitable anti-PD-1 immunotherapies are known in the art, and include anti-PD-1 therapy and anti-PD-L1 therapy. In some embodiments, the PD-1 inhibitor comprises an antibody. In other embodiments, the PD-1 inhibitor is selected from the group consisting of Nivolumab (anti-PD-1), Pembrolizumab (anti-PD-1), and combinations thereof. In some embodiments the PD-1 immunotherapy comprises a PD-L1 inhibitor. Suitable PD-L1 inhibitors include, for example, a PD-L1 inhibitor selected from the group consisting of atezolizumab, avelumab, durvalumab, and combinations thereof. Examples include, but are not limited to, nivolumab, an anti-PD-1 antibody, available from Bristol-Myers Squibb Co and described in U.S. Pat. Nos. 7,595,048, 8,728,474, 9,073,994, 9,067,999, 8,008,449 and 8,779,105; pembrolizumab, and anti-PD-1 antibody, available from Merck and Co and described in U.S. Pat. Nos. 8,952,136, 83,545,509, 8,900,587 and EP2170959; atezolizumab is an anti-PD-L1 available from Genentech, Inc. (Roche) and described in U.S. Pat. No. 8,217,149; avelumab (Bavencio, Pfizer, formulation described in PCT Publ. WO2017097407), durvalumab (Imfinzi, Medimmune/AstraZeneca, WO2011066389), cemiplimab (Libtayo, Regeneron Pharmaceuticals Inc., Sanofi), spartalizumab (PDR001, Novartis), camrelizumav (AiRuiKa, Hengrui Medicine Co.), sintillimab (Tyvyt, Innovent Biologics/Eli Lilly), KN035 (Envafolimab, Tracon Pharmaceuticals); tislelizumab available from BeiGene and described in U.S. Pat. No. 8,735,553; among others and the like. Other PD-1 and PD-L1 that are in development may also be used in the practice of the present invention, including, for example, PD-1 inhibitors including toripalimab (JS-001, Shanghai Junshi Biosciences), dostarlimab (GlaxoSmithKline), INCMGA00012 (Incyte, MarcoGenics), AMP-224 (AstraZeneca/MedImmune and GlaxoSmithKline), AMP-514 (AstraZeneca), and PD-L1 inhibitors including AUNP12 (Aurigene and Laboratoires), CA-170 (Aurigen/Curis), and BMS-986189 (Bristol-Myers Squibb), among others. Such therapies are known by those skilled in the art. In some embodiments, the PD-1 inhibitor is selected from the group consisting of Nivolumab (anti-PD-1), Pembrolizumab (anti-PD-1), and combinations thereof. In some embodiments, the PD-L1 inhibitor is selected from atezolizumab, avelumab, and durvalumab, among others.

In some embodiments, if it is determined that the subject has a high likelihood of developing HPD, the subject is not treated with an anti-PD-1 immunotherapy, and another cancer therapy is selected. Other known cancer therapies are known in the art and include, but are not limited to, for example, surgery, chemotherapy, radiation, immunotherapy, targeted drug therapy, cryoablation, hormone therapy, bone marrow transplants, and the like.

Classifier System and Computer Processing

For training of the classifier system, patients were separated in to a HPD and non-HPD cohort after PD-1 immunotherapy. HPD was defined as (1) progression at first restaging on therapy, (2) increase in tumor size >50%, and (3) >2-fold increase in tumor growth rate (TGR). Based on these criteria, two cohorts in the datasets that received anti-PD-1 treatment and contained patients that developed putative HPD.

The list of the 121 classifier genes developed can be found in Table 4. We used the cancerclass R package (Budczies J, Kosztyla D, Torne C V, et al. cancerclass: An R Package for development and validation of diagnostic tests from high-dimensional molecular data. *J Stat Software.* 2014; 59(1):1-19, incorporated by reference) to build the classifier based on the gene expression values of these 121 genes. The classifier (predictor) is constructed using the nearest-centroid algorithm implemented in the cancerclass R package. In other words, the type of working classifier is the nearest-centroid classifier. Four methods dist="euclidean", "center", "angle", "cor" are available for calculation of the distance between test samples and the centroids (see documentation of predict-method in the cancerclass R package (Budczies et al.). The option dist="cor" was used to calculate classifier based on the expression values of the 121 classifier genes.

The gene expression can be acquired from any method known in the art. In one embodiment, RNA-seq data is used to generated gene expression data in the field. The raw RNA-seq data of the 121-gene set will be pre-processed, normalized and transformed to the input data for the nearest-centroid classifier. The MLSeq R package (Goksuluk D, Zararsiz G, Korkmaz S, et al. MLSeq: Machine learning interface for RNA-sequencing data. *Comput Methods Programs Biomed.* 2019; 175:223-231, incorporated by reference in its entirety related to nearest-centroid classifier) is a software to be used to processing the data for input to the classifier. The descriptions of the data processing steps are as follows: 1) Pre-processing: MLSeq package expects a count matrix that contains the number of reads mapped to each transcript for each sample. This type of count data can be generated from raw RNA-seq data (in .fastq files) from Linux-based softwares such as htseq-count function in HTSeq (see, e,g, Anders S, Pyl PT, Huber W. HTSeq—a Python framework to work with high-throughput sequencing data. *Bioinformatics.* 2015; 31(2):166-169, incorporated by reference in its entirety); 2) Normalization: This is a crucial step of RNA-Seq data analysis. It can be defined as the determination and correction of the systematic variations to enable samples to be analyzed in the same scale. These systematic variations may arise from both between-sample variations including library size (sequencing depth) and the presence of majority fragments; and within-sample variations including gene length and sequence composition (GC content). In MLSeq, two effective normalization methods are available. First one is the "deseq median ratio normalization", which estimates the size factors by dividing each sample by the geometric means of the transcript counts (see, e.g., Love M I, Huber W, Anders S. Moderated estimation of fold change and dispersion for RNA-seq data with DESeq2. *Genome Biol.* 2014; 15(12):550, incorporated by reference). Median statistic is a widely used statistics as a size factor for each sample. Another normalization method is "trimmed mean of M values (TMM)". TMM first trims the data in both lower and upper side by log-fold changes (default 30%) to minimize the log-fold changes between the samples and by absolute intensity (default 5%). After trimming, TMM calculates a normalization factor using the weighted mean of data. These weights are calculated based on the inverse approximate asymptotic variances using the delta method (see, e.g., Robinson M D, Oshlack A. A scaling normalization method for differential expression analysis of RNA-seq data. *Genome Biol.* 2010; 11(3):R25, incorporated by reference). Raw counts might be normalized using either deseq-median ratio or TMM methods. 3) Transformation: After normalization, it is needed to apply an appropriate transformation on the normalized data. MLSeq allows researchers perform one of transformations: log-cpm, vst and r log. The possible normalization-transformation combinations are: deseq-vst, deseq-r log, deseq-log cpm, and tmm-log cpm. The transformed data can be used for input to the nearest-centroid classifier.

The classifier output is the result of the prediction based on the nearest-centroid classifier that takes the gene expression count matrix of the 121 classifier as input. The prediction result is a continuous score for each of the tumor samples from the cancer patients. Three methods score="z", "zeta", "ratio" are available for calculation of the prediction score (see documentation prediction-class in the cancerclass R package (see, e.g., Budczies et al). The prediction score increases for patients that develop HPD. The higher the prediction score, the more likely the patient will develop HPD. In some embodiments, the specific cutoff value of the continuous prediction score to claim the development of HPD depends on the individual expression dataset of the 121 classifier genes that can be generated from the specific cohort of cancer patients using a given gene expression profiling platform such as the Illumina HiSeq 4000 Systems for RNA-seq. In one embodiment, the cutoff prediction score value will be defined according to clinical requirements to allow to balance sensitivity and specificity of the AUC curve. For example, in one embodiment, a prediction score of zeta ≥0.5 calculated from the data set is provided which can render the values of sensitivity ≥0.9 and specificity ≥0.8.

In one embodiment, for training the classifier system, gene expression profiling of tumor biopsies before and after pidilizumab (a humanized anti-PD-1 monoclonal antibody, also called "CT-011") therapy in patients with cancer (e.g., study (Accession #"GSE52562" in the GEO database) performed with relapsed follicular lymphoma (Westin et al., 2014)). As demonstrated in the Examples, patients are separated by the development of HPD (e.g., Table 3). To develop an HPD-associated gene expression signature, the pre-therapy tumor expression data of HPD patients were combined and compared to the non-HPD patients to provide a dataset (dataset 1). Another validation set of data is shown in Table 5, where 21 patients were classified as the HPD patients and 31 patients were classified as non-HPD patients which had pre-therapy gene expression data available, and this dataset was used as the validation dataset (called "Dataset_2"). Based on the genome-wide expression data of Dataset_1 and Dataset_2, we developed and validated a 121-gene classifier using the cancerclass R package (Budczies et al., 2014, incorporated by reference in its entirety).

The performance of the 121-gene set as a classifier was evaluated with the use of receiver-operating-characteristic curves, calculation of AUC (Hanley and McNeil, 1982), and estimates of sensitivity and specificity implemented in the cancerclass R package (Jan et al., 2014). This classification protocol starts with a feature selection step and continues with nearest-centroid classification. Fisher's exact test was used for categorical variables. Statistical analysis can be performed with software known in the art, for example, R software, version 3.2.3 (R Project for Statistical Computing).

In another embodiment, the prognostic performance of the 121-gene signature using gene expression data from the TCGA tumor samples in conjunction with the online biomarker validation tool and database-SurvExpress (Aguirre-Gamboa et al., 2013) was performed.

Specifically, Kaplan-Meier survival analyses were implemented to estimate the survival functions after the samples were classified into two risk groups according to their risk scores based on the 121-gene set. Differences in survival risk between the two risk groups were assessed using the Mantel-Haenszel log-rank test.

FIG. 52 shows an exemplary scheme of the presently disclosed system 100. As shown at step 1 of FIG. 52, a biological sample (e.g., blood, tissue 102) can be collected from a subject 104 having a signature 106 (e.g., a HPD disease). Suitable biological samples 102 include, but are not limited to, tissue sample, blood sample, lung lavage, and the like. In a preferred embodiment, the sample is a tumor tissue. In some examples, the tumor tissue is obtained from biopsy, e.g., needle biopsy or surgery.

Next, as shown at step 3 of FIG. 52, the tissue sample can be processed for nucleic acid (RNA or DNA) extraction (108). The extracted nucleic acids can undergo processing, e.g., sequencing or gene chip analysis (110) to generate quantified gene expression data, i.e., input data (116), to be entered into the classifier (118).

Processing of the extracted nucleic acids may be by methods known in the art. In one embodiment, the nucleic acids are RNA extracted from the tissue sample and converting to a cDNA library that is analyzed by sequencing (110-112). Briefly, RNA seq analysis involves isolating or extracting RNA from a sample, and generating a cDNA including sequencing adaptors. The RNA or cDNA produced can be fragmented into similarly sized pieces to increase the sequencing efficiency. The cDNA library is then sequenced to produce short-read sequences that are then aligned with a reference genome. The level of gene expression can be quantified, and alternative splicing and non-coding RNA (such as microRNA) can be identified (See, e.g., Chaussabel et al., 2010).

In another embodiment, the nucleic acids are RNA or DNA which are hybridized to a gene chip (114) for analysis by methods known in the art. Particularly, the sample may be analyzed using a gene chip specific to one or more of the markers found in Table 4, preferably 20 or more markers, 30, 40, 50, 60, 70, 80, 90, 100, 110, 120, 121 of the markers found in Table 4. Suitable gene chips include a detection probe specific to the markers found in Table 4 linked to a solid support that can then be analyzed. Gene chip analysis methods are known in the art.

Quantified data obtained by the method (116) can then be used as input data for the classifier (118). At the classification step of FIG. 52, a computer 200 (e.g., computer system 202 in FIG. 53) can be used to associate a signature of the one or more biomarker expression with a disease state (106 e.g., HPD or not). For example, analysis of biomarker gene expression 116 (e.g. input data) of at least two states (e.g., HPD or non-HPD), can be conducted with a classifier system (118) comprising a computer system 200 to generate an association between the disease state 106 and the gene signature (e.g., biomarker expression profile). The generation of signature can be by an association analysis or statistical classification using methods known in the art, including, but not limited to, a wide variety of supervised and unsupervised data analysis and clustering approaches such as hierarchical cluster analysis (HCA), principal component analysis (PCA), Partial least squares Discriminant Analysis (PLS-DA), machine learning (also known as random forest), logistic regression, decision trees, support vector machine (SVM), k-nearest neighbors, naive bayes, linear regression, polynomial regression, SVM for regression, K-means clustering, and hidden Markov models, among others. In other words, the gene expression between the HPD and non-HPD are compared/analyzed (e.g. using a computer 202) with each other to determine with statistical significance what patterns can distinguish between the two disease states (e.g., HPD and non-HPD) after treatment with anti-PD-1 therapy.

The classifier system (118), a biomarker classifier signature is constructed based on statistically significant correlations. In an embodiment, computing system 200 constructs the biomarker classifier signature. In an embodiment, one or more users supervises and informs construction of the biomarker classifier signature. The biomarker classifier can be configured to stratify a population into a plurality of subpopulations. For example, the biomarker classifier can be applied to each patient's test information to determine a sub-population to which the patient belongs, e.g., prognosis, likelihood of developing HPD, etc. The biomarker classifier may be created using one or more of the following techniques, for example, using a statistical method, such as the Sequence Kernel Association Test (SKAT). Alternatively or additionally, the classifier can be created using a clustering method such as k-means or hierarchical clustering. These techniques may be applied at the variant and/or gene level to identify statistically significant associations between genetic changes and observed phenotype. These techniques can be used to source phenotypic and genotypic information from multiple users across multiple datasets and populations. For samples that have the appropriate consent, the system can identify genotype-to-phenotype associations that are statistically significant in a meta-analysis performed across multiple studies performed by multiple users.

Computer Control Systems

The present disclosure provides systems that are programmed to implement methods of the disclosure. FIG. 53 shows a computer system 200 that is programmed or otherwise configured to classify HPD and non-HPD (118) This determination, analysis or statistical classification is done by methods known in the art, including, but not limited to, for example, a wide variety of supervised and unsupervised data analysis and clustering approaches such as hierarchical cluster analysis (HCA), principal component analysis (PCA), Partial least squares Discriminant Analysis (PLS-DA), machine learning (also known as random forest), logistic regression, decision trees, support vector machine (SVM), k-nearest neighbors, naive bayes, linear regression, polynomial regression, SVM for regression, K-means clustering, and hidden Markov models, among others. The computer system 200 can perform various aspects of analyzing the gene expression data (input data) of the present disclosure, such as, for example, comparing/analyzing the disease state. The computer system can be used for running the classifiers to detect and discriminate different disease states (e.g., HPD vs. non-HPD). Data collected can be used to train a machine learning algorithm, specifically an algorithm that receives array measurements from a patient. Before training the algorithm, raw data from the array can be first denoised to reduce variability in individual variables.

Generally, machine learning algorithms are used to construct models that accurately assign class labels to examples based on the input features that describe the example. In some case it may be advantageous to employ machine learning and/or deep learning approaches for the methods described herein. Further, machine learning can be understood as the ability of a learning machine to perform accurately on new, unseen examples/tasks after having experienced a learning data set. Machine learning may include the following concepts and methods. Supervised learning concepts may include AODE; Artificial neural network, such as Backpropagation, Autoencoders, Hopfield networks, Boltzmann machines, Restricted Boltzmann Machines, and Spiking neural networks; Bayesian statistics, such as Bayesian network and Bayesian knowledge base; Case-based reasoning; Gaussian process regression; Gene expression programming; Group method of data handling (GMDH); Inductive logic programming; Instance-based learning; Lazy learning; Learning Automata; Learning Vector Quantization; Logistic Model Tree; Minimum message length (decision trees, decision graphs, etc.), such as Nearest Neighbor Algorithm and Analogical modeling; Probably approximately correct learning (PAC) learning; Ripple down rules, a knowledge acquisition methodology; Symbolic machine learning algorithms; Support vector machines; Random Forests; Ensembles of classifiers, such as Bootstrap aggregating (bagging) and Boosting (meta-algorithm); Ordinal classification; Information fuzzy networks (IFN); Conditional Random Field; ANOVA; Linear classifiers, such as Fisher's linear discriminant, Linear regression, Logistic regression, Multinomial logistic regression, Naive Bayes classifier, Perceptron, Support vector machines; Quadratic classifiers; k-nearest neighbor; Boosting; Decision trees, such as C4.5, Random forests, ID3, CART, SLIQ, SPRINT; Bayesian networks, such as Naive Bayes; and Hidden Markov models. Unsupervised learning concepts may include; Expectation-maximization algorithm; Vector Quantization; Generative topographic map; Information bottleneck method; Artificial neural network, such as Self-organizing map; Association rule learning, such as, Apriori algorithm, Eclat algorithm, and FP-growth algorithm; Hierarchical clustering, such as Single-linkage clustering and Conceptual clustering; Cluster analysis, such as, K-means algorithm, Fuzzy clustering, DBSCAN, and OPTICS algorithm; and Outlier Detection, such as Local Outlier Factor. Semi-supervised learning concepts may include; Generative models; Low-density separation; Graph-based methods; and Co-training. Reinforcement learning concepts may include; Temporal difference learning; Q-learning; Learning Automata; and SARSA. Deep learning concepts may include; Deep belief networks; Deep Boltzmann machines; Deep Convolutional neural networks; Deep Recurrent neural networks; and Hierarchical temporal memory.

The computer system 200 depicted in FIG. 54 is adapted to implement a method described herein. The system 200 includes a central computer server 202 that is programmed to implement exemplary methods described herein. The server 202 includes a central processing unit (CPU, also "processor") 204 which can be a single core processor, a multi core processor, or plurality of processors for parallel processing. The server 202 also includes memory 210 (e.g., random access memory, read-only memory, flash memory); electronic storage unit 215 (e.g. hard disk); communications interface 220 (e.g., network adaptor) for communicating with one or more other systems; and peripheral devices 225 which may include cache, other memory, data storage, and/or electronic display adaptors. The memory 210, storage unit 215, interface 220, and peripheral devices 225 are in communication with the processor 205 through a communications bus (solid lines), such as a motherboard. The storage unit 215 can be a data storage unit for storing data. The server 202 is operatively coupled to a computer network ("network") 230 with the aid of the communications interface 220. The network 230 can be the Internet, an intranet and/or an extranet, an intranet and/or extranet that is in communication with the Internet, a telecommunication or data network. The network 230 in some cases, with the aid of the server 101, can implement a peer-to-peer network, which may enable devices coupled to the server 202 to behave as a client or a server.

The storage unit 215 can store files, such as output reports, and/or communications with the data about samples, or any aspect of data associated with the present disclosure.

The computer server 202 can communicate with one or more remote computer systems through the network 230. The one or more remote computer systems may be, for example, personal computers, laptops, tablets, telephones, Smart phones, or personal digital assistants.

In some applications the computer system 200 includes a single server 202. In other situations, the system includes multiple servers in communication with one another through an intranet, extranet and/or the internet.

The server 202 can be adapted to store measurement data or a database as provided herein, patient information from the subject, such as, for example, medical history, family history, demographic data and/or other clinical or personal information of potential relevance to a particular application. Such information can be stored on the storage unit 215 or the server 202 and such data can be transmitted through a network.

Methods as described herein can be implemented by way of machine (or computer processor) executable code (or software) stored on an electronic storage location of the server 202, such as, for example, on the memory 210, or electronic storage unit 215. During use, the code can be executed by the processor 205. In some cases, the code can be retrieved from the storage unit 215 and stored on the memory 210 for ready access by the processor 205. In some situations, the electronic storage unit 215 can be precluded, and machine-executable instructions are stored on memory 210. Alternatively, the code can be executed on a second computer system 240.

Aspects of the systems and methods provided herein, such as the server 202, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical, and electromagnetic waves, such as used across physical interfaces between local devices, through wired and optical landline networks and over various air-links. The physical elements that carry such waves, such as wired or wireless likes, optical links, or the like, also may be considered as media bearing the software. As used herein, unless restricted to non-transitory, tangible "storage" media, terms such as computer or machine "readable medium" can refer to any medium that participates in providing instructions to a processor for execution.

The computer systems described herein may comprise computer-executable code for performing any of the algorithms or algorithms-based methods described herein. In some applications the algorithms described herein will make use of a memory unit that is comprised of at least one database.

Data relating to the present disclosure can be transmitted over a network or connections for reception and/or review by a receiver. The receiver can be but is not limited to the subject to whom the report pertains; or to a caregiver thereof, e.g., a health care provider, manager, other health care professional, or other caretaker; a person or entity that performed and/or ordered the analysis. The receiver can also be a local or remote system for storing such reports (e.g. servers or other systems of a "cloud computing" architecture). In one embodiment, a computer-readable medium includes a medium suitable for transmission of a result of an analysis of a biological sample using the methods described herein.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

Kits of the Present Invention

In one embodiment, the present invention is a kit comprising probes for at least one of the marker sets above for the prognosis of cancer patients who are more likely to develop HPD if they are subjected to immunotherapy such as anti-PD-1 treatment. The analytical methods in above sections can be implemented with software package R. The software package R can be freely downloaded from the website.

We expected that convenient devices for diagnostic testing could include manufactured microarray chips containing the probe sets for our identified biomarkers to measure the gene expression changes of these biomarkers predictive of HPD occurrence.

In one embodiment of the invention, the probe set would contain diagnostic probes for at least 5, 10, 15, 20, 25, 30, 35, 40, 45, 50, 55, 60, 65, 70, 75, 80, 85, 90, 95, 100, 105, or 110 members of the subset. In one embodiment, the probe set would comprise probes for all 121 members.

In another embodiment, the disclosure provides a kit for detecting the likelihood of a subject for developing HPD, the kit comprising a panel of 121-biomarker probes specific for the 121 biomarkers in Table 4 attached to a solid surface and an instructions for use. Suitable biomarker probes are known in the art, and include, but are not limited to, for example, oligonucleotide sequences, cDNA or small fragments of PCR products that correspond to mRNAs. Suitable solid surfaces are known in the art and include, chips, glass slides, polymer or plastic surfaces, plates, wells within a surface, tubes, and the like. Suitable array surfaces are known and understood in the art. In a further embodiment, the kit further comprises a classifier and a computer system in order to analyze the results of the panel.

In another embodiment, the disclosure provides a system for processing a test sample to determine a likelihood that a patient develops hyperprogesssive disease (HPD) in response to anti-PD-1 immunotherapy in a patient, comprising: (a) a computer capable of receiving input data of the expression of a plurality of biomarker levels, (b) a classifier configured to predict likelihood that a patient develops hyperprogesssive disease in response to anti-PD-1 immunotherapy to classify the test sample, and (c) an output report from the classifier that identifies said classification as indicative of the likelihood that the patient develops hyperprogesssive disease in response to anti-PD-1 immunotherapy. In some embodiments, the kit comprises probes useful to detect the level of at least 10, 20, 30, 40, 50, 60, 70, 80, 90, 100, or 110 of the biomarkers listed in Table 7. In further embodiments, the kit comprises a subset marker probes to those listed in Table 4, and wherein that subset is one of the subsets listed in Table 7, and wherein the tumor type to be tested is of a type listed in Table 7.

In a further embodiment, the present invention provides a gene chip useful for the diagnosis of a HPD positive tumor, wherein the chip comprises probes useful to detect the level of at least 10, 20, 30, 40, 50, 60, 70, 80, 90, 100, or 110 of the biomarkers listed in Table 4. In some embodiments, the gene chip comprises a subset of the Table 4 biomarkers are examined, and wherein that subset is one of the subsets listed in Table 7, and wherein the tumor type to be tested is of a type listed in Table 7.

All publications, patent applications, patents, and other references mentioned herein are incorporated by reference in their entirety. In the case of conflict, the present specification, including definitions, will control.

As used herein, "about" means within 5-10% of a stated concentration range or within 5-10% of a stated number.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. The term "consisting essentially of" and "consisting of" should be interpreted in line with the MPEP and relevant Federal Circuit's interpretation. The transitional phrase "consisting essentially of" limits the scope of a claim to the specified materials or steps "and those that do not materially affect the basic and novel characteristic(s)" of the claimed invention. "Consisting of" is a closed term that excludes any element, step or ingredient not specified in the claim. The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

The present invention has been described in terms of one or more preferred embodiments, and it should be appreciated that many equivalents, alternatives, variations, and modifications, aside from those expressly stated, are possible and within the scope of the invention.

The following Examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

Example 1: Immunogenomic Landscape Contributes to Hyperprogressive Disease after Anti-PD-1 Immunotherapy for Cancer This Example demonstrates a gene expression signature predictive of HPD. Although PD-1-blocking immunotherapies demonstrate significant therapeutic promise, a subset of the patients develop hyperprogressive disease (HPD) with accelerated tumor growth after anti-PD1 immunotherapy. To elucidate the underlying mechanisms, we compared the mutational and transcriptional landscapes between the pre- and post-therapy tumors of two patients developing HPD after anti-PD-1 immunotherapy. In post-therapy HPD tumors, somatic mutations were found in known cancer genes, including tumor suppressor genes such as TSC2 and VHL, along with transcriptional upregulation of oncogenic pathways, including IGF-1, ERK/MAPK, PI3K/AKT, and TGF-3. We found that post-therapy HPD tumors were less immunogenic than pre-therapy tumors, concurrent with an increased presence of ILC3 cells, a subset of innate lymphoid cells. The inventors identified the genomics and immune features associated with HPD, which may help identify patients at risk of adverse clinical outcome after anti-PD-1 immunotherapy.

Experimental Results

Mutation Patterns are Altered in HPD Tumors after Anti-PD-1 Treatment

This study included two patients who received anti-PD-1 blockade immunotherapy. Relevant characteristics of the four FFPE tumor samples are summarized in Table 1. Paired tumor samples before and after anti-PD-1 treatment were obtained from a male patient with esophageal squamous cell carcinoma metastatic to lymph nodes (Patient 1) and from a female patient with clear cell renal cell cancer (ccRCC) that had metastasized to the bone (shoulder) and pleura (Patient 2). Following anti-PD-1 treatment that consisted of pembrolizumab (Merck), these two patients demonstrated HPD, as defined by the accelerated tumor growth rate and clinical deterioration using existing criteria (Kato et al., 2017). Each patient demonstrated progression at first radiologic evaluation (less than 2 months after anti-PD-1 therapy initiation). Before enrollment, written informed consent was obtained from all patients to use their tumor samples for research purposes. The study was approved by the Medical College of Wisconsin Institutional Review Board in accordance with federal regulations.

TABLE 1

Characteristics of the Four FFPE Specimens from Two Patients, Consisting of Paired Pre- and Post-anti-PD-1 (Pembrolizumab) Treatment Samples

| Patient | Gender | Specimen | Cancer | Treatment | Other Clinical Phenotype | % Tumor |
|---------|--------|----------|--------|-----------|--------------------------|---------|
| #1 | Male | S1624794 | Esophageal squamous cell carcinoma | Pre-anti-PD-1 | Metastatic to lymph node | 75 |
|  |  | S1707359 | Esophageal squamous cell carcinoma | Post-anti-PD-1 | Metastatic to lymph node | 75 |

TABLE 1-continued

Characteristics of the Four FFPE Specimens from Two Patients, Consisting of Paired Pre- and Post-anti-PD-1 (Pembrolizumab) Treatment Samples

| Patient | Gender | Specimen | Cancer | Treatment | Other Clinical Phenotype | % Tumor |
|---------|--------|----------|--------|-----------|--------------------------|---------|
| #2 | Female | M16248 | Clear cell renal cell carcinoma | Pre-anti-PD-1 | Metastatic to the pleura and shoulder | 50 |
|  |  | S1701860 | Clear cell renal cell carcinoma | Post-anti-PD-1 | Metastatic to the pleura and shoulder | 75 |

Figure 1:
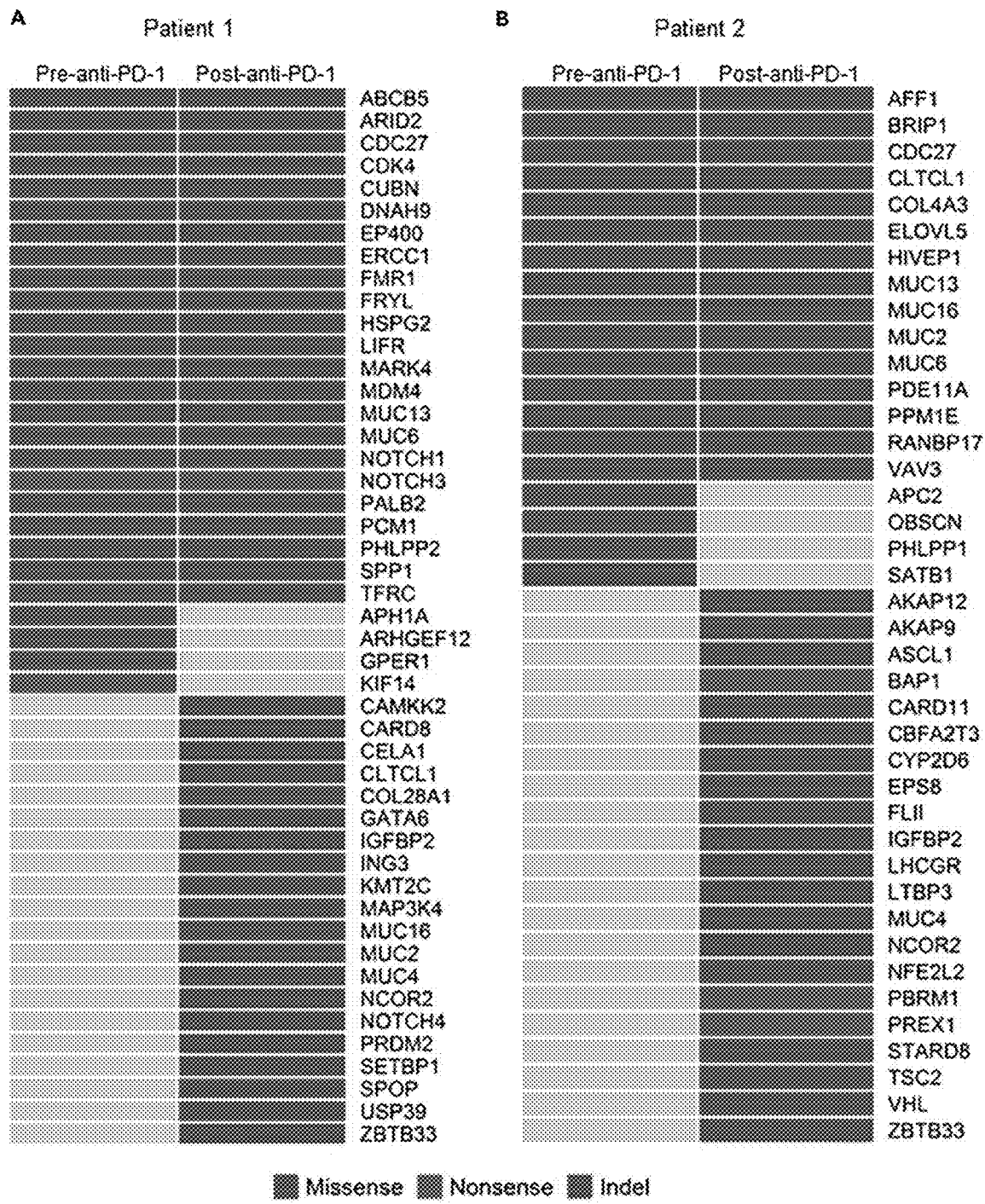
FIG. 1: Profiles of Mutated Cancer Genes (Nonsilent Somatic Mutations) in the Pre- and Post-anti-PD-1 Treatment Tumor Samples. (A) Mutation pattern of Patient 1. (B) Mutation pattern of Patient 2. Indel: insertions or deletions. See also FIG. 10, Tables S1 and S2.
Figure 10:
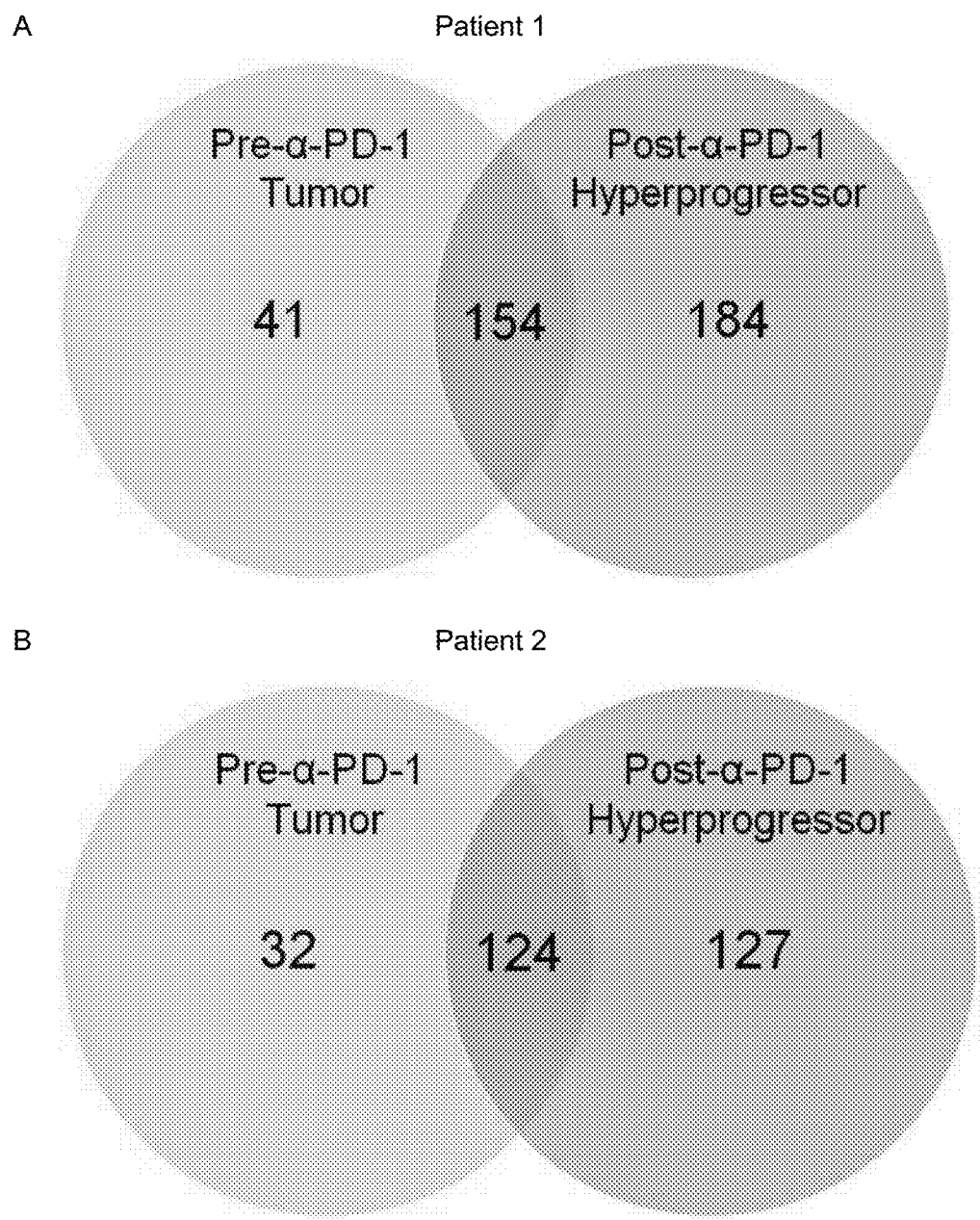
FIG. 10. The number of somatic mutations in the pre- and post-anti-PD-1 treatment tumor samples of the two patients. Related to FIG. 1 and FIG. 2. A) Patient 1; B) Patient 2.

To understand the global changes that take place in HPD tumors after treatment with anti-PD-1, we performed mutational analysis on tumors obtained before and after treatment with pembrolizumab. We observed that Patient 1 had 195 somatic mutations before anti-PD-1 treatment and 338 somatic mutations after treatment; Patient 2 had 156 somatic mutations before treatment and 251 somatic mutations after treatment (Table S1, incorporated by reference in its entirety from U.S. Provisional Application No. 62/914,652). There were 154 and 124 common somatic mutations shared by the HPD and pre-therapy tumors for Patients 1 and 2, respectively (FIG. 10). Our results were in line with another group's results showing increased tumor mutation load from baseline in PD (progressive disease) in patients with melanoma after anti-PD-1 therapy (nivolumab) initiation (Riaz et al., 2017). In the latter, the tumor mutation load was decreased in the responding patients (complete response/partial response) from baseline since nivolumab initiation, consistent with immunoediting (Riaz et al., 2017). We also analyzed the mutation profiles of these two patients in the context of known cancer genes based on a comprehensive list of cancer-related genes downloaded from the Bushman Lab Gene Lists website. There were 47 cancer genes mutated in at least one of the tumors from Patient 1 and 40 cancer genes mutated in at least one of the tumors from Patient 2 (FIG. 1, Table S2, incorporated by reference in its entirety from U.S. Provisional Application No. 62/914,652). Four cancer genes (APH1A, ARHGEF12, GPER1, and KIF14) mutated in the pre-therapy tumor of Patient 1 were not mutated in the HPD tumors, suggesting that the tumor clones containing these four cancer genes were eliminated by anti-PD-1 treatment. However, the HPD tumor of Patient 1 had somatic mutations in 20 cancer genes, including IGFBP2, KMT2C, MAP3K4, MUC16, MUC2, NCOR2, and NOTCH4, which were not present in the pre-therapy tumors. Similar patterns were also observed for Patient 2. Four cancer genes (APC2, OBSCN, PHLPP1, and SATB1) that were mutated in the pre-therapy tumor of Patient 2 were not mutated in the post-treatment tumors, whereas the HPD tumor of Patient 2 had somatic mutations in 21 cancer genes, including IGFBP2, MUC4, NCOR2, NFE2L2, TSC2, and VHL, which were not present in the pre-therapy tumors. The identified mutations in these genes were not present in the tumors of non-HPD patients after anti-PD-1 treatment when compared with previous studies (Biton et al., 2018, Gong et al., 2017, Hanna et al., 2018, Hugo et al., 2016, Miao et al., 2018, Riaz et al., 2017, Rizvi et al., 2015, Teo et al., 2018, Yoshikawa et al., 2017, Zaretsky et al., 2016). These data indicate that the mutational landscape of tumors was significantly altered after anti-PD-1 therapy in patients who demonstrated hyperprogression after anti-PD-1 treatment.

Figure 11:
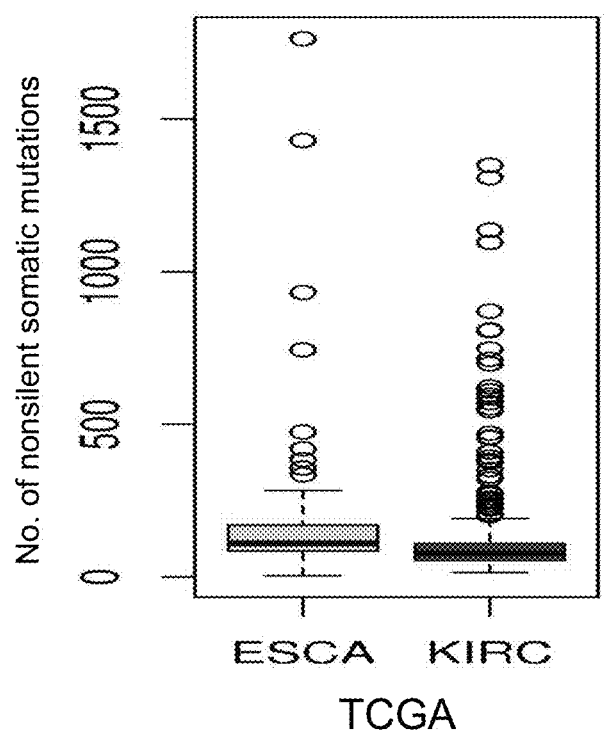
FIG. 11 The distribution of nonsilent somatic mutations in the two TCGA cancer types analyzed in the hyperprogressive tumor context in the present study. Related to FIG. 1 and FIG. 2. The numbers of nonsilent somatic mutations of the esophageal carcinoma (ESCA, n=184) and kidney renal clear cell carcinoma (KIRC, n=384) samples from TCGA.

For comparison in the context of corresponding cancer populations, we analyzed the numbers of somatic mutations of the esophageal carcinoma (ESCA, n=184) and kidney renal clear cell carcinoma (KIRC, n=384) samples from The Cancer Genome Atlas (TCGA). The numbers of nonsilent somatic mutations were in the range of 4-1,763 for ESCA and 15-1,349 for KIRC. The lower quartile, median, and upper quartile were 85, 110, and 168 for ESCA and 54, 77, and 109 for KIRC, respectively (FIG. 11). The numbers of nonsilent somatic mutations in the before and after anti-PD-1 therapy tumors of the two HPD patients in this study were 195 and 338 for the patient with ESCA and 156 and 251 for the patient with KIRC. Therefore, they were all above the upper quartiles of TCGA ESCA and KIRC datasets, which suggested that these two patients have an exceptionally high number of somatic mutations compared with the TCGA esophageal cancer (ESCA) and ccRCC (KIRC).

Figure 2:
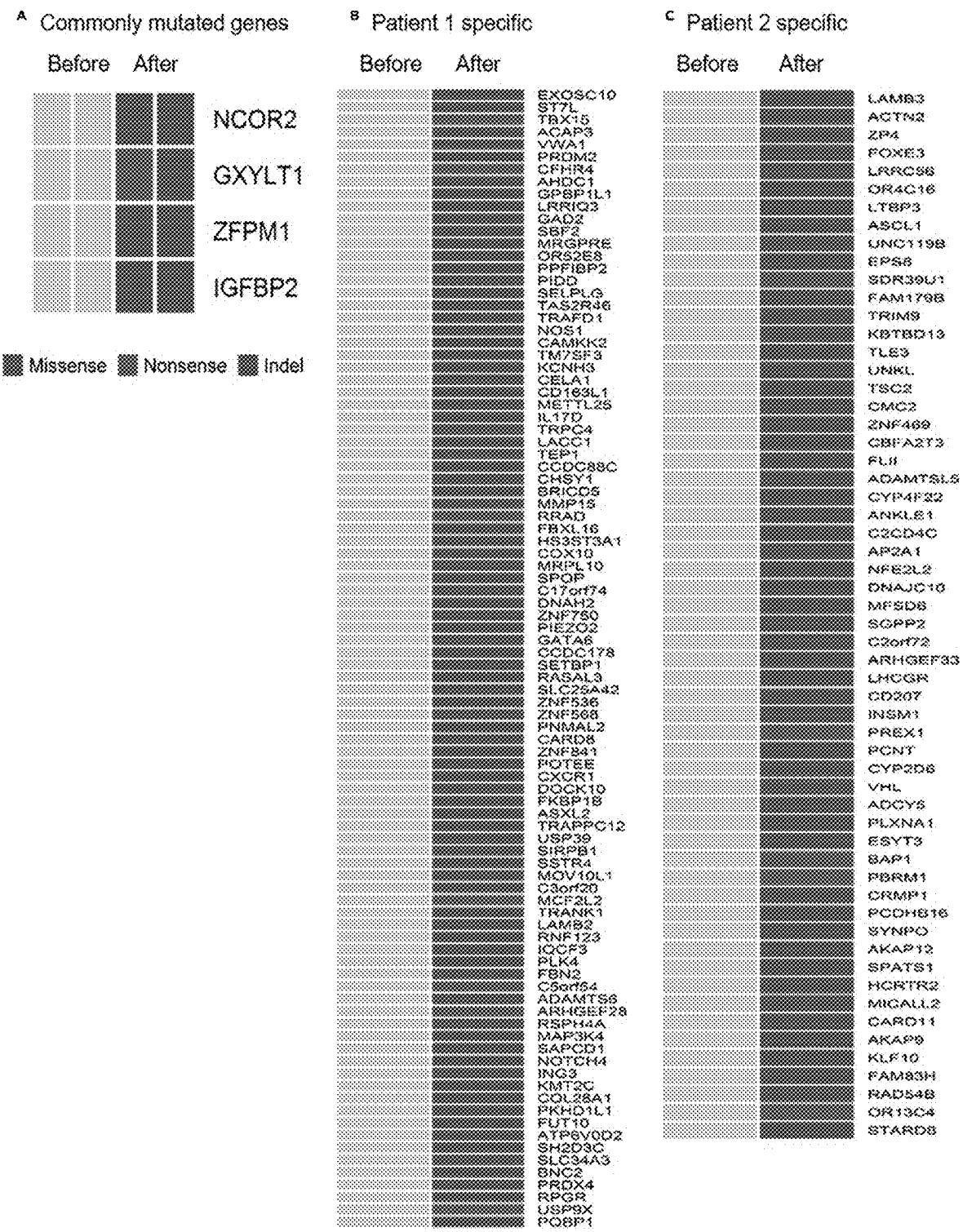
FIG. 2. Mutation Signatures of Post-anti-PD-1 Treatment Hyperprogressor Tumors. (A-C) (A) Commonly mutated genes in the two hyperprogressor tumors, (B) specific mutated genes in Patient 1's hyperprogressor tumor, and (C) specific mutated genes in Patient 2's hyperprogressor tumor. See also FIG. 10, Tables S1 and S3.

HPD Tumors Contain Deleterious Mutations and Significantly Activated Oncogenic Signaling Pathways To determine if certain genes were altered in both patients with HPD tumors, we searched for gene mutations that were common for the HPD tumors of both patients. Four genes were mutated in the post-treatment tumors of both patients: NCOR2, GXYLT1, ZFPM1, and IGFBP2 (FIG. 2A). There were 96 and 64 subject-specific nonsilent somatic mutations from 154 genes in post-treatment tumors of Patients 1 and 2, respectively (FIGS. 2B and 2C). The detailed information of these mutations are given in Table S3, incorporated by reference in its entirety from U.S. Provisional Application No. 62/914,652.

Figure 12:
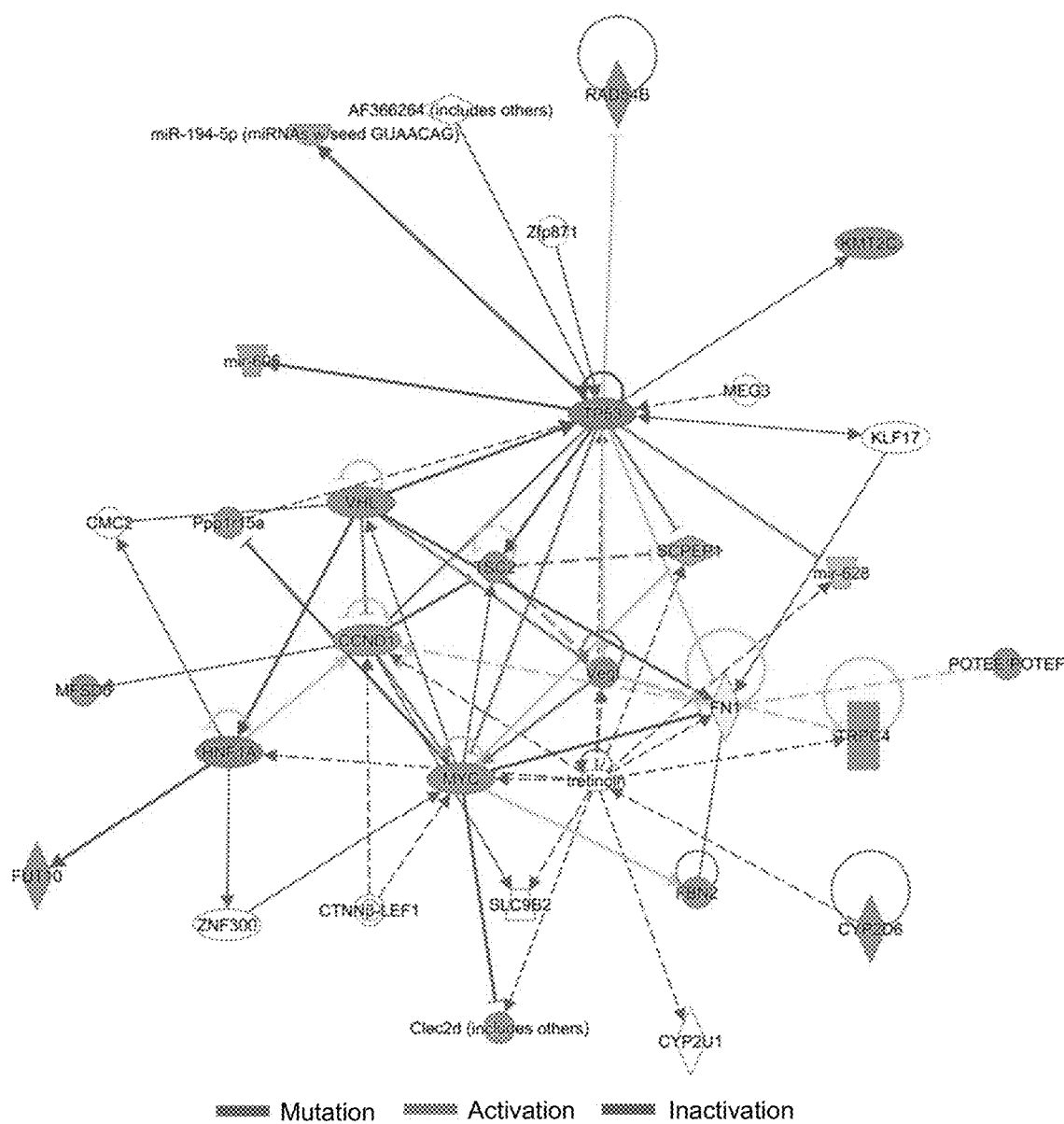
FIG. 12 Key mutated cancer genes interacting network. Related to Table 2. Based on the eleven genes with the deleterious somatic mutations, a mechanistic network was built by IPA in which ten genes carrying these mutations resulted in the suppression of TP53 tumor suppressor pathway and activation of MYC, CCND1 and VEGF oncogenic pathways.

Bioinformatics analyses of these 161 mutations led to the identification of 11 potentially deleterious somatic variants in the HPD tumors, which were predicted to be "deleterious" by SIFT, "probably damaging" by PolyPhen-2, and "potentially associated with cancer" by FATHMM (Table 2). The 11 genes having these deleterious mutations were TRPC4, POTEE, FBN2, KMT2C, FUT10, PQBP1, TSC2, MFSD6, CYP2D6, VHL, and RAD54B. Of the 11 mutations, 10 were located at evolutionarily conserved sites, as predicted by GERP++ (scores >2; Table 2). IPA (Ingenuity Pathway Analysis, Qiagen Inc., MD, USA), based on the 11 genes with the deleterious somatic mutations, identified a network involving these mutated genes that contributes to suppression of the TP53 tumor suppressor and activation of MYC, CCND1, and VEGF oncogenes (FIG. 12). The mutated TSC2 gene carrying a missense mutation, p.Y1611S, was in the center of this network and is linked to inhibition of the TP53 pathway and activation of the MYC, CCND1, and VEGF pathways (FIG. 12). TSC2 (also known as TUBERIN) is a tumor suppressor that negatively regulates cellular signaling networks that control cellular growth and proliferation (Dang et al., 2017). The MuPIT interactive protein mutation analysis (Niknafs et al., 2013) showed that the pY1611S mutation is located in the Rap/ran-GAP domain of the TSC2 protein, which is critical for the 3-kinase (PI3K)/AKT, and transforming growth factor (TGF)-β signaling pathways. A large number of genes in these oncogenic pathways were upregulated in the HPD tumors (FIG. 3B). Such concerted gene expression changes may synergistically contribute to the generation of the HPD tumors after anti-PD-1 immunotherapy.

TABLE 2

Characteristics of the 11 Deleterious Somatic Mutatations in the HPD Tumors after Anti-PD-1 Treatment

| | | | | | Predicted Effect of Somatic Mutation | | | | | |
|---|---|---|---|---|---|---|---|---|---|---|
| Gene | Genomic Position$^a$ | Genomic Mutation | Exon | Protein Alteration | SIFT$^b$ | Poly-Phen-2$^c$ | FATHMM$^d$ | GERP ++$^e$ | snp 137 | ESP MAF$^f$ |
| TRPC4 | chr13: 38211734 | c.G2045A | 10 | p.R682H | Deleterious (0.00) | Probably damaging (0.999) | Potentially associated with cancer (−2.83) | 6.06 | NA | NA |
| POTEE | chr2: 132021334 | c.A2306T | 15 | p.Y769F | Deleterious (0.00) | Probably damaging (0.997) | Potentially associated with cancer (−4.69) | NA | NA | NA |
| FBN2 | chr5: 127666313 | c.C4297T | 33 | p.R1433C | Deleterious (0.00) | Probably damaging (0.983) | Potentially associated with cancer (−2.9) | 4.21 | NA | 7.70 × 10$^{-5}$ |
| KMT2C | chr7: 151932981 | c.G2690C | 16 | p.R897P | Deleterious (0.00) | Probably damaging (0.995) | Potentially associated with cancer (−2.21) | 5.1 | NA | NA |
| FUT10 | chr8: 33246817 | c.G876T | 4 | p.K292N | Deleterious (0.00) | Probably damaging (1.00) | Potentially associated with cancer (−4.75) | 3.42 | NA | NA |
| PQBP1 | chrX: 48759773 | c.C256T | 4 | p.P86S | Deleterious (0.00) | Probably damaging (0.996) | Potentially associated with cancer (−1.13) | 5.02 | NA | NA |
| TSC2 | chr16: 2137907 | c.A4832C | 37 | p.Y1611S | Deleterious (0.02) | Probably damaging (0.997) | Potentially associated with cancer (−3.16) | 4.59 | NA | NA |
| MFSD6 | chr2: 191301728 | c.G973A | 3 | p.G325R | Deleterious (0.00) | Probably damaging (0.998) | Potentially associated with cancer (−2.42) | 6.07 | NA | NA |
| CYP2D6 | chr22: 42522990 | c.C1025T | 7 | p.T342M | Deleterious (0.00) | Probably damaging (0.996) | Potentially associated with cancer (−2.26) | 4.06 | NA | NA |
| VHL | chr3: 10191479 | c.C349G | 2 | p.L117V | Deleterious (0.00) | Probably damaging (0.994) | Potentially associated with cancer (−6.95) | 3.07 | NA | NA |
| RAD54B | chr8: 95411747 | c.T721G | 6 | p.F241V | Deleterious (0.01) | Probably damaging (0.996) | Potentially associated with cancer (−3.01) | 5.55 | NA | NA |

Figure 13:
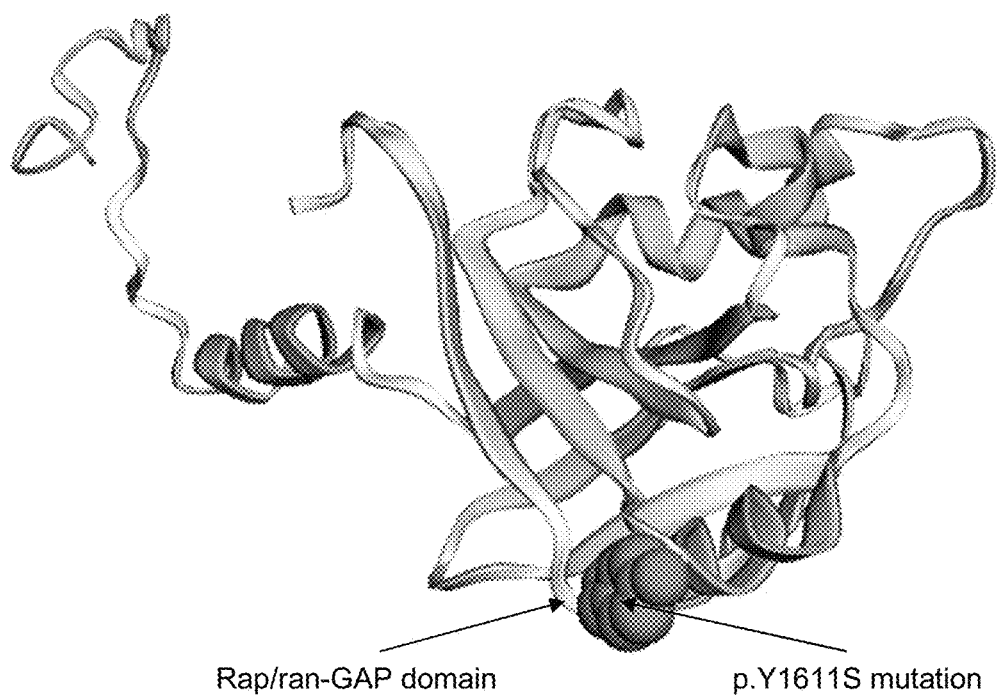
FIG. 13 Key mutation in the TSC2 protein. Related to Table 2. The 3D structure of the TSC2 protein and the location of the amino acid residue harboring the p.Y1611S mutation, which is within the Rap/ran-GAP domain of the TSC2 protein critical to its biological function.

ESP; NHLBI Exome Sequencing Project; NA, not available. See also FIG. S3.
$^a$Genomic positions are given according to the UCSC Genome Browser hg 19 reference assembly.
$^b$SIFT scores range from 0 to 1. The amino acid substitution is predicted to be damaging if the score is ≤0.05 and tolerated if the score is ≥0.05.
$^c$PolyPhen-2 scores 0.85-1 are interpreted as probably damaging, scores 0.2-0.85 are possibly damaging, and sores 0-0.2 are benign.
$^d$Predictons with FATHMM scores less than 0.75 indicate that the mutation is potentially associated with cancer; otherwise the mutaton is not associated with cancer.
$^e$There is an indication of evolutionary conservation if a given site shows a GERP++ score >2.
$^f$MAFs are according to the NHLBI GO Exome Sequencing Project (ESP6500SI-V2 release) Exome Variant Server v.0.0.21(August 2013).

biological function of TSC2 (FIG. 13). Previous studies showed that TSC2 knockdown transforms mouse and human renal epithelial cells into neoplastic stem cells that can serially propagate upon re-inoculation in mice (Dang et al., 2017). Together, it is reasonable to hypothesize that the deleterious p.Y1611S mutation could result in the loss of function of the TSC2 protein, which in turn will lead to uncontrolled proliferation of cancer cells in the HPD tumors that survive anti-PD-1 treatment.

Based on the differentially expressed genes, IPA identified four significantly activated oncogenic signaling pathways in the HPD tumors after anti-PD-1 therapy compared with the pre-therapy tumors (p value <0.01, Z score >2, FIG. 3A). They were the insulin growth factor (IGF)-1, extracellular signal-regulated kinase (ERK)/mitogen-activated protein kinase (MAPK), Phosphatidylinositol-4,5-bisphosphate Clonal Evolution was Detected in HPD Tumors after Anti-PD-1 Therapy The generation of WES data allowed us to quantify the mutant allele frequencies in all cases. Based on mutation clustering results, we inferred the identity of three clones having distinct sets of mutations (clusters) in pre-therapy tumors when compared with post-therapy HPD tumors of the two patients. Multiple mutation clusters (n=3) were present in each of the pre-therapy tumors of the two HPD patients. In Patient 1, the post-anti-PD-1 treatment HPD tumor was associated with the outgrowth of new clone(s) represented by mutations in cancer-associated genes including KMT2C, NCOR2, COL28A1, ING3, CAMKK2, and CARD8 (FIGS. 4A and 4C). The pre-therapy tumor clone(s) characterized by mutations in APH1A, ARHGEF12, GPER1, and KIF14 genes was eliminated by anti-PD-1 treatment (FIGS. 4A and 4C). The clone(s) represented by mutations in the cancer genes EP400, CUBN, SPP1, PHLPP2, PALB2, ERCC1, TFRC, MARK4, and MDM4 remained stable under the selection pressure of anti-PD-1 treatment (FIGS. 4A and 4C). In Patient 2, the post-anti-PD-1 treatment HPD tumor was associated with the evolution of new clone(s) represented by mutations in the cancer genes including BAP1, CARD11, CBFA2T3, CYP2D6, PBRM1, TSC2, and VHL (FIGS. 4B and 4D), whereas the pre-therapy tumor clone with mutations in APC2, CDC27, OBSCN, PHLPP1, and SATB1 was not detectable after anti-PD-1 treatment (FIGS. 4B and 4D). Other clones, including those represented by mutations in COL4A3, TTC40, NPHS1, UGT2A3, RYR1, AGGF1, and LANCL1, remained stable before and after anti-PD-1 treatment (FIGS. 4B and 4D).

Figure 14:
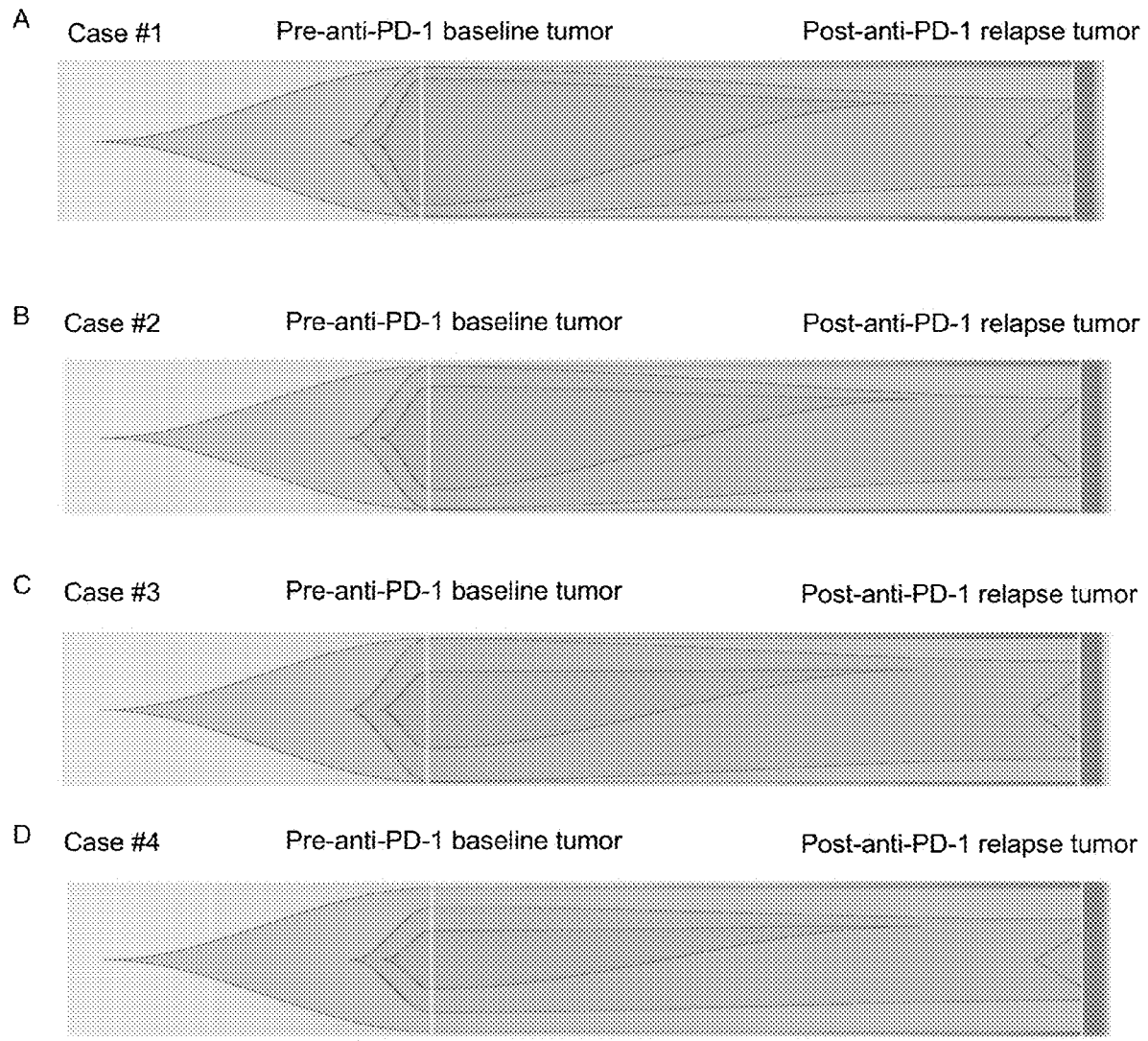
FIG. 14. Clonal evolution from the pre-anti-PD1 therapy baseline tumor to post-anti-PD-1 relapsing tumor in the four melanoma patients from a previous study. Related to FIG. 4. The graphical representation of clonal evolution in the four melanoma patients: (A) Case #1; (B) Case #2; (C) Case #3; (D) Case #4.
Figure 15:
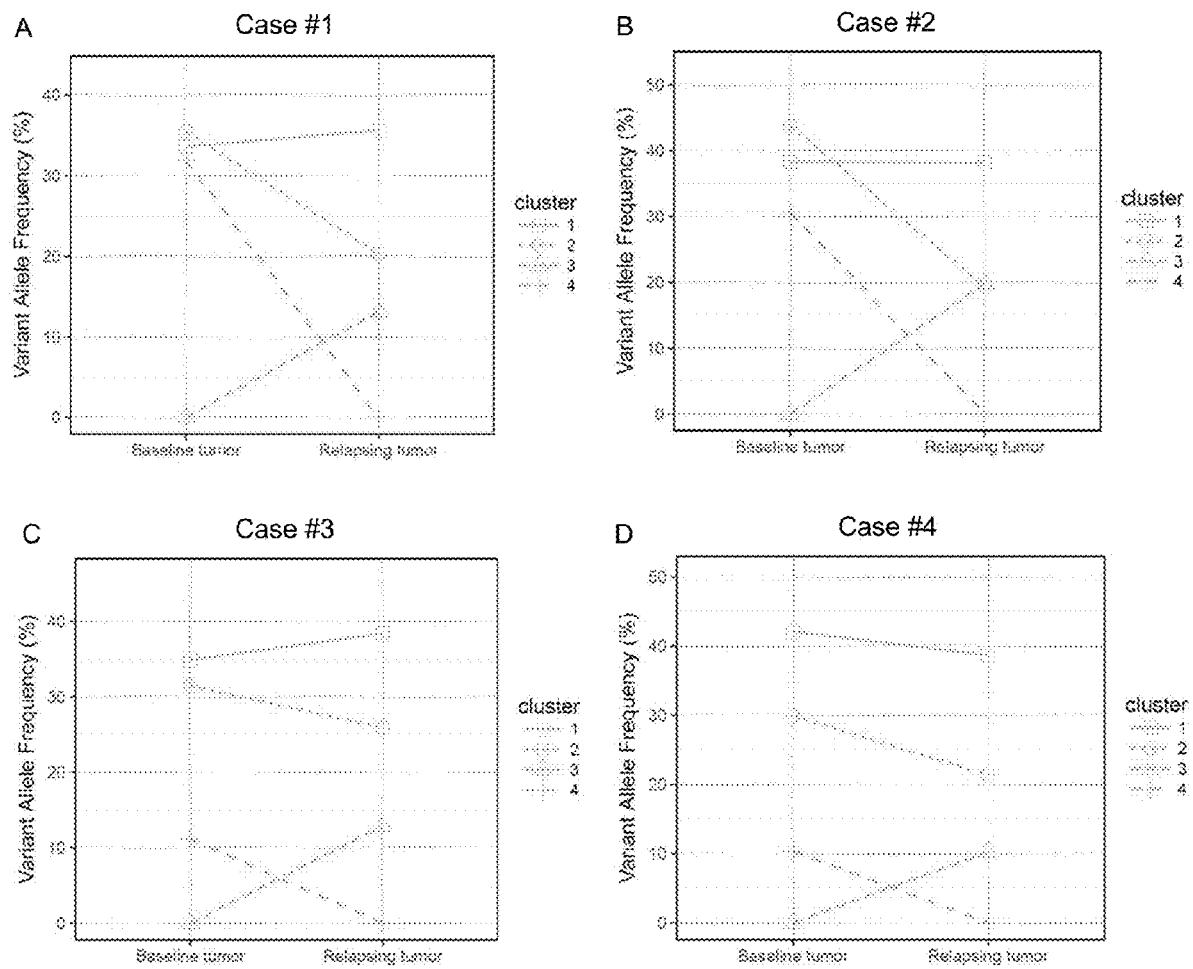
FIG. 15 The mutation clusters representing clonal evolution from the pre-anti-PD1 therapy baseline tumor to post-anti-PD-1 relapsing tumor in the four melanoma patients from a previous study. Related to FIG. 4. The mutation clusters detected in the pre-anti-PD1 therapy baseline tumor to post-anti-PD-1 relapsing tumor in the patients: (A) Case #1; (B) Case #2; (C) Case #3; (D) Case #4. The relationship between the clusters in the pre-therapy and post-therapy tumors are indicated by lines linking them.

The tumor clonal evolution pattern associated with anti-PD-1 treatment was further validated by analyzing an independent dataset from a previous study, which conducted WES of paired baseline and relapsed tumors (before and after anti-PD-1 treatment) of four patients with melanoma (Zaretsky et al., 2016). As can be seen from FIGS. 14 and 15, all four melanoma cases demonstrated allele clusters after anti-PD-1 therapy. Variant allele frequencies (VAFs) of the Cluster 1 mutations were not significantly changed by PD-1 blockade; Cluster 2 mutations had reduced VAFs but were still prevalent in the relapsing tumor after PD-1 blockade; Cluster 3 mutations represented the newly evolved tumor clone(s) in the relapsing tumor after PD-1 blockade; Cluster 4 mutated genes represented the tumor clone(s) that diminished to undetectable levels after PD-1 blockade. These data are consistent with our own analysis of tumors from HPD patients before and after anti-PD-1 therapy.

HPD Tumors Demonstrate Decreased Immunogenicity Relative to Pre-Therapy Tumors

Figure 5:
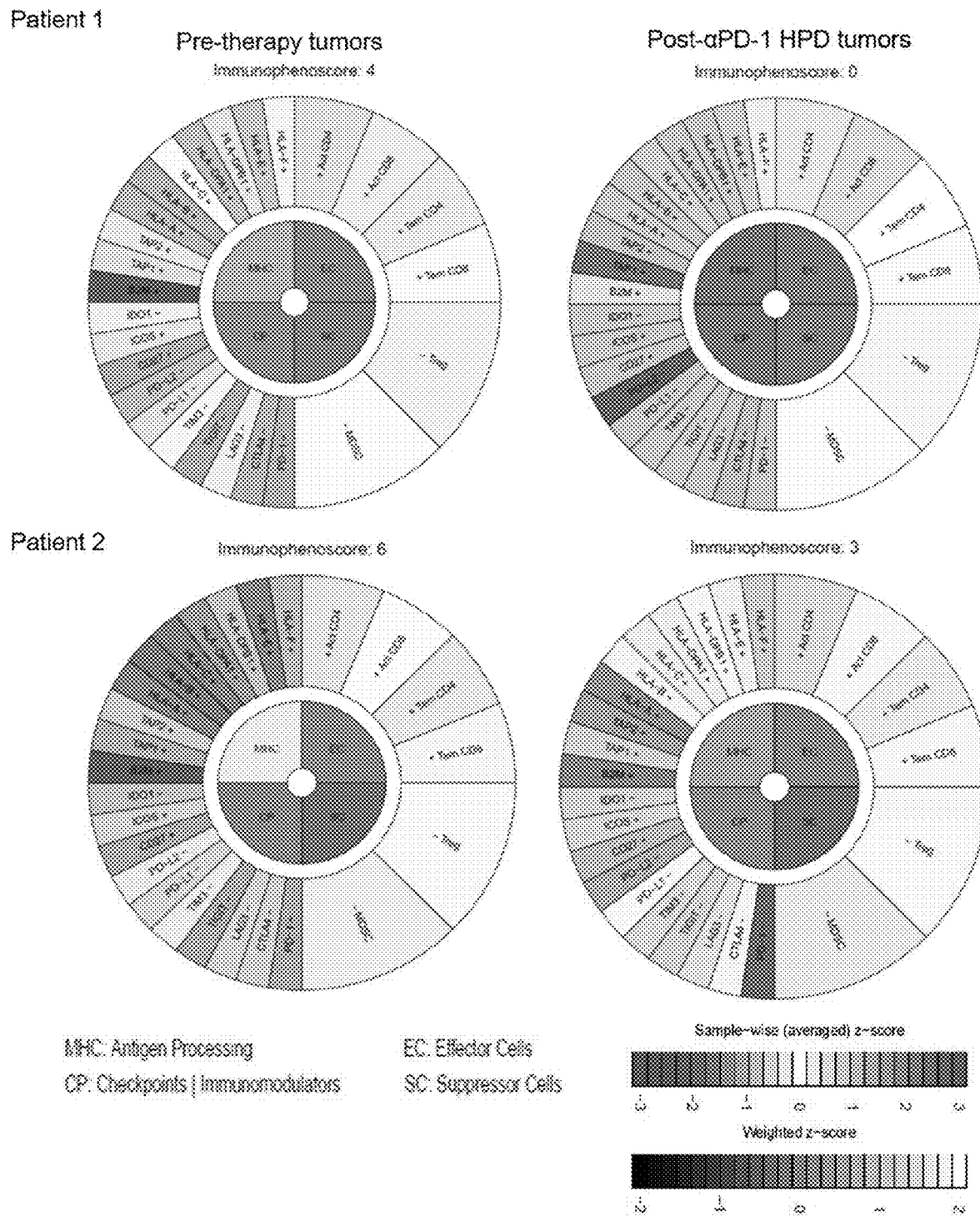
FIG. 5. Immunophenoscores of the Hyperprogressor versus Non-hyperprogressor Tumors of the Two Patients Subject to Anti-PD-1 Immunotherapy. HLAs were downregulated in the HPD tumors compared with the pre-therapy tumors (shown in the upper left quadrant termed MHC), whereas checkpoints were upregulated in the HPD tumors (shown in the lower left quadrant termed CP). These changes resulted in the overall reduction of immunophenoscores in the HPD tumors resistant to anti-PD-1 immunotherapy. See also FIG. 23.

Since anti-PD-1 treatment renders its effects on tumors in a manner completely dependent on immunity, we investigated whether HPD tumors demonstrated changes in their capacity to elicit productive immune reactions using an in silico immunophenogram approach (Charoentong et al., 2017). The results showed that HPD tumors had much smaller immunophenoscores compared with the pre-therapy tumors for both patients (FIG. 5). Expression of HLAs (human leukocyte antigens) was downregulated in the post-therapy HPD tumors compared with the pre-therapy tumors, whereas checkpoint genes were upregulated in the HPD tumors (FIG. 5). These changes resulted in the overall reduction of immunophenoscores in HPD tumors. Consistent with results from the immunophenogram analysis, the differential expression analysis showed that seven genes involved in antigen processing were downregulated in the HPD tumors, i.e., B2M, HLA-B, HLA-DPA1, HLA-DPB1, HLA-DRA, HLA-E, and HLA-F (FIG. 6A). In addition, eight genes encoding immune checkpoints or modulators were upregulated in the HPD tumors, i.e., CTLA4, KDR, CD96, CD70, TNFRSF18, TNFRSF25, BTNL2, and TNFRSF8 (FIG. 6A). Changes in expression of these immune-related genes were likely contributors to the weakened immunogenicity of the HPD tumors.

Immune Cell Signatures in HPD Tumors are Predominantly Immunosuppressive

Previous studies have characterized the signature genes of 28 immune cell populations critical to immune responses across multiple cancers (Angelova et al., 2015, Charoentong et al., 2017). Using GSVA (Gene Set Variation Analysis) (Hanzelmann et al., 2013), we evaluated the immune cell landscape in the HPD tumors from our two patients. We identified that the activities of eight immune cell populations were significantly decreased in the HPD tumors after anti-PD-1 treatment (FIG. 6B). These populations were monocytes, central memory CD4 T cells, immature dendritic cells, CD56dim NK (natural killer) cells, NK cells, gamma-delta (γδ) T cells, activated dendritic cells, and follicular helper T cells, most of which are linked to functional tumor clearance. In addition, the activities of three immune cell populations, i.e., neutrophils, activated B cells, and neutrophil-like myeloid-derived suppressor cells (MDSC), were upregulated in the hyperprogressors (FIG. 6B). These data suggest that the depletion of monocytes, certain types of T cells, NK cells, and dendritic cells may contribute to the ability of HPD tumors to escape immune surveillance. Furthermore, the upregulated neutrophil population as well as the neutrophil-like MDSC (i.e., the MDSC subpopulation with neutrophil signature gene expression) (Zhang et al., 2017) may also contribute to the immune evasion of HPD tumors since these cell populations have been implicated in generating a milieu that attenuates immune responses in the tumor microenvironment (Galdiero et al., 2013, Mishalian et al., 2013, Sagiv et al., 2015, Tuting and de Visser, 2016, Zhang et al., 2017).

ILC3 Innate Lymphocytes are Upregulated in HPD Tumors

Figure 16:
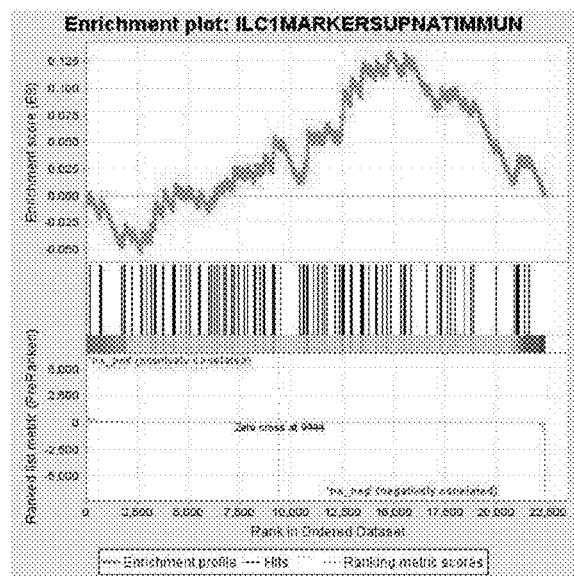
FIG. 16 The ILC1 and ILC2 populations activity do not have significant changes in the HPD tumors after anti-PD-1 therapy. Related to FIG. 7. (A) The ILC1 and (B) the ILC2 marker genes were not enriched in either the top up- or down-regulated genes in the HPD tumors.
Figure 16:
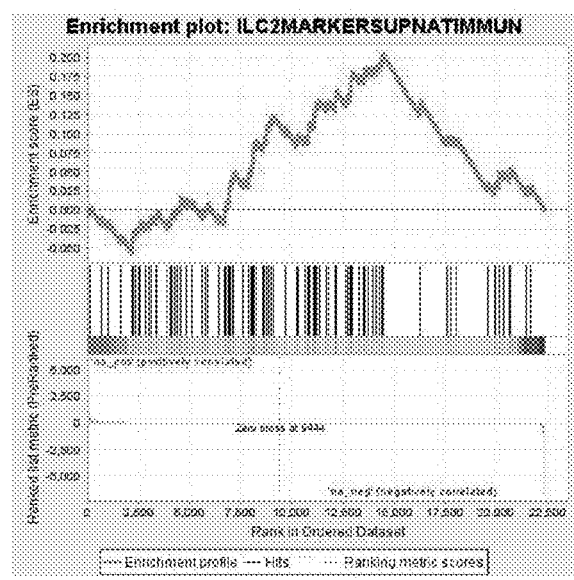

Recent studies have revealed the importance of innate lymphoid cells (ILCs) in homeostasis and inflammation of tumors (Bjorklund et al., 2016, Wallrapp et al., 2017). Although three main populations of ILCs, ILC1, ILC2, and ILC3, have been categorized based on their transcription factor profiles and secreted cytokines (Spits et al., 2013), little is known about their roles in carcinogenesis and immunotherapy resistance. To evaluate ILCs in HPD tumors, we analyzed the transcriptional levels of the marker genes characteristic of the ILC1, ILC2, and ILC3 populations (Bjorklund et al., 2016, Wallrapp et al., 2017). GSEA (Subramanian et al., 2005) showed that the ILC3 marker genes were significantly enriched among the top upregulated genes in the HPD tumors after anti-PD-1 treatment (FIGS. 7A and 7B). In contrast, the ILC1 and ILC2 marker genes were not enriched in either the up- or downregulated genes in the HPD tumors (FIG. 16). These data suggest that the ILC3 population is activated in HPD tumors. To validate this finding, we analyzed the RNA-seq data from other studies that evaluated tumor changes in response to anti-PD-1 therapies. Analysis of the transcriptomes of responding (n=15) and nonresponding (n=13) pre-treatment melanoma tumors from the patients subject to PD-1 blockade (Hugo et al., 2016) showed that ILC3 marker genes were commonly upregulated in the melanoma tumors resistant to anti-PD-1 therapy (FIG. 7C). Based on the RNA-seq data of the KrasG12D mouse model, we also found that there were a large number of ILC3 marker genes significantly upregulated in murine lung adenocarcinoma tumors that were resistant to anti-PD-1 therapy when compared with untreated tumors (Koyama et al., 2016) (FIG. 7D). These results are concordant with our HPD RNA-seq data, suggesting that enrichment of the ILC3 population in the HPD tumors may be a characteristic feature of tumors that are insensitive to anti-PD-1. This finding is consistent with the previous report that ILC3 lymphocytes contribute to the initiation and progression of cancers (Fung et al., 2017). The mechanistic connection between ILC3 population and anti-PD-1 therapy effect is unknown. However, it was reported that ILC3 may promote the growth of mutant tumor cells that express the receptors needed for oncogenic pathways (Fung et al., 2017, Kirchberger et al., 2013). Our and others' data (Riaz et al., 2017) suggested that anti-PD-1 therapy increased tumor mutation burden in patients with cancer with hyperprogressive or progressive tumor phenotype. Therefore, activated ILC3 cell population may be required for the promotion of the growth of more mutant cells in the patients with cancer with HPD or PD subjected to anti-PD-1 therapy.

Pro-Inflammatory Pathways were Activated in the Pre-Therapy Tumors of Patients with HPD and Further Activated by Anti-PD-1 Therapy PD-1 has been demonstrated to inhibit excessive inflammatory responses during infection in mouse models (Lazar-Molnar et al., 2010). To identify the inflammatory changes in HPD tumors, we evaluated changes in inflammatory-related genes included in the "hallmark inflammatory" gene set (Liberzon et al., 2011, Liberzon et al., 2015). To characterize the inflammation activity in post-anti-PD-1 treatment HPD tumors versus pre-treatment tumors, we again utilized GSVA, which identified four founder datasets of inflammation pathways that were significantly enhanced in the HPD tumors after anti-PD-1 treatment (FIG. 8A). In each of these four pro-inflammatory datasets, many more genes were up-than downregulated (FIGS. 8B-8E), suggesting an overall pro-inflammatory trend after anti-PD-1 treatment.

Figure 17:
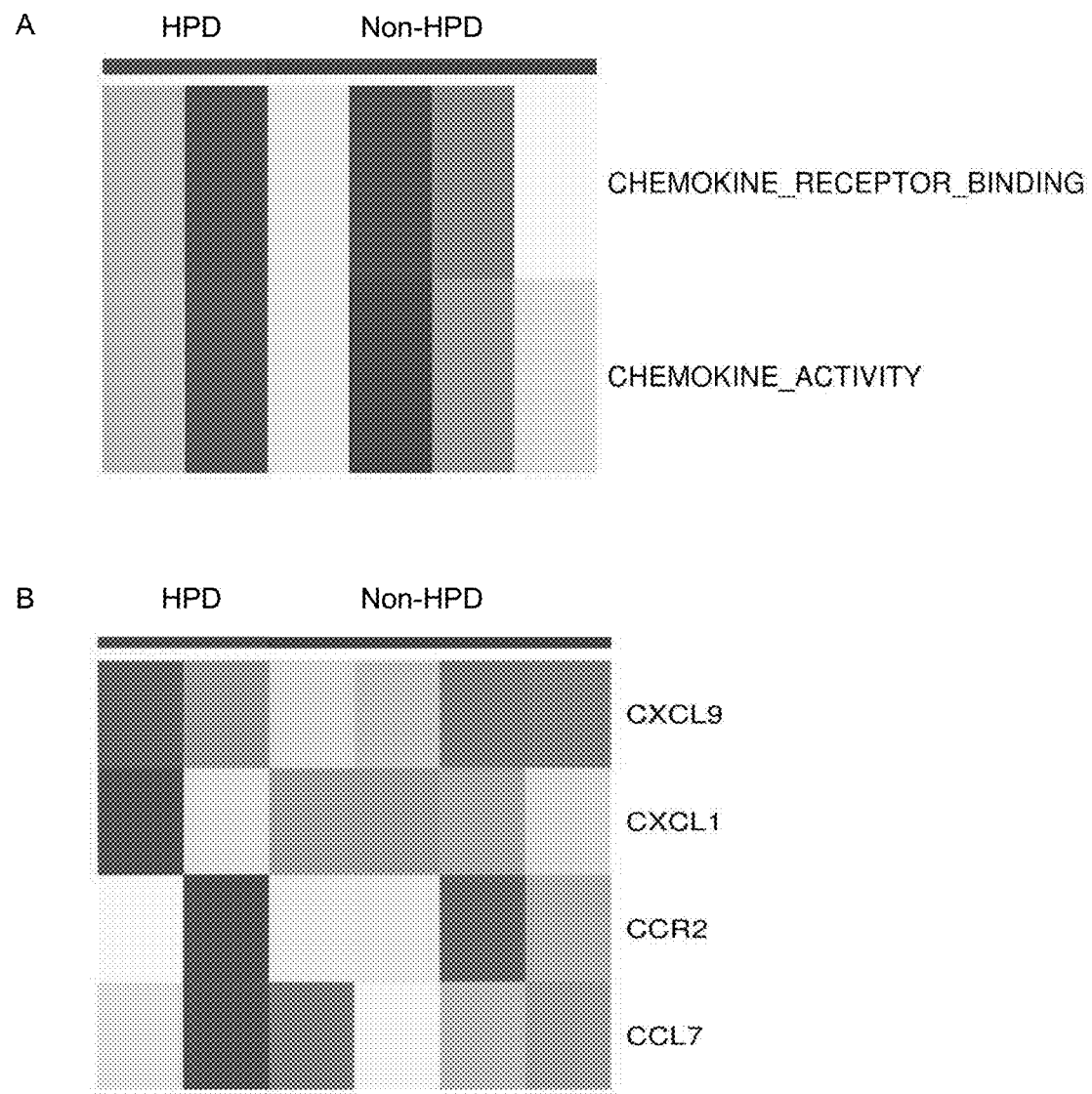
FIG. 17 Pre-α-PD-1 therapy tumors of hyperprogressive patients have elevated inflammation pathway activity (mainly chemokine activity) compared to the responsive patients. Related to FIG. 8. (A) GSVA identified the activation of two founder data sets of inflammation pathways in the pre-therapy tumors of HPD patients compared to the non-HPD patients; (B) The chemokine encoding genes that were up-regulated in the pre-therapy tumors of HPD patients compared to the non-HPD patients.

For comparison, we analyzed the gene expression data of tumor samples from the GSE52562 dataset before anti-PD-1 treatment (Westin et al., 2014). This dataset included two potential HPD patients whose progression-free survival (PFS) was less than 2 months post-pidilizumab treatment (SAMPLE.25 and SAMPLE.5 in Table S4) and four responsive patients whose PFS was more than 2 years (24 months) after treatment (SAMPLE.23, SAMPLE.19, SAMPLE.13, and SAMPLE.17 in Table 3). This analysis showed that the tumors of HPD patients have elevated inflammation pathway activity (mainly chemokine activity) even before anti-PD-1 therapy when compared with tumors from non-HPD patients (FIG. 17). These and our data collectively suggested that anti-PD-1 therapy further boosts the pre-existing high levels of inflammation in patients who subsequently develop HPD in ways that are not conducive to promoting tumor rejection.

TABLE 3

The clinical information of the eighteen follicular lymphoma patients from the GSE52562 study, among whom two patients had PFS less than two months together with advanced tumor progression phenotypes after anti-PD-1 treatment. Related to FIG. 9.

| Exp Id | Sample ID | gender | age | pfs. censorship | pfs. time month | treatment | tissue | HPD status |
|---|---|---|---|---|---|---|---|---|
| GSM1269893 | SAMPLE.25 | F | 67 | 1 | 1.8 | pre-pidilizumab | tumor biopsy | HPD |
| GSM1269873 | SAMPLE.5 | F | 79 | 1 | 2.0 | pre-pidilizumab | tumor biopsy | HPD |
| GSM1269883 | SAMPLE.15 | M | 46 | 1 | 3.7 | pre-pidilizumab | tumor biopsy | nonHPD |
| GSM1269886 | SAMPLE.18 | M | 69 | 0 | 4.1 | pre-pidilizumab | tumor biopsy | nonHPD |
| GSM1269877 | SAMPLE.9 | F | 58 | 1 | 6.5 | pre-pidilizumab | tumor biopsy | nonHPD |
| GSM1269888 | SAMPLE.20 | F | 56 | 0 | 7.1 | pre-pidilizumab | tumor biopsy | nonHPD |
| GSM1269875 | SAMPLE.7 | M | 60 | 1 | 10.1 | pre-pidilizumab | tumor biopsy | nonHPD |
| GSM1269889 | SAMPLE.21 | F | 62 | 1 | 12.7 | pre-pidilizumab | tumor biopsy | nonHPD |
| GSM1269871 | SAMPLE.3 | M | 51 | 1 | 13.5 | pre-pidilizumab | tumor biopsy | nonHPD |
| GSM1269894 | SAMPLE.26 | M | 58 | 1 | 15.3 | pre-pidilizumab | tumor biopsy | nonHPD |
| GSM1269890 | SAMPLE.22 | M | 70 | 1 | 18.6 | pre-pidilizumab | tumor biopsy | nonHPD |
| GSM1269892 | SAMPLE.24 | M | 63 | 0 | 18.8 | pre-pidilizumab | tumor biopsy | nonHPD |
| GSM1269879 | SAMPLE.11 | M | 67 | 1 | 19.6 | pre-pidilizumab | tumor biopsy | nonHPD |
| GSM1269869 | SAMPLE.1 | F | 61 | 1 | 21.6 | pre-pidilizumab | tumor biopsy | nonHPD |
| GSM1269891 | SAMPLE.23 | F | 37 | 0 | 26.5 | pre-pidilizumab | tumor biopsy | nonHPD |
| GSM1269887 | SAMPLE.19 | F | 41 | 0 | 30.4 | pre-pidilizumab | tumor biopsy | nonHPD |
| GSM1269881 | SAMPLE.13 | M | 58 | 0 | 30.8 | pre-pidilizumab | Itumor biopsy | nonHPD |
| GSM1269885 | SAMPLE.17 | F | 45 | 0 | 35.0 | pre-pidilizumab | tumor biopsy | nonHPD |

HPD-Associate Gene Expression Signature

Based on the pre-therapy tumor expression data of Dataset_1 (See Methods), we developed a 121-gene set to differentiate HPD patients from non-HPD patients (FIG. 18, Table 4). The effectiveness of this 121-gene classifier in the identification of HPD patients was tested using the pre-therapy tumor expression data from Dataset_2 (See Methods). This classifier had an area under curve (AUC) value of 0.91 (95% confidence interval [CI], 0.87-0.96), a sensitivity of 71% (95% CI, 51%-87%), and a specificity of 93% (95% CI, 80%-99%) in predicting HPD patients in Dataset_2 (FIG. 9A). Kaplan-Meier analysis of TCGA data showed that the 121-gene expression signature can significantly separate low-risk group from high-risk group in the 13 major types of cancers including melanoma (SKCM), glioma, and carcinomas of the esophagus (ESCA), stomach (STAD), breast (BRCA), kidney (KIRC), bladder (BLCA), liver (LIHC), head and neck (HNSC), lung (LUAD and LUSC), colon (COAD), and pancreas (PAAD) (FIGS. 9B-9D and 19-21). This panel was able to identify extremely high-risk groups in ESCA, COAD, and PAAD (FIGS. 9B-9D).

TABLE 4

The information of the 121 genes in the expression signature of pre-anti-PD-1 treatment tumors that may be predictive of HPD (hyperprogressive disease) patients after anti-PD-1 immunotherapy.

| Gene Symbol | Entrez Gene Name | Location | Type(s) |
| --- | --- | --- | --- |
| AAK1 | AP2 associated kinase 1 | Cytoplasm | kinase |
| ACOT1 | acyl-CoA thioesterase 1 | Cytoplasm | enzyme |
| ACOT2 | acyl-CoA thioesterase 2 | Cytoplasm | enzyme |
| ADAR | adenosine deaminase, RNA specific | Nucleus | enzyme |
| AFF1 | AF4/FMR2 family member 1 | Nucleus | transcription regulator |
| ANKS6 | ankyrin repeat and sterile alpha motif domain containing 6 | Cytoplasm | other |
| ANXA5 | annexin A5 | Plasma Membrane | transporter |
| ARID2 | AT-rich interaction domain 2 | Nucleus | transcription regulator |
| ARL1 | ADP ribosylation factor like GTPase 1 | Cytoplasm | enzyme |
| ARMC9 | armadillo repeat containing 9 | Cytoplasm | other |
| ATF7IP | activating transcription factor 7 interacting protein | Nucleus | transcription regulator |
| ATP11C | ATPase phospholipid transporting 11C | Plasma Membrane | transporter |
| ATP5L | ATP synthase membrane subunit g | Cytoplasm | enzyme |
| BAZ1B | bromodomain adjacent to zinc finger domain 1B | Nucleus | transcription regulator |
| BAZ2A | bromodomain adjacent to zinc finger domain 2A | Nucleus | transcription regulator |
| C17orf97 | chromosome 17 open reading frame 97 | Other | other |
| CAMSAP1 | calmodulin regulated spectrin associated protein 1 | Cytoplasm | other |
| CARD8 | caspase recruitment domain family member 8 | Nucleus | other |
| CCNA1 | cyclin A1 | Nucleus | other |
| CCNT1 | cyclin T1 | Nucleus | transcription regulator |
| CD63 | CD63 molecule | Plasma Membrane | other |
| CD96 | CD96 molecule | Plasma Membrane | other |
| CHD4 | chromodomain helicase DNA binding protein 4 | Nucleus | enzyme |
| CLSTN3 | calsyntenin 3 | Plasma Membrane | other |
| COL4A1 | collagen type IV alpha 1 chain | Extracellular Space | other |
| COL4A2 | collagen type IV alpha 2 chain | Extracellular Space | other |
| COMMD9 | COMM domain containing 9 | Cytoplasm | other |
| CORO1C | coronin 1C | Cytoplasm | other |
| CPT1A | carnitine palmitoyltransferase 1A | Cytoplasm | enzyme |
| CREBZF | CREB/ATF bZIP transcription factor | Nucleus | transcription regulator |
| CSNK1G1 | casein kinase 1 gamma 1 | Cytoplasm | kinase |
| CTLA4 | cytotoxic T-lymphocyte associated protein 4 | Plasma Membrane | transmembrane receptor |
| CYP2D6 | cytochrome P450 family 2 subfamily D member 6 | Cytoplasm | enzyme |
| DGKD | diacylglycerol kinase delta | Cytoplasm | kinase |
| DIAPH1 | diaphanous related formin 1 | Plasma Membrane | other |
| EID2 | EP300 interacting inhibitor of differentiation 2 | Nucleus | other |
| ELK4 | ELK4, ETS transcription factor | Nucleus | transcription regulator |
| EP300 | E1A binding protein p300 | Nucleus | transcription regulator |
| ERN1 | endoplasmic reticulum to nucleus signaling 1 | Cytoplasm | kinase |
| FAHD1 | fumarylacetoacetate hydrolase domain containing 1 | Cytoplasm | enzyme |
| FAM104B | family with sequence similarity 104 member B | Other | other |
| FBXL17 | F-box and leucine rich repeat protein 17 | Other | other |
| FPGT | fucose-1-phosphate guanylyltransferase | Cytoplasm | enzyme |
| FUBP3 | far upstream element binding protein 3 | Nucleus | transcription regulator |
| FUCA2 | alpha-L-fucosidase 2 | Extracellular Space | enzyme |
| GALNT10 | polypeptide N-acetylgalactosaminyltransferase 10 | Cytoplasm | enzyme |
| GALNT2 | polypeptide N-acetylgalactosaminyltransferase 2 | Cytoplasm | enzyme |
| GAPVD1 | GTPase activating protein and VPS9 domains 1 | Cytoplasm | other |
| GATAD2B | GATA zinc finger domain containing 2B | Nucleus | transcription regulator |
| GBF1 | golgi brefeldin A resistant guanine nucleotide exchange factor 1 | Cytoplasm | other |
| GOLIM4 | golgi integral membrane protein 4 | Cytoplasm | other |
| GPR18 | G protein-coupled receptor 18 | Plasma Membrane | G-protein coupled receptor |
| HADH | hydroxyacyl-CoA dehydrogenase | Cytoplasm | enzyme |
| HHLA3 | HERV-H LTR-associating 3 | Other | other |
| HIVEP1 | human immunodeficiency virus type I enhancer binding protein 1 | Nucleus | transcription regulator |
| HIVEP2 | human immunodeficiency virus type I enhancer binding protein 2 | Nucleus | transcription regulator |
| HMBS | hydroxymethylbilane synthase | Cytoplasm | enzyme |
| HPGDS | hematopoietic prostaglandin D synthase | Cytoplasm | enzyme |
| HSPG2 | heparan sulfate proteoglycan 2 | Extracellular Space | enzyme |
| KDM6B | lysine demethylase 6B | Extracellular Space | enzyme |
| KDR | kinase insert domain receptor | Plasma Membrane | kinase |
| KLHDC8B | kelch domain containing 8B | Cytoplasm | other |
| LAMTOR3 | late endosomal/lysosomal adaptor, MAPK and MTOR activator 3 | Cytoplasm | other |
| LGALS12 | galectin 12 | Extracellular Space | other |
| LNPEP | leucyl and cystinyl aminopeptidase | Cytoplasm | peptidase |
| LRP6 | LDL receptor related protein 6 | Plasma Membrane | transmembrane receptor |
| MAGEH1 | MAGE family member H1 | Cytoplasm | other |
| MEF2D | myocyte enhancer factor 2D | Nucleus | transcription regulator |
| MTIF3 | mitochondrial translational initiation factor 3 | Cytoplasm | translation regulator |

TABLE 4-continued

The information of the 121 genes in the expression signature of pre-anti-PD-1 treatment tumors that may be predictive of HPD (hyperprogressive disease) patients after anti-PD-1 immunotherapy.

| Gene Symbol | Entrez Gene Name | Location | Type(s) |
|---|---|---|---|
| NFE2L2 | nuclear factor, erythroid 2 like 2 | Nucleus | transcription regulator |
| NOTCH3 | notch 3 | Plasma Membrane | transcription regulator |
| NPLOC4 | NPL4 homolog, ubiquitin recognition factor | Nucleus | other |
| NSD1 | nuclear receptor binding SET domain protein 1 | Nucleus | transcription regulator |
| NUP188 | nucleoporin 188 | Nucleus | other |
| OBSCN | obscurin, cytoskeletal calmodulin and titin-interacting RhoGEF | Cytoplasm | kinase |
| OTUD7B | OTU deubiquitinase 7B | Cytoplasm | peptidase |
| PAK2 | p21 (RAC1) activated kinase 2 | Cytoplasm | kinase |
| PCDHGB7 | protocadherin gamma subfamily B, 7 | Other | other |
| PHF8 | PHD finger protein 8 | Nucleus | enzyme |
| PPM1L | protein phosphatase, Mg2+/Mn2+ dependent 1L | Cytoplasm | phosphatase |
| PPP2R3C | protein phosphatase 2 regulatory subunit B"gamma | Cytoplasm | other |
| PTPN3 | protein tyrosine phosphatase, non-receptor type 3 | Cytoplasm | phosphatase |
| PTS | 6-pyruvoyltetrahydropterin synthase | Cytoplasm | enzyme |
| RANGAP1 | Ran GTPase activating protein 1 | Nucleus | other |
| SATB1 | SATB homeobox 1 | Nucleus | transcription regulator |
| SERPINF1 | serpin family F member 1 | Extracellular Space | other |
| SETX | senataxin | Nucleus | enzyme |
| SLC25A34 | solute carrier family 25 member 34 | Cytoplasm | other |
| SLC27A1 | solute carrier family 27 member 1 | Plasma Membrane | transporter |
| SLC38A6 | solute carrier family 38 member 6 | Plasma Membrane | transporter |
| SLC6A6 | solute carrier family 6 member 6 | Plasma Membrane | transporter |
| SMURF1 | SMAD specific E3 ubiquitin protein ligase 1 | Cytoplasm | enzyme |
| SNAPC4 | small nuclear RNA activating complex polypeptide 4 | Nucleus | transcription regulator |
| SORT1 | sortilin 1 | Plasma Membrane | G-protein coupled receptor |
| SPEN | spen family transcriptional repressor | Nucleus | transcription regulator |
| SPIN2A | spindlin family member 2A | Other | other |
| SPP1 | secreted phosphoprotein 1 | Extracellular Space | cytokine |
| SSBP2 | single stranded DNA binding protein 2 | Nucleus | transcription regulator |
| OBFC1 | STN1, CST complex subunit | Nucleus | other |
| SYTL4 | synaptotagmin like 4 | Cytoplasm | transporter |
| TCF4 | transcription factor 4 | Nucleus | transcription regulator |
| TEX261 | testis expressed 261 | Extracellular Space | other |
| TGOLN2 | trans-golgi network protein 2 | Cytoplasm | other |
| TIMM8B | translocase of inner mitochondrial membrane 8 homolog B | Cytoplasm | transporter |
| TLN1 | talin 1 | Plasma Membrane | other |
| TMEM99 | transmembrane protein 99 | Other | other |
| TNFRSF25 | TNF receptor superfamily member 25 | Plasma Membrane | transmembrane receptor |
| TNKS2 | tankyrase 2 | Nucleus | enzyme |
| TRIO | trio Rho guanine nucleotide exchange factor | Cytoplasm | kinase |
| TRIP12 | thyroid hormone receptor interactor 12 | Cytoplasm | enzyme |
| TSC2 | TSC complex subunit 2 | Cytoplasm | other |
| TSPAN3 | tetraspanin 3 | Plasma Membrane | other |
| UBTF | upstream binding transcription factor, RNA polymerase I | Nucleus | transcription regulator |
| KIAA2018 | upstream transcription factor family member 3 | Other | other |
| VHL | von Hippel-Lindau tumor suppressor | Nucleus | transcription regulator |
| WDR44 | WD repeat domain 44 | Cytoplasm | other |
| YWHAE | tyrosine 3-monooxygenase/tryptophan 5-monooxygenase activation protein epsilon | Cytoplasm | other |
| YWHAQ | tyrosine 3-monooxygenase/tryptophan 5-monooxygenase activation protein theta | Cytoplasm | other |
| ZFP36L1 | ZFP36 ring finger protein like 1 | Nucleus | transcription regulator |
| ZNF609 | zinc finger protein 609 | Nucleus | other |
| ZNF878 | zinc finger protein 878 | Other | other |

Checkpoint blockade with anti-PD-1 antibodies has resulted in excellent responses in a subset of patients with cancer. However, there is a sizable proportion of patients with cancer who do not respond to anti-PD-1 treatment, with a subset of these patients developing hyperprogression with accelerated tumor growth after anti-PD-1 immunotherapy (Champiat et al., 2017, Kato et al., 2017). Currently, there is a lack of systematic genome studies to identify the genes or immune factors that predict resistance to immune checkpoint inhibition or HPD in response to anti-PD-1 treatment. In this study, we utilized WES and RNA-seq approaches to identify the mutation spectrum and gene expression profiling changes in HPD tumors when compared with pre-therapy tumors. We also performed pathway and tumor immunogenicity analyses based on the RNA-seq data. Finally, we combined our data with publicly available datasets and developed an HPD gene expression signature capable of predicting patients unlikely to respond to anti-PD-1.

Figure 22:
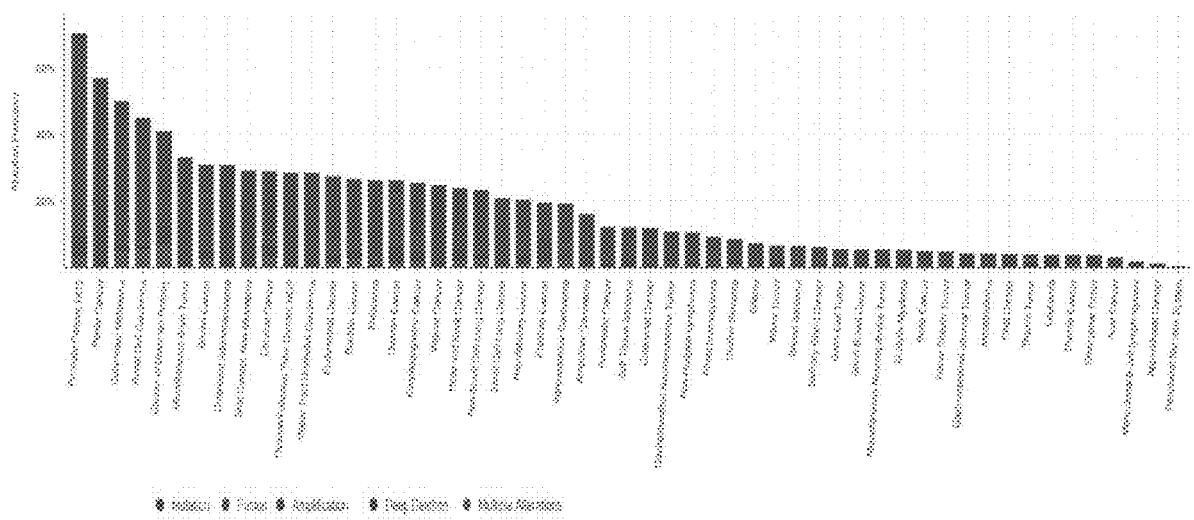
FIG. 22 The mutation analysis highlighted eleven genes with deleterious mutations in the HPD tumors after anti-PD-1 therapy. Related to Table 2. Most of these genes have not been adequately studied in the cancer context before. Querying the HPD tumors associated 11-mutated-gene set in the cBioPortal website showed that this gene set had somatic mutations or copy number aberrations (CNAs) in 8887 (22%) of 41320 sequenced patients. The frequencies of tumor samples having somatic alterations in at least one of the eleven genes among each type of cancers archived in cBioPortal were shown in the figure.

The mutation analysis highlighted 11 genes with deleterious mutations in the HPD tumors after anti-PD-1 therapy (Table 2). Most of these genes have not been adequately studied in the context of cancer before. However, a query of this 11 mutated gene set in the cBioPortal website (Cerami et al., 2012, Gao et al., 2013) showed that this gene set has somatic mutations or copy number aberrations (CNAs) in 8,887 (22%) of the 41,320 sequenced patients. The alterations of these 11 genes were most frequent in the six major cancer types with an alteration frequency >30% (FIG. 22), i.e., prostate cancer (70.8% tumor samples had mutations or CNAs in at least one of the 11 genes), melanoma (50.2% altered), renal cell carcinoma (45.3% altered), brain cancer (33.3% altered), breast cancer (31.1% altered), and colorectal adenocarcinoma (31.0% altered). These data support the cancer linkage to these 11 genes, the mutations of which could contribute to the tumor hyperprogressive phenotype.

Among the 11 genes, some have tumor suppressive properties, good examples being TSC2 and VHL. Inactivating mutations in TSC2 that encode the protein tuberin lead to constitutive activation of mTOR kinase through the Rheb-GTP signaling axis (Menon et al., 2014, Zoncu et al., 2011), which in turn induces cell growth, motility, invasion, and development of tumors (Goncharova et al., 2004, Goncharova et al., 2006). These outcomes were consistent with our observation that the deleterious pY1611S mutation in the key Rap/ran-GAP domain of the TSC2 protein (Table 2, FIG. 13) occurred in the hyperprogressive tumors after anti-PD-1 therapy. We also found that the VHL gene had a deleterious mutation—pL117V—in the ccRCC hyperprogressive tumors after anti-PD-1 treatment (Table 2). VHL, located on chromosome 3p25, is a major tumor suppressor gene involved in ccRCC oncogenesis (Gossage et al., 2015). Interestingly, a recent study found that PD-L1 expression was associated with dense PD-1 expression and wild-type VHL ccRCC, but not with mutated/inactivated VHL ccRCC (Kammerer-Jacquet et al., 2017). Therefore, only the patients with ccRCC with wild-type VHL may benefit from immunotherapies inhibiting PD-L1/PD-1 (Kammerer-Jacquet et al., 2017). In our case, we found that only the post-anti-PD-1 therapy hyperprogressive ccRCC tumor had detectable deleterious VHL mutation, but the pre-therapy ccRCC tumor did not. This suggested that the selection pressure of anti-PD-1 therapy eliminated most of the wild-type VHL ccRCC cells but had little effect on cells with mutated VHL ccRCC, such that these mutated cells were highly enriched in the post-therapy HPD tumors. This has significant implications in that it suggests that ccRCC cells with an altered/mutated VHL gene may be a key factor leading to HPD after anti-PD-1 therapy.

Figure 4:
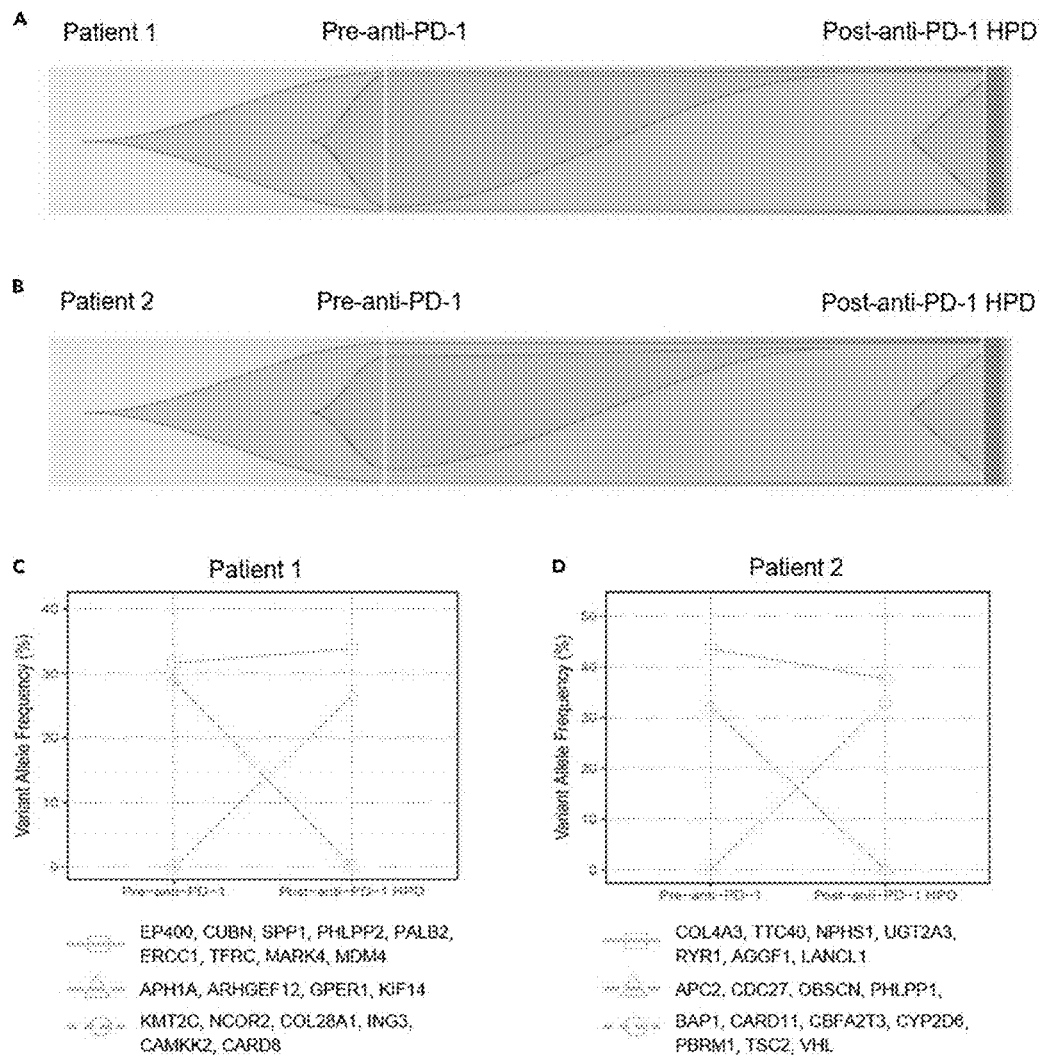
FIG. 4. Illustration of Clonal Evolution of the Tumors before and after Anti-PD-1 Immunotherapy of the Two Patients with HPD. (A-D) (A) Tumor clonal evolution in Patient 1 and (B) tumor clonal evolution in Patient 2. The gray area denotes the tumor clones unaffected by anti-PD-1 therapy, the green and blue areas denote the tumor clones diminishing and appearing due to anti-PD-1 therapy. The dynamics of these clones represented by changes in the variant allele frequency between the pre- and post-therapy tumors was plotted for (C) Patient 1 and (D) Patient 2. See also FIGS. 14 and 15.

The pre- and post-treatment tumors in this study were acquired through biopsy from the primary lesion. After anti-PD-1 therapy, the initial minor subclones of somatic mutations could be boosted by the treatment and expanded in the tumor samples of the two HPD patients as shown in FIG. 4, which contributed to the tumor heterogeneity that may account for changes in the mutational and/or expression landscape. Clonal evolution analysis (FIG. 4) indicates that HPD tumor-specific mutations in TSC2 and VHL along with mutations in a number of other cancer genes including KMT2C, NCOR2, COL28A1, ING3, CAMKK2, CARD8, BAP1, CARD11, CBFA2T3, CYP2D6, and PBRM1 could be significant to the progression of nonaggressive pre-therapy tumors to the hyperprogressive state after anti-PD-1 treatment. FIG. 12 showed that the mutated KMT2C, TSC2, VHL, and CYP2D6 genes were involved in the gene-gene interaction network leading to suppression of the TP53 pathway activity. Previous studies showed that KMT2C (MLL3) co-activates TP53, whereas KMT2C levels decrease during cancer progression, which correlates with distinct clinical stages (Ford and Dingwall, 2015, Lee et al., 2009, Rabello et al., 2018). These results are consistent with our observations in HPD tumors after anti-PD-1 treatment.

Figure 3:
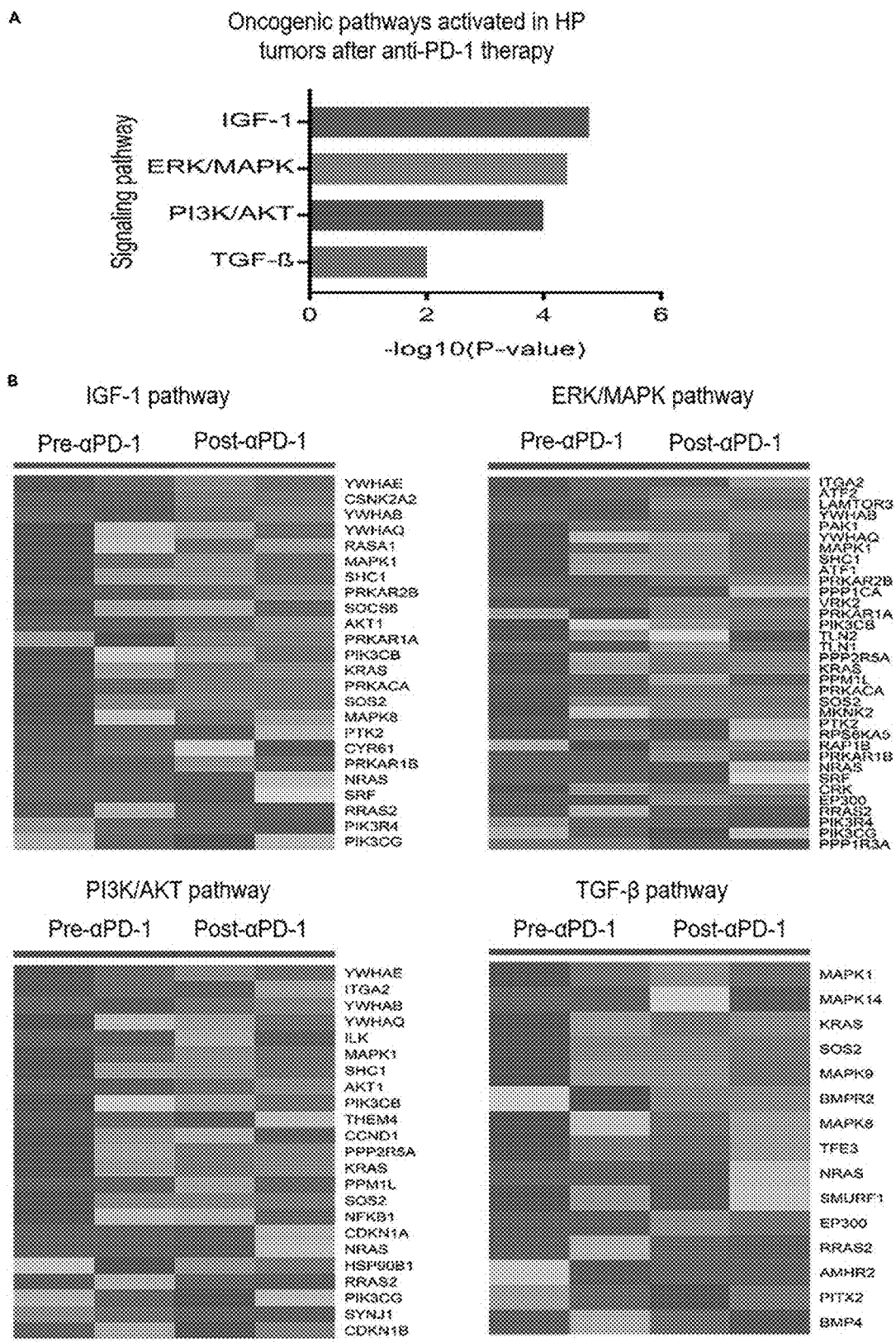
FIG. 3. Activation of Oncogenic Pathways in HP Tumors after Anti-PD-1 Therapy. (A and B) (A) Four oncogenic pathways were activated in the HP tumors. (B) The differentially expressed genes in these oncogenic pathways. Most of the genes were upregulated in the HP tumors after anti-PD-1 therapy. HP, hyperprogressive.

Our RNA-seq data revealed that the IGF-1, ERK/MAPK, PI3K/AKT, and TGF-β signaling pathways were activated in the HPD tumors after anti-PD-1 therapy (FIG. 3). Recent studies have found that TGF-β signaling may play an important role in resistance to immunotherapy. For example, Mariathasan et al. reported that lack of response to anti-PD-L1 antibody was associated with TGF-β signaling in fibroblasts and the exclusion of CD8+ T cells, indicating that TGF-β-mediated stromal remodeling restricts T cell infiltration to suppress antitumor immunity and that TGF-β inhibition may enhance the efficacy of immune checkpoint blockade (Mariathasan et al., 2018). In parallel, Tauriello et al. found that single-agent PD-1/PD-L1 inhibition had little effect, but co-targeting TGF-β produced a robust antitumor immune response that could prevent the development of metastasis and eliminate established metastases in a mouse model (Tauriello et al., 2018). Collectively, these studies indicate that inhibiting TGF-β could significantly improve the efficacy of anti-PD-1/anti-PD-L1 treatment (Mariathasan et al., 2018, Tauriello et al., 2018). Herein, our data suggest that enhanced TGF-3 signaling could also contribute to the development of HPD after anti-PD-1 therapy. Therefore, inhibiting TGF-β signaling may also help prevent the development of HPD in response to anti-PD-1 treatment. Another interesting finding is the activation of PI3K/AKT in HPD tumors. A recent study demonstrated that the activity of PI3K/AKT signaling was crucial for lymphomas with PD-1 deletion (Wartewig et al., 2017). Therefore, when the tumors are exposed to anti-PD-1 therapy, elevated PI3K/AKT signaling may be another important mechanism for the survival, progression, or even hyperprogression of the tumor cells.

Figure 6:
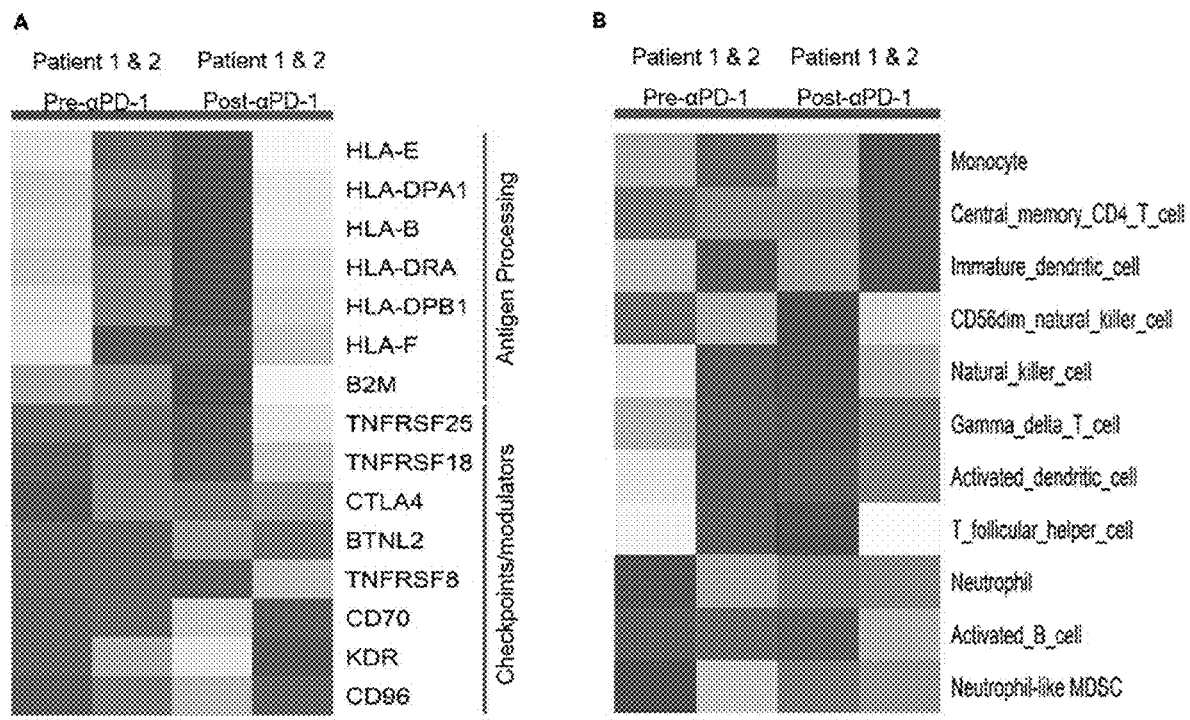
FIG. 6. Changes in the Expression of Critical Immune-Related Genes and the Activity of Immune Cell Populations Contribute to Decreased Immunogenicity in the Post-α-PD-1 HPD Tumors. (A) Seven genes involved in antigen processing were downregulated, whereas eight genes encoding immune checkpoints or modulators were upregulated in hyperprogressor tumors. (B) The activity of eight immune cell populations were weakened and three were strengthened, as detected by GSVA method. See also FIG. 23.

The HPD tumors had reduced tumor immunogenicity when compared with the pre-therapy tumors. Such reduction may be caused by downregulation of antigen-processing genes, including several HLA genes and β2M, and upregulation of certain immune checkpoint or modulator genes other than PD-1/PD-L1 (FIGS. 5 and 6). In the context of studying 28 immune cell populations critical to pan-cancer immunogenomics (Angelova et al., 2015, Charoentong et al., 2017), we found that the activity of eight immune cell populations were weakened and two were strengthened in the HPD tumors. The weakened immune cell populations including monocytes, CD4 helper T cells, dendritic cells, and NK cells may contribute to the ability of HPD tumors to escape immune surveillance. The enhanced cell populations such as neutrophils are known to have a number of pro-tumor properties (Galdiero et al., 2013, Mishalian et al., 2013, Sagiv et al., 2015, Tuting and de Visser, 2016), thus the increase in neutrophil activity in HPD tumors was not surprising.

Figure 23:
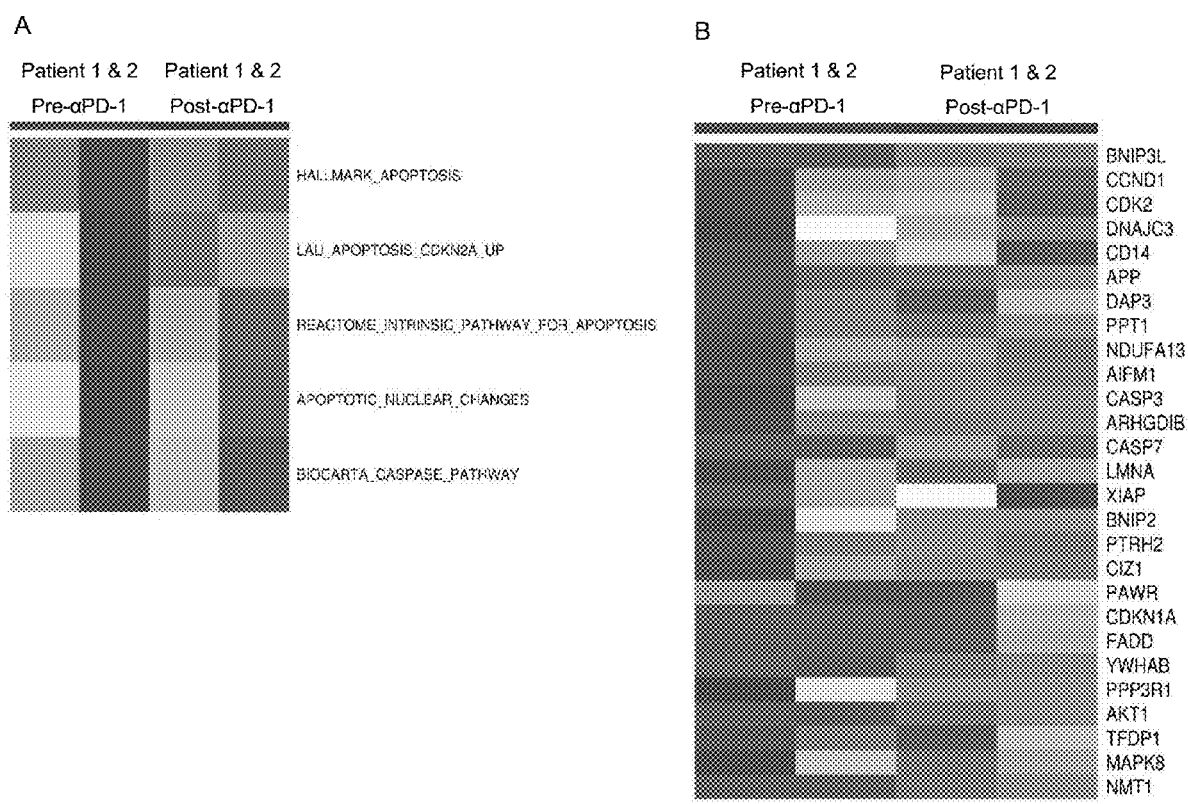
FIG. 23 Changes of the apoptosis pathway activity in the after anti-PD-1 immunotherapy tumors of the HPD patients. Related to FIG. 5 and FIG. 6. (A) Five apoptosis gene sets were activated in the two patients after anti-PD-1 immunotherapy; (B) 27 apoptotic genes of these five apoptosis gene sets including marker genes in caspase/bcl2 pathways (CASP3, CASP7, BNIP2, BNIP3L) were significantly up-regulated.

The two patients developed HPD after anti-PD-1 therapy, indicating the adverse immunity changes that may result in an immunosuppressive environment. The decreased portion of immune cell phenotypes after anti-PD-1 therapy led us to speculate whether anti-PD-1 therapy contributed to accelerated AICD (activation-induced cell death) in these two patients. To test this hypothesis, we applied the GSVA approach to the apoptosis gene sets collected in the MSigDB database (Liberzon et al., 2015). It can be seen that five apoptosis gene sets were activated in the two patients after anti-PD-1 therapy (FIG. 23A), of which 27 apoptotic genes including marker genes in caspase/bcl2 pathways (CASP3, CASP7, BNIP2, and BNIP3L) were significantly upregulated (FIG. 23B). This indicated that the accelerated AICD may occur in the anti-tumor activating lymphocytes, which accounted for the decreased portion of immune cell phenotypes and enhanced immunosuppressive environment after anti-PD-1 therapy.

Figure 7:
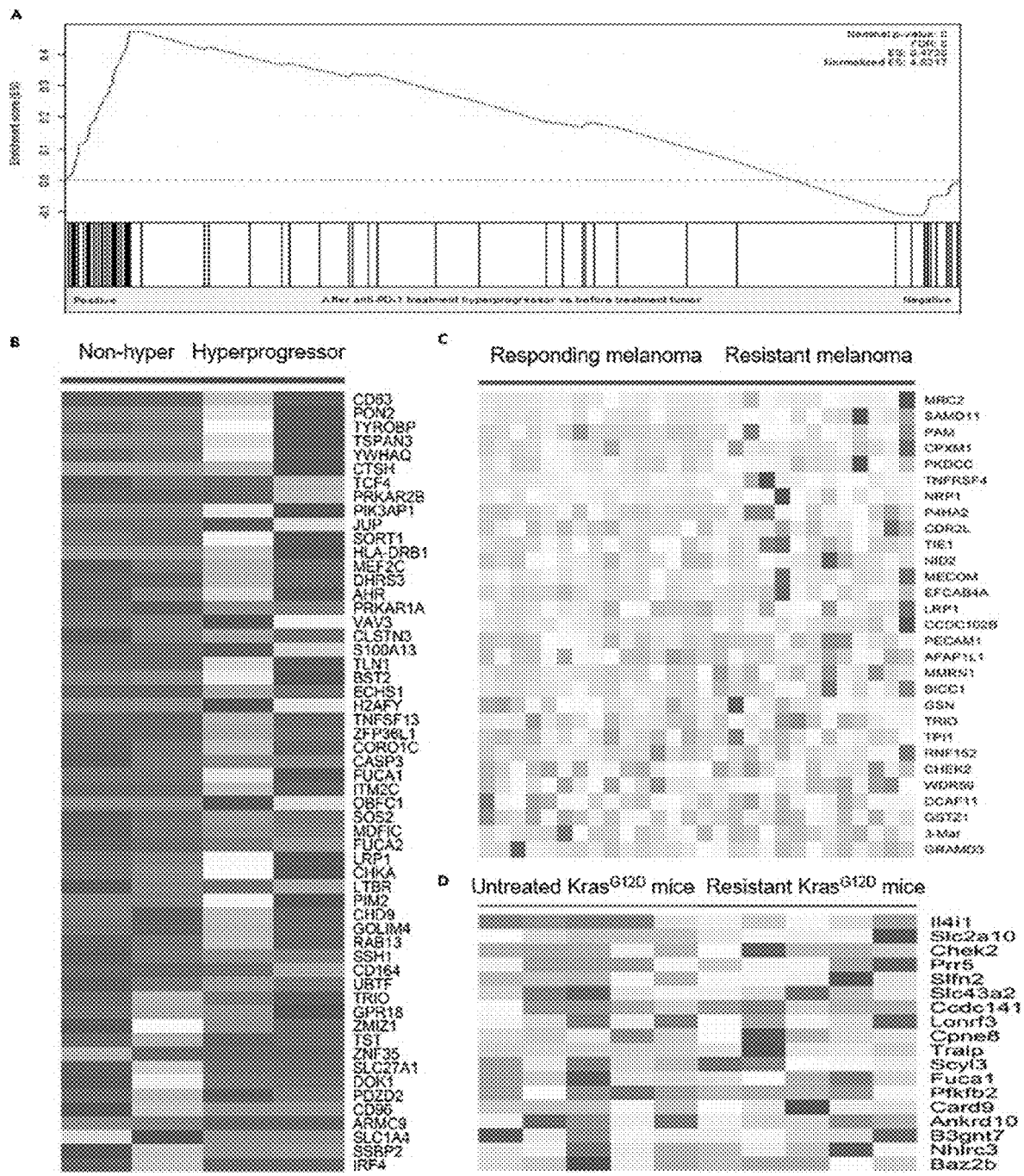
FIG. 7. The ILC3 Population Was Activated in the HPD Tumors after Anti-PD-1 Therapy. (A-D) (A) GSEA showed that ILC3 marker genes were significantly enriched in the top upregulated genes in HPD tumors resistant to anti-PD-1 therapy. (B) Most of the differentially expressed ILC3 marker genes in the HPD tumors resistant to anti-PD-1 treatment were upregulated. (C) A higher percentage of ILC3 marker genes were upregulated in the nonresponding melanoma tumors resistant to anti-PD-1 therapy based on the analysis of data from an independent study in humans. (D) Upregulation of ILC3 marker genes comparing anti-PD-1-treatment-resistant mouse tumors with untreated tumors in the Kras$^{G12D}$ mouse model.

So far, cancer immunotherapies have largely focused on T lymphocytes. However, ILCs could also play important roles in the immune response. ILCs were classified into cytotoxic ILCs, such as NK cells, and helper-like ILCs, such as the ILC1, ILC2, and ILC3 subsets. Much of the role of ILCs other than NK cells in cancer and immunotherapy remain elusive. ILCs might represent promising targets in the context of cancer therapy because they are endowed with potent immunomodulatory properties. In the present study, we analyzed the dynamic changes in the activity of ILC populations associated with anti-PD-1 therapy. This represents the first study analyzing the ILC populations in hyperprogressive tumors after anti-PD-1 therapy. Although ILC1 and ILC2 subsets did not show significant changes according to GSEA (FIG. 16), the ILC3 population was activated in HPD tumors compared with pre-therapy tumors (FIG. 7). Among the three subsets of ILCs, the role of ILC3 is gaining increased interest for its potential tumor-promoting activities. ILC3 that produces interleukin (IL)-22 has also been shown to promote tumor growth mediated via STAT3 activation (Kirchberger et al., 2013). Another study showed that ILC3 promoted lymphatic metastasis by modulating the local chemokine milieu of cancer cells (Irshad et al., 2017). ILC3 may also promote tumor formation and progression by suppressing T cell responses (van Beek et al., 2016). It had been shown that intestinal ILC3 cells limit T cell responses and induce T cell death via outcompeting T cells for IL-2 (Hepworth et al., 2015). We observed upregulated expression of ILC3 marker genes by anti-PD-1 immunotherapy in the two HPD patients, which may contribute to the suppression of T cell responses or the induction of T cell death. Our findings were in line with those of previous studies, indicating that inhibiting ILC3 may complement anti-PD-1 treatment to reduce the likelihood of developing hyperprogressive tumors after the therapy.

It is worth mentioning that IL-22 expression was not detected in the before and after anti-PD-1 treatment FFPE samples of the two patients, which may be due to the influence of the degradation of the RNA samples from the FFPE specimens on gene expression study. However, previous studies have defined a large group of marker genes whose expressions were characteristic of the ILC3 cell population (Bjorklund et al., 2016, Wallrapp et al., 2017). For example, the ILC3 cells were defined by using a repertoire of around 400 genes (Bjorklund et al., 2016, Wallrapp et al., 2017), which became the basis of our analyses on ILC3 cells. Therefore, we analyzed the expression pattern changes of these marker genes to study the dynamic changes of ILC cell populations in response to the anti-PD-1 immunotherapy in the tumors of the HPD patients (FIGS. 7 and 16).

Figure 8:
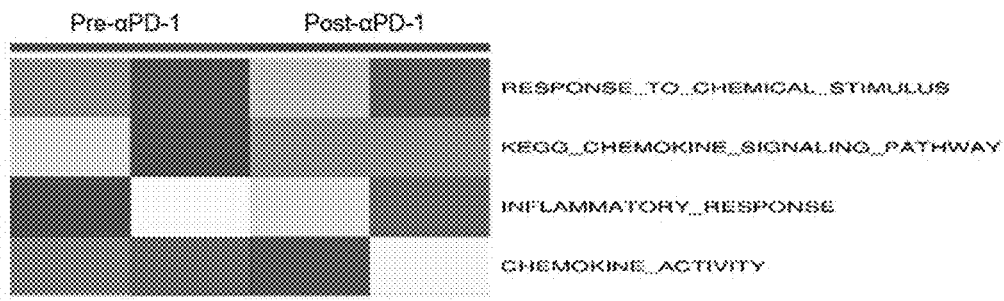
FIG. 8. Activation of Inflammatory Pathways in the HPD Tumors after Anti-PD-1 Treatment. (A) GSVA identified the activation of four founder datasets of inflammation pathways. (B) Differentially expressed genes in the inflammatory signature of RESPONSE_TO_CHEMICAL_STIMULUS; (C) Differentially expressed genes in the inflammatory signature of KEGG_CHEMOKINE_SIGNALING_PATHWAY; (D) Differentially expressed genes in the inflammatory signature of INFLAMMATORY_RESPONSE; (E) Differentially expressed genes in the inflammatory signature of CHEMOKINE_ACTIVITY. In each of the four pro-inflammatory datasets from (B-E), there were much more upregulated than downregulated genes. See also FIG. 17.
Figure 8:
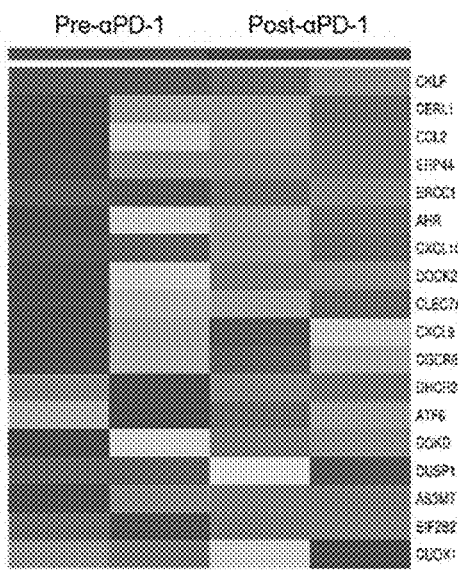
Figure 8:
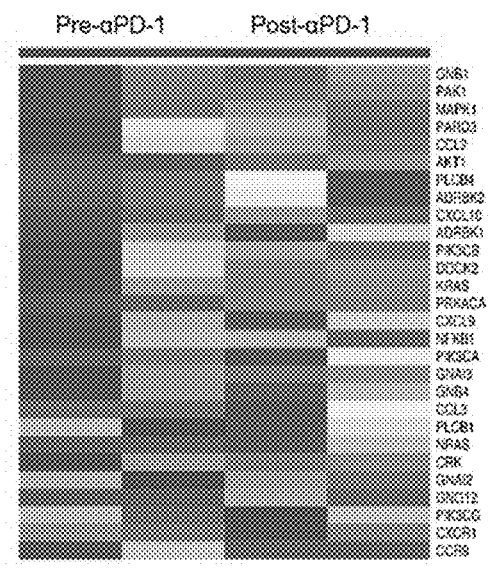
Figure 8:
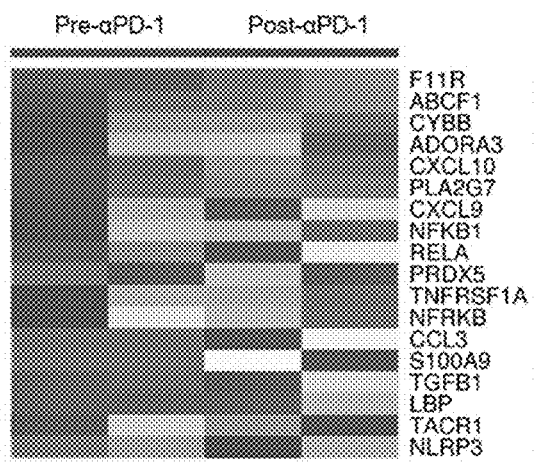
Figure 8:
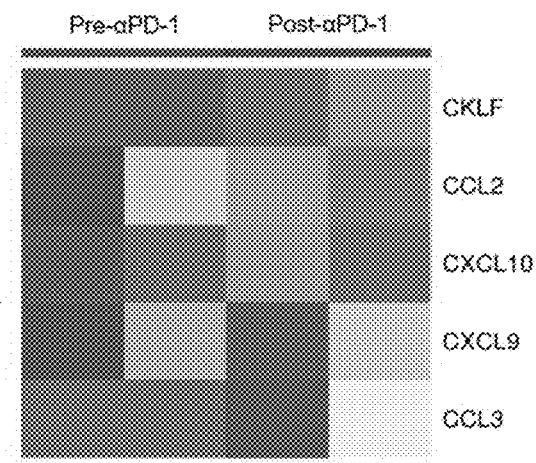

Previous research showed that PD-1-deficient mice were extraordinarily sensitive to tuberculosis and had much shorter survival times compared with wild-type mice (Lazar-Molnar et al., 2010). This sensitivity results from the need for the PD-1 pathway to control excessive inflammatory responses to tuberculosis infection in the lungs of mice (Lazar-Molnar et al., 2010). This led us to hypothesize that the PD-1 pathway may also be required to control excessive inflammatory responses in patients susceptible to HPD. If anti-PD-1 therapy is administered to HPD patients, it may contribute to tumor growth by further upregulating inflammatory pathway activities. The analyses of our data and those of others (Westin et al., 2014) confirmed this hypothesis by showing that anti-PD-1 therapy can further boost the pre-existing high levels of inflammation in HPD patients, and thus contribute to the hyperprogressive phenotype (FIGS. 8 and 17).

On the basis of genome-wide expression data of tumors from our study, and two publicly available datasets (before anti-PD-1 therapy) (Riaz et al., 2017, Westin et al., 2014), we identified and validated a 121-gene expression signature that can distinguish HPD patients from non-HPD patients. This may have significant clinical predictive value to identify patients who are suitable for anti-PD-1/anti-PD-L1 immunotherapy. Having validated this gene set, we examined whether there exists any mechanism that might explain its association with HPD. Interestingly, most of these genes (70 of 121) belonged to gene sets that we identified as significant to different aspects of the HPD tumors in our samples. Specifically, these genes could be classified into the following six categories that were described above as important contributors to the HPD phenotype (FIG. 18): (1) somatic mutated gene sets; (2) oncogenic pathways of IGF-1, ERK/MAPK, PI3K/AKT, and TGF-β; (3) immune checkpoint genes; (4) ILC3 population marker genes; (5) marker genes for other immune populations like monocytes, CD4 T cells, and dendritic cells; and (6) differentially expressed genes in post-anti-PD-1 HPD tumors versus pre-anti-PD-1 non-HPD tumors. Thus, a significant portion of these HPD signature genes could be involved in the critical biological processes important to tumor evolution, infiltrated immune cells, and tumor-microenvironment interactions. However, although we validated the 121-gene set, more patient cohorts subjected to anti-PD-1 therapy that contain HPD and non-HPD patients are needed for prospective validation.

Figure 24:
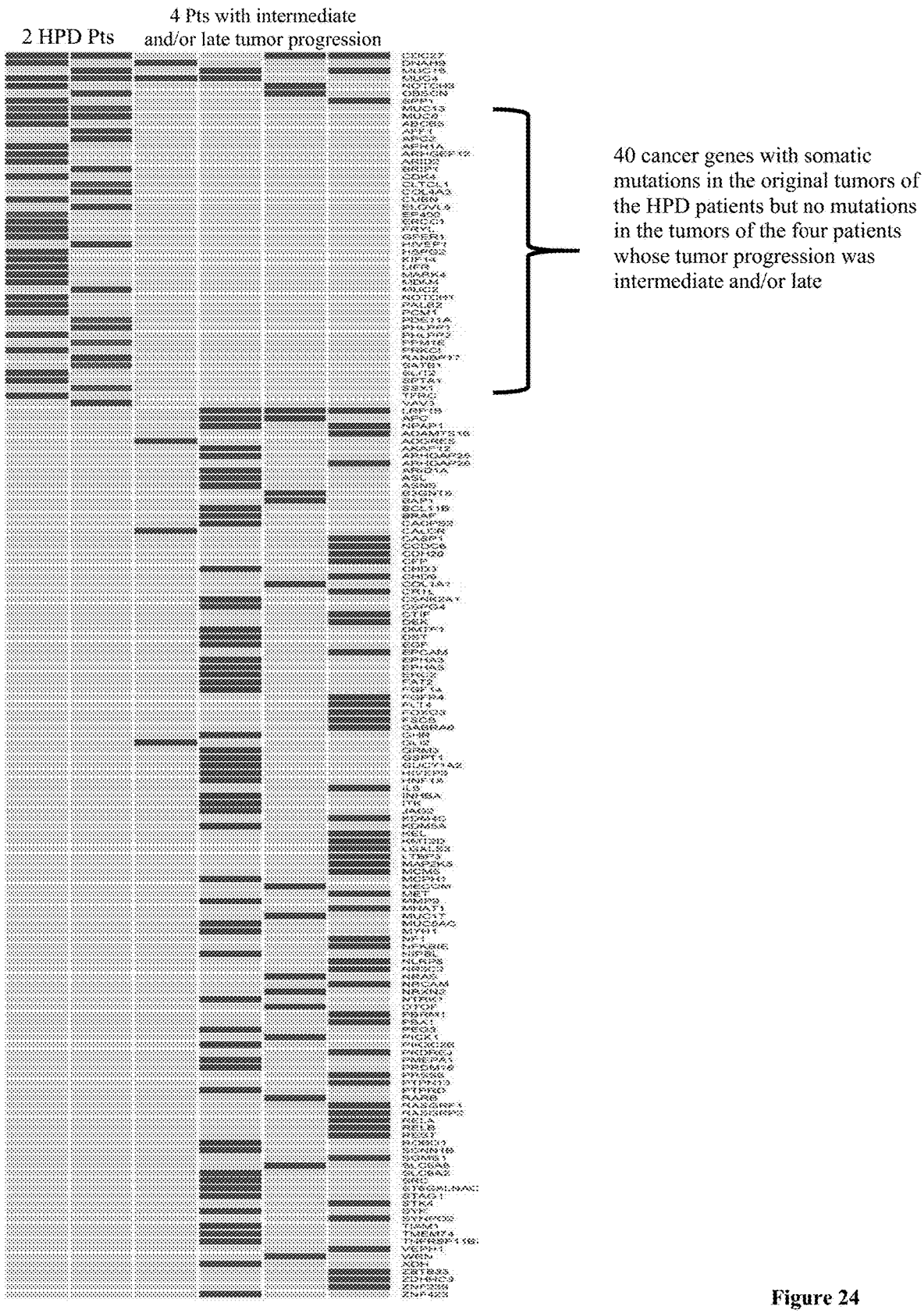
FIG. 24 Comparison of the somatic mutation profiles of pretreatment tumor samples between HPD patients and a subset of non-HPD patients. Related to FIG. 9. Mutation analysis showed that 40 cancer genes had somatic mutations in the original tumors of the HPD patients but no mutations in the tumors of the patients whose tumor progression was intermediate and/or late.
Figure 25:
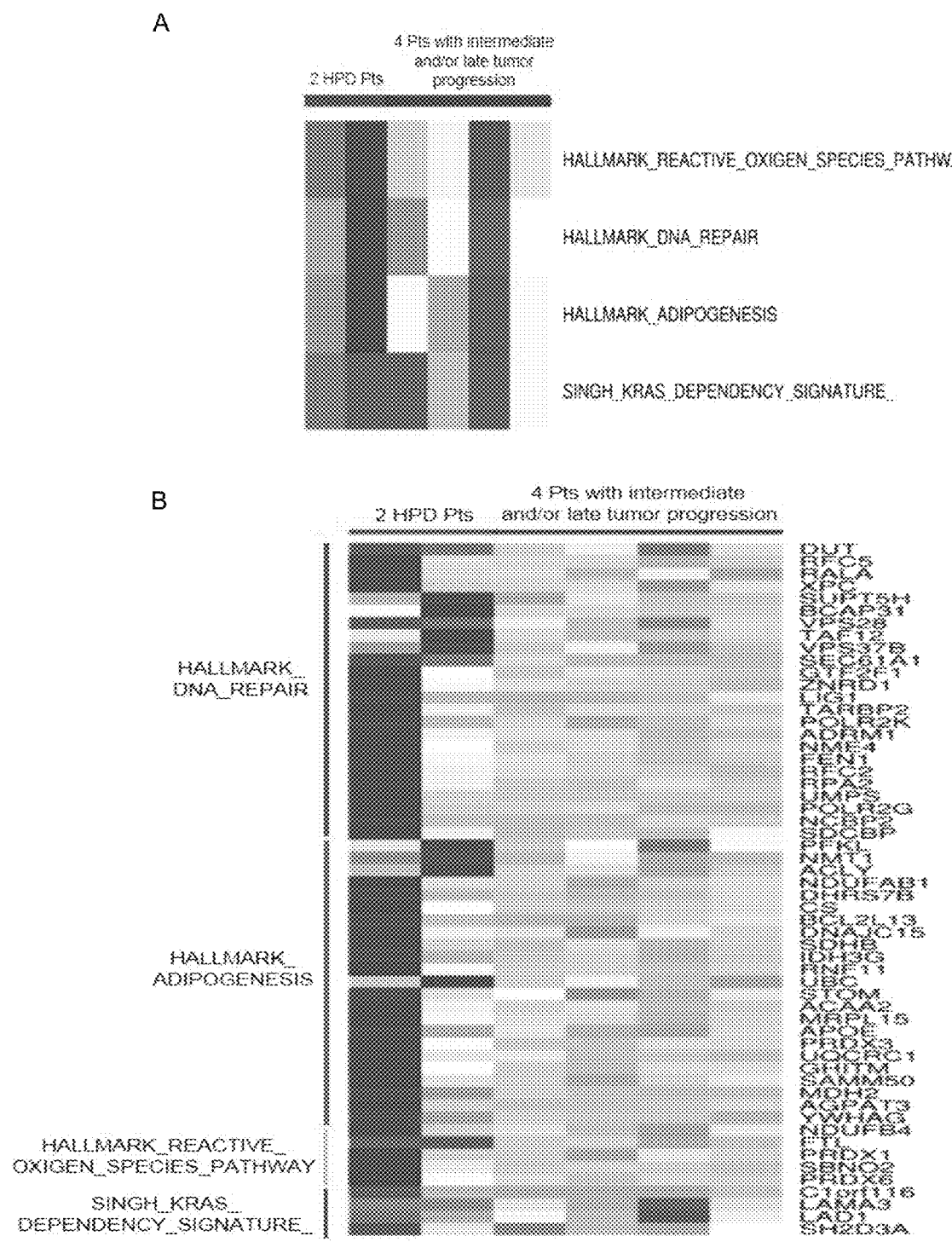
FIG. 25 GSVA analysis of the transcriptional profiles of pretreatment tumor samples between HPD patients and a subset of non-HPD patients. Related to FIG. 9. (A) Four gene sets were significantly altered in the tumors of HPD patients compared to the patients with intermediate and/or late tumor progression; (B) The corresponding gene expression changes of the above significantly altered pathways were also shown.
Figure 26:
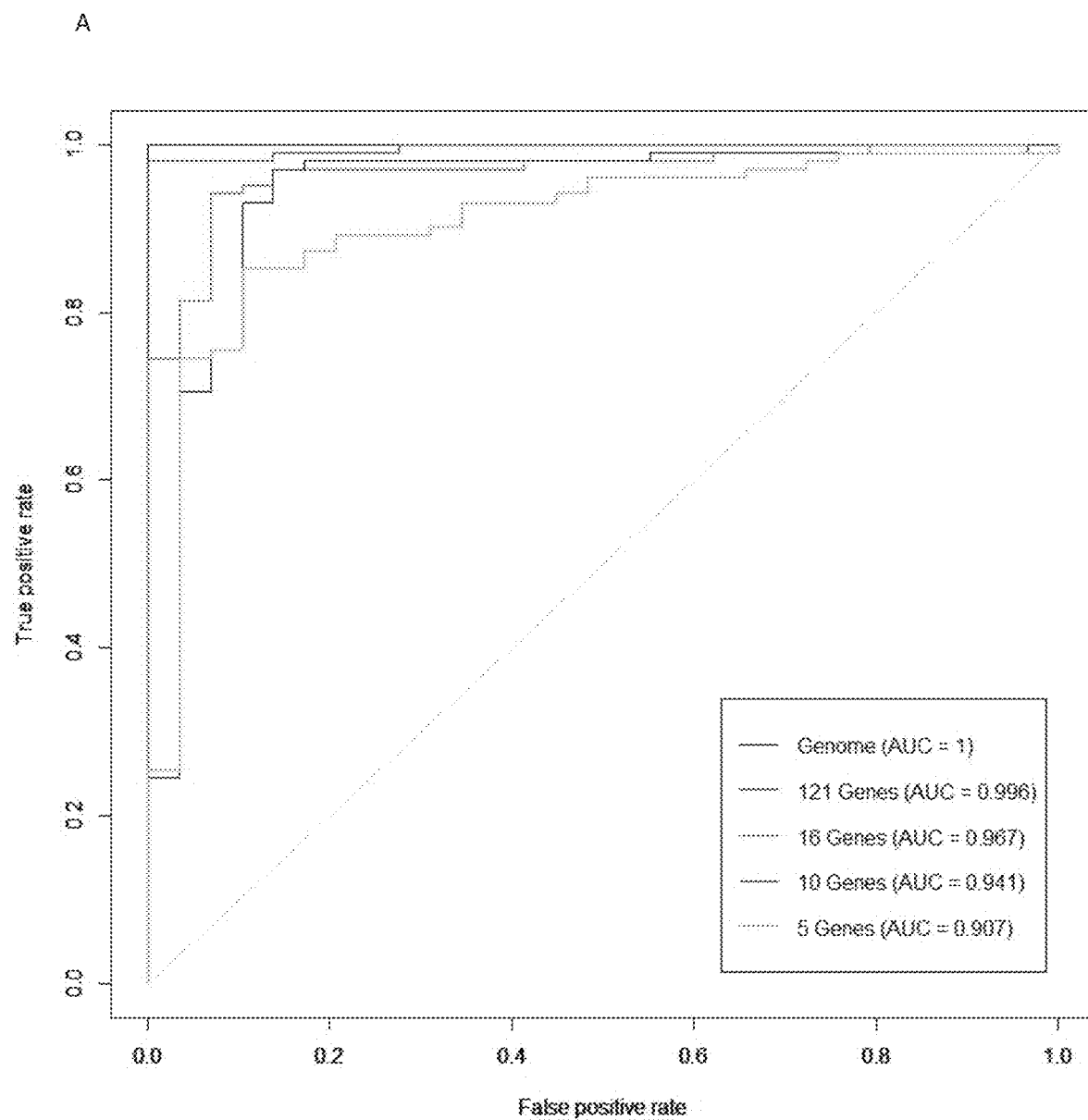
FIG. 26 (A) Performances of the 121-gene set classifier and subset genes from the 121-gene in TCGA BLCA (Bladder carcinoma) dataset. Black line represents that all genes in genome are used as variables in prediction model. Red line represents that 121-gene set classifier is used as variables in prediction model. Green line represents that cancer type specific subset genes (given in Table 7) from the 121-gene are used as variables in prediction model. Blue and turquoise lines represent that different portions of cancer type specific subset genes are used as variables in prediction model.
Figure 26:
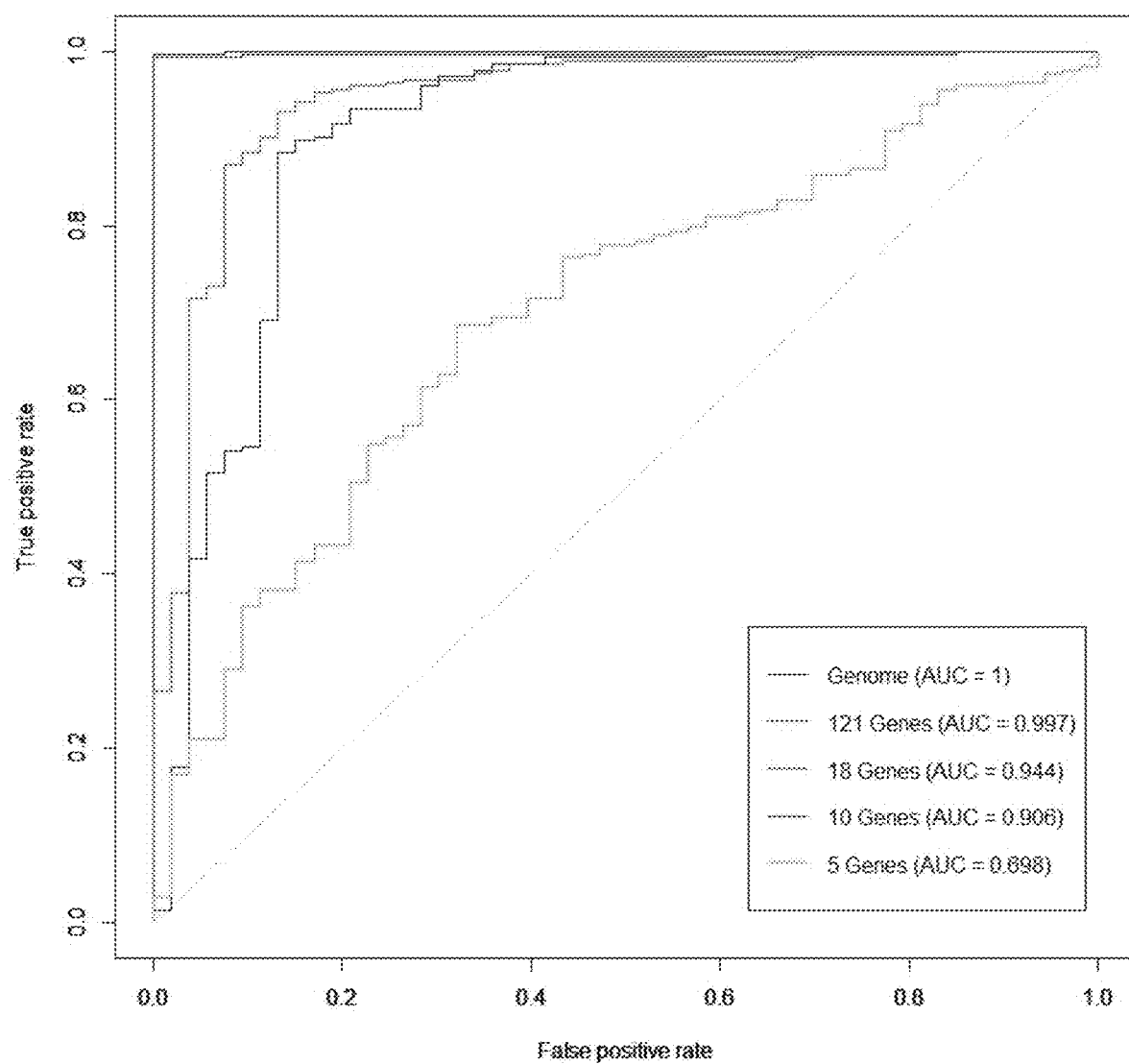

To better define HPD, especially to differentiate HPD from intermediate and/or late tumor progression, we compared the mutational and gene expression of the two original samples in our study with the pre-treatment tumor samples of the four patients (#28, #9, #26, #38) who developed intermediate and/or late tumor progression (Table 5). Mutation analysis showed that 40 cancer genes had nonsilent somatic mutations in the original tumors of the HPD patients but no mutations in the tumors of the patients whose tumor progression was intermediate and/or late (FIG. 24). These genes include, for example, MUC13, MUC6, APC2, ARID2, CDK4, EP400, MARK4, MDM4, MUC2, NOTCH1, and SLIT2. Previous research demonstrated that MDM4 alteration was significantly associated with hyperprogression in patients subjected to immunotherapy (Kato et al., 2017), which was consistent with our results. We tabulated the information of these 40 HPD-associated cancer genes in Table 6. At the transcriptome level, GSVA identified four gene sets from the MsigDB database that were significantly altered in the tumors of HPD patients compared with the patients with intermediate and/or late tumor progression. These gene sets were: HALLMARK_REACTIVE_OXIGEN-SPECIES_PATHWAY, HALLMARK_DNA_REPAIR, HALLMARK_ADIPOGENESIS, and SINGH_KRAS-DEPENDENCY_SIGNATURE. The first three pathways, i.e., the reactive oxygen species pathway, the DNA repair pathway, and the adipogenesis pathway, were significantly inhibited, whereas the KRAS signaling pathway was significantly activated in the tumors of HPD patients relative to the patients with intermediate and/or late tumor progression (FIG. 25A). The corresponding gene expression changes of the above significantly altered pathways were also shown (FIG. 25B). Together, these mutational and transcriptional changes of the tumors between the HPD and the intermediate/late tumor progression patients may contribute to the better characterization of the HPD condition.

TABLE 5

The clinical information of the 51 melanoma patients subjected to nivolumab immunotherapy from the CA209-038 study, among whom 21 patients had PFS less than two months together with post-therapy tumor progression phenotypes. Related to FIG. 9.

| Patient ID | Sample | Sample Type | PFS Censorship | Clinical Phenotype | PFS (days) | HPD status |
|---|---|---|---|---|---|---|
| Pt103 | Pt103_Pre | Pre-anti-PD-1 tumor | 0 | PROGRESSION | 50 | HPD |
| Pt106 | Pt106_Pre | Pre-anti-PD-1 tumor | 0 | PROGRESSION | 56 | HPD |
| Pt11 | Pt11_Pre | Pre-anti-PD-1 tumor | 0 | PROGRESSION | 59 | HPD |
| Pt17 | Pt17_Pre | Pre-anti-PD-1 tumor | 0 | PROGRESSION | 48 | HPD |
| Pt' | Pt1_Pre | Pre-anti-PD-1 tumor | 0 | PROGRESSION | 54 | HPD |
| Pt24 | Pt24_Pre | Pre-anti-PD-1 tumor | 0 | PROGRESSION | 50 | HPD |
| Pt27 | Pt27_Pre | Pre-anti-PD-1 tumor | 0 | PROGRESSION | 50 | HPD |
| Pt29 | Pt29_Pre | Pre-anti-PD-1 tumor | 0 | PROGRESSION | 50 | HPD |
| Pt31 | Pt31_Pre | Pre-anti-PD-1 tumor | 0 | PROGRESSION | 50 | HPD |
| Pt39 | Pt39_Pre | Pre-anti-PD-1 tumor | 0 | PROGRESSION | 57 | HPD |
| Pt46 | Pt46_Pre | Pre-anti-PD-1 tumor | 0 | PROGRESSION | 51 | HPD |
| Pt47 | Pt47_Pre | Pre-anti-PD-1 tumor | 0 | PROGRESSION | 57 | HPD |
| Pt52 | Pt52_Pre | Pre-anti-PD-1 tumor | 0 | PROGRESSION | 57 | HPD |
| Pt5 | Pt5_Pre | Pre-anti-PD-1 tumor | 0 | PROGRESSION | 56 | HPD |
| Pt62 | Pt62_Pre | Pre-anti-PD-1 tumor | 0 | PROGRESSION | 56 | HPD |
| Pt66 | Pt66_Pre | Pre-anti-PD-1 tumor | 0 | PROGRESSION | 59 | HPD |
| Pt78 | Pt78_Pre | Pre-anti-PD-1 tumor | 0 | PROGRESSION | 50 | HPD |
| Pt84 | Pt84_Pre | Pre-anti-PD-1 tumor | 0 | PROGRESSION | 50 | HPD |
| Pt85 | Pt85_Pre | Pre-anti-PD-1 tumor | 0 | PROGRESSION | 49 | HPD |
| Pt8 | Pt8_Pre | Pre-anti-PD-1 tumor | 0 | PROGRESSION | 52 | HPD |
| Pt90 | Pt90_Pre | Pre-anti-PD-1 tumor | 0 | PROGRESSION | 44 | HPD |
| Pt101 | Pt101_Pre | Pre-anti-PD-1 tumor | 0 | PARTIAL RESPONSE | 612 | nonHPD |
| Pt10 | Pt10_Pre | Pre-anti-PD-1 tumor | 0 | STABLE DISEASE | 119 | nonHPD |
| Pt18 | Pt18_Pre | Pre-anti-PD-1 tumor | 0 | NA | 519 | nonHPD |
| Pt23 | Pt23_Pre | Pre-anti-PD-1 tumor | 0 | DEATH PRIOR TO DISEASE ASSESSMENT | 52 | nonHPD |
| Pt26 | Pt26_Pre | Pre-anti-PD-1 tumor | 0 | PROGRESSION | 294 | nonHPD |
| Pt28 | Pt28_Pre | Pre-anti-PD-1 tumor | 0 | PROGRESSION | 61 | nonHPD |
| Pt2 | Pt2_Pre | Pre-anti-PD-1 tumor | 1 | STABLE DISEASE | 115 | nonHPD |
| Pt30 | Pt30_Pre | Pre-anti-PD-1 tumor | 0 | PARTIAL RESPONSE | 603 | nonHPD |
| Pt34 | Pt34_Pre | Pre-anti-PD-1 tumor | 1 | NA | 834 | nonHPD |
| Pt36 | Pt36_Pre | Pre-anti-PD-1 tumor | 1 | NA | 737 | nonHPD |
| Pt37 | Pt37_Pre | Pre-anti-PD-1 tumor | 0 | STABLE DISEASE | 176 | nonHPD |
| Pt38 | Pt38_Pre | Pre-anti-PD-1 tumor | 0 | PROGRESSION | 167 | nonHPD |
| Pt3 | Pt3_Pre | Pre-anti-PD-1 tumor | 0 | PARTIAL RESPONSE | 583 | nonHPD |
| Pt44 | Pt44_Pre | Pre-anti-PD-1 tumor | 0 | PARTIAL RESPONSE | 560 | nonHPD |
| Pt48 | Pt48_Pre | Pre-anti-PD-1 tumor | 1 | NA | 1046 | nonHPD |

TABLE 5-continued

The clinical information of the 51 melanoma patients subjected to nivolumab immunotherapy from the CA209-038 study, among whom 21 patients had PFS less than two months together with post-therapy tumor progression phenotypes. Related to FIG. 9.

| Patient ID | Sample | Sample Type | PFS Censorship | Clinical Phenotype | PFS (days) | HPD status |
|---|---|---|---|---|---|---|
| Pt49 | Pt49_Pre | Pre-anti-PD-1 tumor | 1 | PARTIAL RESPONSE | 827 | nonHPD |
| Pt4 | Pt4_Pre | Pre-anti-PD-1 tumor | 0 | STABLE DISEASE | 175 | nonHPD |
| Pt59 | Pt59_Pre | Pre-anti-PD-1 tumor | 0 | STABLE DISEASE | 111 | nonHPD |
| Pt65 | Pt65_Pre | Pre-anti-PD-1 tumor | 1 | STABLE DISEASE | 280 | nonHPD |
| Pt67 | Pt67_Pre | Pre-anti-PD-1 tumor | 0 | STABLE DISEASE | 281 | nonHPD |
| Pt72 | Pt72_Pre | Pre-anti-PD-1 tumor | 0 | PARTIAL RESPONSE | 333 | nonHPD |
| Pt76 | Pt76_Pre | Pre-anti-PD-1 tumor | 0 | NA | 10 | nonHPD |
| Pt77 | Pt77_Pre | Pre-anti-PD-1 tumor | 0 | STABLE DISEASE | 163 | nonHPD |
| Pt79 | Pt79_Pre | Pre-anti-PD-1 tumor | 0 | STABLE DISEASE | 171 | nonHPD |
| Pt82 | Pt82_Pre | Pre-anti-PD-1 tumor | 0 | STABLE DISEASE | 220 | nonHPD |
| Pt89 | Pt89_Pre | Pre-anti-PD-1 tumor | 0 | STABLE DISEASE | 219 | nonHPD |
| Pt92 | Pt92_Pre | Pre-anti-PD-1 tumor | 0 | STABLE DISEASE | 190 | nonHPD |
| Pt94 | Pt94_Pre | Pre-anti-PD-1 tumor | 1 | COMPLETE RESPONSE | 729 | nonHPD |
| Pt98 | Pt98_Pre | Pre-anti-PD-1 tumor | 0 | STABLE DISEASE | 408 | nonHPD |
| Pt9 | Pt9_Pre | Pre-anti-PD-1 tumor | 0 | PROGRESSION | 66 | nonHPD |

TABLE 6

The information of the 40 HPD associated cancer genes having nonsilent somatic mutations in the original tumors of the HPD patients but no mutations in the tumors of the patients whose tumor progression was intermediate and/or late. Related to FIG. 9.

| Symbol | Entrez Gene Name | Location | Type(s) |
|---|---|---|---|
| ABCB5 | ATP binding cassette subfamily B member 5 | Plasma Membrane | transporter |
| AFF1 | AF4/FMR2 family member 1 | Nucleus | transcription regulator |
| APC2 | APC2, WNT signaling pathway regulator | Cytoplasm | enzyme |
| APH1A | aph-1 homolog A, gamma-secretase subunit | Cytoplasm | Peptidase |
| ARHGEF12 | Rho guanine nucleotide exchange factor 12 | Cytoplasm | other |
| ARID2 | AT-rich interaction domain 2 | Nucleus | transcription regulator |
| BRIP1 | BRCA1 interacting protein C-terminal helicase 1 | Nucleus | enzyme |
| CDK4 | cyclin dependent kinase 4 | Nucleus | kinase |
| CLTCL1 | clathrin heavy chain like 1 | Plasma Membrane | other |
| COL4A3 | collagen type IV alpha 3 chain | Extracellular Space | other |
| CUBN | cubilin | Plasma Membrane | transmembrane receptor |
| ELOVL5 | ELOVL fatty acid elongase 5 | Cytoplasm | enzyme |
| EP400 | E1A binding protein p400 | Nucleus | other |
| ERCC1 | ERCC excision repair 1, endonuclease non-catalytic subunit | Nucleus | enzyme |
| FRYL | FRY like transcription coactivator | Other | other |
| GPER1 | G protein-coupled estrogen receptor 1 | Plasma Membrane | G-protein coupled receptor |
| HIVEP1 | Human immunodeficiency virus type 1 enhancer binding protein 1 | Nucleus | transcription regulator |
| HSPG2 | heparan sulfate proteoglycan 2 | Extracellular Space | enzyme |
| K1F14 | kinesin family member 14 | Cytoplasm | enzyme |
| LIFR | LIF receptor alpha | Plasma Membrane | transmembrane receptor |
| MARK4 | microtubule affinity regulating kinase 4 | Cytoplasm | kinase |
| MDM4 | MDM4, p53 regulator | Nucleus | enzyme |
| MUC13 | mucin 13, cell surface associated | Extracellular Space | other |
| MUC2 | mucin 2, oligomeric mucus/gel-forming | Extracellular Space | other |
| MUC6 | mucin 6, oligomeric mucus/gel-forming | Extracellular Space | other |
| NOTCH1 | Notch 1 | Plasma Membrane | transcription regulator |
| PALB2 | partner and localizer of BRCA2 | Nucleus | other |
| PCM1 | pericentriolar material 1 | Cytoplasm | other |
| PDE11A | phosphodiesterase 11A | Cytoplasm | enzyme |

TABLE 6-continued

The information of the 40 HPD associated cancer genes having nonsilent somatic mutations in the original tumors of the HPD patients but no mutations in the tumors of the patients whose tumor progression was intermediate and/or late. Related to FIG. 9.

| Symbol | Entrez Gene Name | Location | Type(s) |
|---|---|---|---|
| PHLPP1 | PH domain and leucine rich repeat protein phosphatase 1 | Cytoplasm | enzyme |
| PHLPP2 | PH domain and leucine rich repeat protein phosphatase 2 | Cytoplasm | enzyme |
| PPM1E | protein phosphatase, Mg2+/Mn2+ dependent 1E | Nucleus | Phosphatase |
| PRKC1 | protein kinase C iota | Cytoplasm | Kinase |
| RANBP17 | RAN binding protein 17 | Nucleus | transporter |
| SATB1 | SATB homeobox 1 | Nucleus | transcription regulator |
| SLIT2 | slit guidance ligand 2 | Extracellular Space | other |
| SPTA 1 | spectrin alpha, erythrocytic 1 | Cytoplasm | other |
| SSX1 | SSX family member 1 | Nucleus | transcription regulator |
| TFRC | transferrin receptor | Plasma Membrane | transporter |
| VAV3 | vav guanine nucleotide exchange factor 3 | Extracellular Space | cytokine |

Overall, our comprehensive analysis of HPD tumors after anti-PD-1 therapy and pre-therapy tumors identified the genomics and immune factors contributing to the hyperprogression phenotypes, such as deleterious somatic mutations in important tumor suppressors such as TSC2 and VHL, downregulated antigen-processing genes, and upregulated immune checkpoints or modulators other than PD-1/PD-L1. We also identified immune cell populations with significant activity changes in the HPD tumors; particularly the ILC subset, ILC3, was found to be activated in the HPD tumors after anti-PD-1 treatment. A gene expression signature for HPD tumors was also identified and validated using our samples and publicly available datasets. Our findings may contribute to understanding the mechanisms of the development of HPD after anti-PD-1 treatment, which is important to identify patients at high risk of developing HPD.

TABLE 7

The information of the gene subsets out of the 121-gene signature predictive of HPD patients. The gene subsets may serve as prognostic biomarkers and show significant association with overall survival in each of the 13 TCGA cancer types.

| TCGA cancers | Abbreviation | Cancer type specific prognostic biomarkers from 121-gene HPD signature | | | | | | | | | |
|---|---|---|---|---|---|---|---|---|---|---|---|
| Bladder carcinoma | BLCA | ARMC9 | CARD8 | CD96 | CLSTN3 | CREBZF | FAM104B | HIVEP1 | OBSCN | PPP2R3C | SERPINF1 |
| Breast invasive carcinoma | BRCA | ANKS6 | ARL1 | CCNT1 | CD96 | CPT1A | DIAPH1 | GPR18 | HPGDS | LRP6 | MEF2D |
| Colon adenocarcinoma | COAD | BAZ2A | CD63 | CYP2D6 | DGKD | ELK4 | FAHD1 | GALNT2 | | | |
| Esorphageal carcinoma | ESCA | ANKS6 | ANKA5 | CCNA1 | COL4A1 | CPT1A | DGKD | FUCA2 | HIVEP2 | KDR | LRP6 |
| Head and Neck squamous cell carcinoma | HNSC | CCNA1 | CHD4 | CTLA4 | CYP2D6 | FAHD1 | HIVEPI | TNFRSF25 | YWHAQ | | |
| Kidney renal clear cell carcinoma | KIRC | AFF1 | ANKS6 | ATF71P | ATP11C | ATP5L | CAMSAP1 | CCNA1 | CCNT1 | CD63 | CPT1A |
| | | FAHD1 | FBXL17 | FPGT | FUBP3 | GALNT2 | GAPVD1 | GOLIM4 | GPR18 | HACH | HHLA3 |
| | | MAGEH1 | MEF2D | NFE2L2 | NPLOC4 | NSD1 | OBFC1 | OTUD7B | PPM1L | PTPN3 | RANGAP1 |
| | | TLN1 | TNFRSF25 | TNKS2 | TRIP12 | WDR44 | YWHAE | | | | |
| Brain Lower Grade Glioma | LGG | ACOT1 | AFF1 | ARMC9 | BAZ1B | CCNA1 | COL4A1 | COL4A2 | CSNK1G1 | GALNT2 | HSPG2 |
| Liver hepatocellular carcinoma | LIHC | CORO1C | FPGT | HADH | KLHDC8B | MAGEH1 | SLC38A6 | SPP1 | | | |
| Lung adenocarcinoma | LUAD | C0L4A1 | COL4A2 | CPT1A | NOTCH3 | NPLOC4 | SLC27A1 | SPP1 | YWHAQ | | |
| Lung squamous cell carcinoma | LUSC | ANXA5 | DIAPH1 | E1D2 | GALNT2 | GOLM4 | PHF8 | TMEM99 | | | |
| Pancreatic adenocarcinomia | PAAD | CARD8 | CLSTN3 | COMMD9 | CYP2D6 | DIAPH1 | FAM104B | GALNT10 | MAGEH1 | NPLOC4 | OTUD7B |

TABLE 7-continued

The information of the gene subsets out of the 121-gene signature predictive of HPD patients. The gene subsets may serve as prognostic biomarkers and show significant association with overall survival in each of the 13 TCGA cancer types.

| Skin cutaneous melanoma | SKCM | ANKS6 | ARMC9 | BAZ1B | BAZ2A | CD63 | CHD4 | FUBP3 | FUCA2 | LGALSI2 | NUP188 |
|---|---|---|---|---|---|---|---|---|---|---|---|
| Stomach adeno-carcinoma | STAD | CD63 | CHD4 | EID2 | FAHD1 | GAPVD1 | MEF2D | TEX261 | VHL | | |

| TCGA cancers | Abbreviation | Cancer type specific prognostic biomarkers from 121-gene HPD signature | | | | | | | |
|---|---|---|---|---|---|---|---|---|---|
| Bladder carcinoma | BLCA | SLC27A1 | SLC6A6 | TCF4 | TIMM8B | VHL | YWHAQ | | |
| Breast invasive carcinoma | BRCA | NSD1 | NUP188 | SLC27A1 | TCF4 | TEX261 | TRIP12 | UBTF | ZNF878 |
| Colon adeno-carcinoma | COAD | | | | | | | | |
| Esorphageal carcinoma | ESCA | NOTCH3 | OBFC1 | OBSCN | SORT1 | TEX261 | TGOLN2 | | |
| Head and Neck squamous cell carcinoma | HNSG | | | | | | | | |
| Kidney renal clear cell carcinoma | KIRC | CREBZF | CSNK1G1 | CTLA4 | CYP2D6 | DIAPH1 | ELK4 | EP300 | ERNI |
| | | HIVEP1 | HMBS | HSPG2 | KDR | KIAA2018 | LGALS12 | LNPEP | LRP6 |
| | | SATB1 | SERPINF1 | SETX | SLC38A6 | SLC6A6 | SPIN2A | TCF4 | TGOLN2 |
| Brain Lower Grade Glioma | LGG | KDR | MTIF3 | NSD1 | SERPINF1 | SLC6A6 | SNAPC4 | SPP1 | TSPAN3 |
| Liver hepatocellular carcinoma | LIHC | | | | | | | | |
| Lung adeno-carcinoma | LUAD | | | | | | | | |
| Lung squamous cell carcinoma | LUSC | | | | | | | | |
| Pancreatic adeno-carcinomia | PAAD | SATB1 | SLC25A34 | SMURF1 | SNAPC4 | TCF4 | TMEM99 | TSC2 | UBTF |
| Skin cutaneous melanoma | SKCM | SPEN | TEX261 | TRIO | YWHAE | | | | |
| Stomach adeno-carcinoma | STAD | | | | | | | | |

Data and Software Availability

The WES and RNA-seq raw sequence reads data from the before and after anti-PD-1 immunotherapy FFPE samples from the two cancer patients (4 FFPE samples) have been deposited in the Sequence Read Archive under accession number of PRJNA503522 (ID:503522), incorporated by reference in its entirety.

Transparent Methods:

Whole-Exome Sequencing (WES) and RNA-Seq Experimentation and Data Analyses

For each set of paired tumor samples, a section of formalin-fixed tissue was examined with hematoxylin and eosin (H&E) staining to confirm the presence of tumor and determine the relative tumor burden. At least five 10-mm FFPE slides were used for each tumor specimen, from which DNA and RNA were purified by a commercial vendor (Omega Bio-tek, Inc., Norcross, GA 30071) and subjected to WES and RNA-seq after library purification. The Illumina Nextera Rapid Capture Exome kit was used for the preparation of exome libraries, which were sequenced to the average depth of 150× coverage in the paired end 150 bp (PE150) mode with a HiSeq 4000 system. The Illumina TruSeq RNA Access kit was used for the preparation of total RNA libraries that were sequenced to the average depth of 75 million reads in the paired end 100 bp (PE100) mode using the HiSeq 2500 system.

The WES short reads were aligned to a reference genome (NCBI human genome assembly hg19) using the BWA (Burrows-Wheeler Aligner) program (Ll and Durbin, 2009). Each alignment was assigned a mapping quality score by BWA (Ll and Durbin, 2009), which generated a Phred-scaled probability that the alignment is correct. Reads with low mapping quality scores (<5) were removed to reduce the false positive rate. The PCR duplicates were detected and removed using Picard software. Local realignment of the BWA-aligned reads was performed using the Genome Analysis Toolkit (GATK) (McKenna et al., 2010). VarScan 2 (Koboldt et al., 2012) was used to identify somatic variants based on the local realignment results comparing each tumor with the two reference blood samples. Default parameters in VarScan 2 were used. The lists of shared SNVs/indels were then annotated using ANNOVAR (Wang et al., 2010). Single nucleotide polymorphisms (SNPs) were filtered against dbSNP version 142 (dbSNP 142). Plots of mutations were generated using the "oncoPrint" function provided by the R package—ComplexHeatmap (Gu et al., 2016). To identify somatic mutations with the most significant functional consequences, we predicted the impact of the mutations on HPD tumors using the bioinformatics programs SIFT, PolyPhen-2, and FATHMM according to our previous approaches (Xiong et al., 2015). Network analysis of the eleven genes having deleterious mutations in HPD tumors was performed and graphically depicted using Ingenuity Pathway Analysis software (IPA, QIAGEN Inc.). Mapping of the p.Y1611S mutation to the 3D structure of the TSC2 protein was performed using MuPIT software (Niknafs et al., 2013). The bioinformatics tools SciClone (Miller et al., 2014) and Clonevol (Dang et al., 2017) were used to identify the clonal structures of the paired tumors of the two HPD patients. Plots of the clonal mutation clusters were generated using the fishplot software feature (Miller et al., 2016).

RNA-seq sample quality was analyzed using the FastQC program via the Babraham Bioinformatics website. Raw sequence data reads in fasta format were first processed through Perl scripts (Haas et al., 2013). Data were then refined by removing reads containing adapter, poly-N, or low-quality reads (Pei et al., 2016; Wang et al., 2015). All downstream analyses were based on refined data. The "rsem prepare reference" script of the RSEM package was used to generate reference transcript sequences by using the gene annotation file (GTF) format and the full genome sequence (FASTA) format of human GRCh37 assembly. All of the quality reads of different samples were mapped to generated reference transcript sequences using the Bowtie-2 program (Langmead et al., 2009) to determine the identity between cDNA sequences and corresponding genomic exons in regions of exact matches. The "rsem calculate expression" script of RSEM was used to analyze both the alignment of reads against reference transcript sequences and the calculation of relative abundances. Normalized gene expression values in TPM (Transcripts Per Kilobase Million) were used as input of the AltAnalyze software (Olsson et al., 2016) for differential gene expression analysis. FDR (False discovery rate) corrected P-values of less than 0.05 were used as criteria for significantly regulated genes.

To perform oncogenic pathway or network analysis, the list of differentially expressed genes between paired pre- and post-anti-PD-1 therapy tumors of the two patients was analyzed through the use of IPA. The GSVA (Gene Set Variation Analysis) (Hanzelmann et al., 2013) and GSEA (Gene Set Enrichment Analysis) (Subramanian et al., 2005) approaches were used to analyze the activity and enrichment of immune cell populations, respectively. GSEA analysis was performed for pre-ranked differentially expressed genes using the option 'GseaPreranked'.

One thousand permutations were used to calculate significance. A gene set was considered to be significantly enriched in one of the two groups when the P value was lower than 0.05 and the FDR was lower than 0.25 for the corresponding gene set. For inflammatory pathway analysis, we performed a focused gene expression study by analyzing the changes of the inflammatory related genes included in the Hallmark gene set for inflammatory response named "HALLMARK_INFLAMMATORY_RESPONSE" downloaded from the MSigDB database (Liberzon et al., 2015; Liberzon et al., 2011). The GSVA approach (Hanzelmann et al., 2013) was used to characterize the activity of inflammation pathways in the post-anti-PD-1 treatment HPD tumors vs pre-treatment tumors. All heatmaps of gene expression were generated using the R package—heatmap3.

Tumor Immunogenicity Analysis

Immunogenicity of the pre-anti-PD-1 treatment tumors and post-treatment HPD tumors was analyzed using published criteria (Charoentong et al., 2017; Hakimi et al., 2016). The immunophenoscore (IPS) was calculated on an arbitrary 0-10 scale based on the sum of the weighted averaged Z score of the four categories shown in FIG. 5 in accordance to the previous methods (Charoentong et al., 2017; Tappeiner et al., 2017). Briefly, the four categories include 20 single factors such as the presence of specific immune cell types along with the abundance of MHC molecules, or molecules known to act as immunoinhibitors or immunostimulators. For each determinant, a sample-wise Z score from gene expression data was calculated. For the six cell types, an average Z score from the corresponding metagenes was calculated. The metagenes were defined previously as non-overlapping sets of genes that are representative for specific immune cell subpopulations and are not expressed in normal tissue (Charoentong et al., 2017). The detailed list of genes included in the metagenes were available from the same literature (Charoentong et al., 2017). The determinants were then divided into four categories-effector cells (activated CD4+ or CD8+ T cells and effector memory CD4+ T cells or CD8+ T cells), and suppressive cells (Tregs and MDSCs [myeloid-derived suppressor cells]), MHC-related molecules, and checkpoints or immunomodulators are color-coded in the outer part of the wheel (red: positive Z score, blue: negative Z score).

Development and Validation of an HPD Classifier Based on Gene Expression Data

Previously, no gene expression signature had been identified to predict which patients might develop HPD after receiving anti-PD-1 immunotherapy. To identify such predictors, we analyzed the publicly available gene expression data sets of the anti-PD-1 immunotherapy studies that may contain subsets of patients that acquired HPD. Similar to previous studies (Champiat et al., 2017; Kato et al., 2017; Saada-Bouzid et al., 2017), we defined HPD as (1) progression at first restaging on therapy, (2) increase in tumor size >50%, and (3) >2-fold increase in tumor growth rate (TGR). Based on these criteria, we identified two cohorts in these datasets that received anti-PD-1 treatment and contained patients that developed putative HPD. The first study (Accession #"GSE52562" in the GEO database) performed gene expression profiling of tumor biopsies before and after pidilizumab (a humanized anti-PD-1 monoclonal antibody, also called "CT-011") therapy in patients with relapsed follicular lymphoma (Westin et al., 2014). Previously, it was suggested that binding to PD-1 was the main driver for pidilizumab's activity. Recent analyses show that pidilizumab binds to a hypoglycosylated/nonglycosylated form of PD-1 that is present on a distinct subpopulation of exhausted T cells (Fried et al., 2018). Nevertheless, multiple studies have shown that pidilizumab can affect PD-1 function either through binding or other mechanisms, so pidilizumab treatment is still considered as anti-PD-1 therapy (Abdin et al., 2018; Benson et al., 2010; Jelinek and Hajek, 2016; Mkrtichyan et al., 2011; Rosenblatt et al., 2011; Westin et al., 2014). Two of eighteen follicular lymphoma patients from this study had PFS less than two months after anti-PD-1 treatment. These two patients were classified as HPD patients, while the other sixteen were non-HPD patients (Table 3). To develop an HPD-associated gene expression signature, the pre-therapy tumor expression data of our two HPD patients were combined with the pre-treatment tumor expression data of the two HPD patients and sixteen non-HPD patients from the GSE52562 study. This was used as the HPD signature discovery dataset (called "Dataset_1"). Another study (quoted as "CA209-038") assessed transcriptome changes in tumors from the patients with advanced melanoma before and after nivolumab immunotherapy (Riaz et al., 2017). This CA209-038 study had 21 advanced melanoma patients having PFS<2 months after anti-PD-1 immunotherapy. Therefore, these 21 patients were classified as the HPD patients while the other 31 patients were classified as non-HPD patients (Table 5). These 51 patients had pre-therapy gene expression data available, and this dataset was used as the validation dataset (called "Dataset_2").

Based on the genome-wide expression data of Dataset_1 and Dataset_2, we developed and validated a 121-gene classifier using the cancerclass R package (Budczies et al., 2014).

The performance of the 121-gene set as a classifier was evaluated with the use of receiver-operating-characteristic curves, calculation of AUC (Hanley and McNeil, 1982), and estimates of sensitivity and specificity implemented in the cancerclass R package (Jan et al., 2014). This classification protocol starts with a feature selection step and continues with nearest-centroid classification. Fisher's exact test was used for categorical variables. All confidence intervals are reported as two-sided binomial 95% confidence intervals. Statistical analysis was performed with R software, version 3.2.3 (R Project for Statistical Computing). We also tested the prognostic performance of the 121-gene signature using gene expression data from the TCGA tumor samples in conjunction with the online biomarker validation tool and database-SurvExpress (Aguirre-Gamboa et al., 2013). Specifically, Kaplan-Meier survival analyses were implemented to estimate the survival functions after the samples were classified into two risk groups according to their risk scores based on the 121-gene set. Differences in survival risk between the two risk groups were assessed using the Mantel-Haenszel log-rank test.

Table S1. The Information of the Nonsilent Somatic Mutations Identified in the Tumors Collected in the Two Patients before and after Anti-PD-1 Treatment with Pembrolizumab, Related to FIGS. 1 and 2 and Table 2, and is incorporated by reference from U.S. Provisional Application No. 62/914,652 in its entirety.

Table S2. The Information of the Nonsilent Somatic Mutations Identified in the Tumors of the Two Patients Before and After Anti-PD-1 Treatment with Pembrolizumab in the Context of Known Cancer Genes Based on a Comprehensive List of Cancer Related Genes. Related to FIG. 1, and is incorporated by reference from U.S. Provisional Application No. 62/914,652 in its entirety.

Table S3. Information of the 96 and 64 Subject-Specific Non-silent Somatic Mutations from 154 Genes in Post-treatment Tumors of Patient 1 and Patient 2, Respectively, Related to FIGS. 2B and 2C and is incorporated by reference from U.S. Provisional Application No. 62/914,652 in its entirety.

REFERENCES

1. Kato S, Goodman A, Walavalkar V, Barkauskas D A, Sharabi A, Kurzrock R. Hyperprogressors after Immunotherapy: Analysis of Genomic Alterations Associated with Accelerated Growth Rate. Clin Cancer Res. 2017; 23(15): 4242-50. Epub 2017/03/30. doi: 10.1158/1078-0432.CCR-16-3133, 1078-0432.CCR-16-3133 [pii]. PubMed PMID: 28351930; PMCID: 5647162.
2. Westin J R, Chu F, Zhang M, Fayad L E, Kwak L W, Fowler N, Romaguera J, Hagemeister F, Fanale M, Samaniego F, Feng L, Baladandayuthapani V, Wang Z, Ma W, Gao Y, Wallace M, Vence L M, Radvanyi L, Muzzafar T, Rotem-Yehudar R, Davis R E, Neelapu S S. Safety and activity of PD1 blockade by pidilizumab in combination with rituximab in patients with relapsed follicular lymphoma: a single group, open-label, phase 2 trial. Lancet Oncol. 2014; 15(1):69-77. Epub 2013/12/18. doi: 10.1016/S1470-2045(13)70551-5 S1470-2045(13)70551-5 [pii]. PubMed PMID: 24332512; PMCID: 3922714.
3. Riaz N, Havel J J, Makarov V, Desrichard A, Urba W J, Sims J S, Hodi F S, Martin-Algarra S, Mandal R, Sharfman W H, Bhatia S, Hwu W J, Gajewski T F, Slingluff C L, Jr., Chowell D, Kendall S M, Chang H, Shah R, Kuo F, Morris L G T, Sidhom J W, Schneck J P, Horak C E, Weinhold N, Chan T A. Tumor and Microenvironment Evolution during Immunotherapy with Nivolumab. Cell. 2017; 171(4):934-49 e15. Epub 2017/10/17. doi: S0092-8674(17)31122-4 [pii]10.1016/j.cell.2017.09.028. PubMed PMID: 29033130; PMCID: 5685550.
4. Budczies J, Kosztyla D, Torne C V, Stenzinger A, Darb-Esfahani S, Dietel M, Denkert C. cancerclass: An R Package for development and validation of diagnostic tests from high-dimensional molecular data. J Stat Software. 2014; 59(1):1-19.
5. Hanley J A, McNeil B J. The meaning and use of the area under a receiver operating characteristic (ROC) curve. Radiology. 1982; 143(1):29-36. Epub 1982/04/01. doi: 10.1148/radiology.143.1.7063747. PubMed PMID: 7063747.
6. Jan B, Kosztyla D, von Törne C, Stenzinger A, Darb-Esfahani S, Dietel M, Denkert C. cancerclass: An R Package for Development and Validation of Diagnostic Tests from High-Dimensional Molecular Data. 2014. 2014; 59(1):19. Epub 2014-08-13. doi: 10.18637/jss.v059.i01.
7. Haas B J, Papanicolaou A, Yassour M, Grabherr M, Blood P D, Bowden J, Couger M B, Eccles D, Li B, Lieber M, MacManes M D, Ott M, Orvis J, Pochet N, Strozzi F, Weeks N, Westerman R, William T, Dewey C N, Henschel R, LeDuc R D, Friedman N, Regev A. De novo transcript sequence reconstruction from RNA-seq using the Trinity platform for reference generation and analysis. Nat Protoc. 2013; 8(8):1494-512. Epub 2013/07/13. doi: 10.1038/nprot.2013.084. PubMed PMID: 23845962; PMCID: 3875132.
8. Pei M, Niu J, Li C, Cao F, Quan S. Identification and expression analysis of genes related to calyx persistence in Korla fragrant pear. BMC Genomics. 2016; 17:132. Epub 2016/02/26. doi: 10.1186/s12864-016-2470-310.1186/s12864-016-2470-3 [pii]. PubMed PMID: 26911295; PMCID: 4765163.
9. Wang X, Xiong M, Lei C, Zhu F. The developmental transcriptome of the synanthropic fly Chrysomya megacephala and insights into olfactory proteins. BMC Genomics. 2015; 16:20. Epub 2015/01/24. doi: 10.1186/s12864-014-1200-ys12864-014-1200-y [pii]. PubMed PMID: 25612629; PMCID: 4311427.
10. Langmead B, Trapnell C, Pop M, Salzberg S L. Ultrafast and memory-efficient alignment of short DNA sequences to the human genome. Genome Biol. 2009; 10(3):R25. Epub 2009/03/06. doi: 10.1186/gb-2009-10-3-r25 gb-2009-10-3-r25 [pii]. PubMed PMID: 19261174; PMCID: 2690996.
11. Aguirre-Gamboa R, Gomez-Rueda H, Martinez-Ledesma E, Martinez-Torteya A, Chacolla-Huaringa R, Rodriguez-Barrientos A, Tamez-Pena J G, Trevino V. SurvExpress: an online biomarker validation tool and database for cancer gene expression data using survival analysis. PLoS One. 2013; 8(9):e74250. Epub 2013/09/26. doi: 10.1371/journal.pone.0074250 PONE-D-13-16634 [pii]. PubMed PMID: 24066126; PMCID: 3774754.

12. Friedman J, Hastie T, Tibshirani R. Regularization Paths for Generalized Linear Models via Coordinate Descent. J Stat Softw. 2010; 33(1):1-22. PubMed PMID: 20808728; PMCID: PMC2929880.
13. Tibshirani R, Bien J, Friedman J, Hastie T, Simon N, Taylor J, Tibshirani R J. Strong rules for discarding predictors in lasso-type problems. Journal of the Royal Statistical Society: Series B (Statistical Methodology). 2012; 74(2):245-66. doi: doi:10.1111/j.1467-9868.2011.01004.x.

Angelova, M., Charoentong, P., Hackl, H., Fischer, M. L., Snajder, R., Krogsdam, A. M., Waldner, M. J., Bindea, G., Mlecnik, B., Galon, J., et al. (2015). Characterization of the immunophenotypes and antigenomes of colorectal cancers reveals distinct tumor escape mechanisms and novel targets for immunotherapy. Genome Biol. 16, 64.

Biton, J., Mansuet-Lupo, A., Pecuchet, N., Alifano, M., Ouakrim, H., Arrondeau, J., Boudou-Rouquette, P., Goldwasser, F., Leroy, K., Goc, J., et al. (2018). TP53, STK11 and EGFR mutations predict tumor immune profile and the response to anti-PD-1 in lung adenocarcinoma. Clin. Cancer Res. 9, 1-14.

Bjorklund, A. K., Forkel, M., Picelli, S., Konya, V., Theorell, J., Friberg, D., Sandberg, R., and Mjosberg, J. (2016). The heterogeneity of human CD127(+) innate lymphoid cells revealed by single-cell RNA sequencing. Nat. Immunol. 17, 451-460.

Cerami, E., Gao, J., Dogrusoz, U., Gross, B. E., Sumer, S. O., Aksoy, B. A., Jacobsen, A., Byrne, C. J., Heuer, M. L., Larsson, E., et al. (2012). The cBio cancer genomics portal: an open platform for exploring multidimensional cancer genomics data. Cancer Discov. 2, 401-404.

Champiat, S., Dercle, L., Ammari, S., Massard, C., Hollebecque, A., Postel-Vinay, S., Chaput, N., Eggermont, A., Marabelle, A., Soria, J. C., et al. (2017). Hyperprogressive disease is a new pattern of progression in cancer patients treated by anti-PD-1/PD-L1. Clin. Cancer Res. 23, 1920-1928.

Charoentong, P., Finotello, F., Angelova, M., Mayer, C., Efremova, M., Rieder, D., Hackl, H., and Trajanoski, Z. (2017). Pan-cancer immunogenomic analyses reveal genotypeimmunophenotype relationships and predictors of response to checkpoint blockade. Cell Rep. 18, 248-262.

Dang, H. X., White, B. S., Foltz, S. M., Miller, C. A., Luo, J., Fields, R. C., and Maher, C. A. (2017). ClonEvol: clonal ordering and visualization in cancer sequencing. Ann. Oncol. 28, 3076-3082. Ford, D. J., and Dingwall, A. K. (2015). The cancer COMPASS: navigating the functions of MLL complexes in cancer. Cancer Genet. 208, 178-191.

Fung, K. Y., Nguyen, P. M., and Putoczki, T. (2017). The expanding role of innate lymphoid cells and their T-cell counterparts in gastrointestinal cancers. Mol. Immunol. 11, 1-9.

Galdiero, M. R., Bonavita, E., Barajon, I., Garlanda, C., Mantovani, A., and Jaillon, S. (2013). Tumor associated macrophages and neutrophils in cancer. Immunobiology 218, 1402-1410.

Gao, J., Aksoy, B. A., Dogrusoz, U., Dresdner, G., Gross, B., Sumer, S. O., Sun, Y., Jacobsen, A., Sinha, R., Larsson, E., et al. (2013). Integrative analysis of complex cancer genomics and clinical profiles using the cBioPortal. Sci. Signal. 6, pl 1.

Goncharova, E., Goncharov, D., Noonan, D., and Krymskaya, V. P. (2004). TSC2 modulates actin cytoskeleton and focal adhesion through TSC1-binding domain and the Rac1 GTPase. J. Cell Biol. 167, 1171-1182.

Goncharova, E. A., Goncharov, D. A., Lim, P. N., Noonan, D., and Krymskaya, V. P. (2006). Modulation of cell migration and invasiveness by tumor suppressor TSC2 in lymphangioleiomyomatosis. Am. J. Respir. Cell Mol. Biol. 34, 473-480.

Gong, J., Wang, C., Lee, P. P., Chu, P., and Fakih, M. (2017). Response to PD-1 blockade in microsatellite stable metastatic colorectal cancer harboring a POLE mutation. J. Natl. Compr. Canc Netw. 15, 142-147.

Gossage, L., Eisen, T., and Maher, E. R. (2015). VHL, the story of a tumour suppressor gene. Nat. Rev. Cancer 15, 55-64.

Hanna, G. J., Lizotte, P., Cavanaugh, M., Kuo, F. C., Shivdasani, P., Frieden, A., Chau, N. G., Schoenfeld, J. D., Lorch, J. H., Uppaluri, R., et al. (2018). Frameshift events predict anti-PD-1/L1 response in head and neck cancer. JCI Insight 3, 1-13.

Hanzelmann, S., Castelo, R., and Guinney, J. (2013). GSVA: gene set variation analysis for microarray and RNA-seq data. BMC Bioinformatics 14, 7.

Hepworth, M. R., Fung, T. C., Masur, S. H., Kelsen, J. R., McConnell, F. M., Dubrot, J., Withers, D. R., Hugues, S., Farrar, M. A., Reith, W., et al. (2015). Immune tolerance. Group 3 innate lymphoid cells mediate intestinal selection of commensal bacteria-specific CD4(+) T cells. Science 348, 1031-1035.

Hugo, W., Zaretsky, J. M., Sun, L., Song, C., Moreno, B. H., Hu-Lieskovan, S., Berent-Maoz, B., Pang, J., Chmielowski, B., Cherry, G., et al. (2016). Genomic and transcriptomic features of response to anti-PD-1 therapy in metastatic melanoma. Cell 165, 35-44.

Irshad, S., Flores-Borja, F., Lawler, K., Monypenny, J., Evans, R., Male, V., Gordon, P., Cheung, A., Gazinska, P., Noor, F., et al. (2017). RORgammat(+) innate lymphoid cells promote lymph node metastasis of breast cancers. Cancer Res. 77, 1083-1096.

Kammerer-Jacquet, S. F., Crouzet, L., Brunot, A., Dagher, J., Pladys, A., Edeline, J., Laguerre, B., Peyronnet, B., Mathieu, R., Verhoest, G., et al. (2017). Independent association of PD-L1 expression with noninactivated VHL clear cell renal cell carcinoma-A finding with therapeutic potential. Int. J. Cancer 140, 142-148.

Kato, S., Goodman, A., Walavalkar, V., Barkauskas, D. A., Sharabi, A., and Kurzrock, R. (2017). Hyperprogressors after immunotherapy: analysis of genomic alterations associated with accelerated growth rate. Clin. Cancer Res. 23, 4242-4250.

Kirchberger, S., Royston, D. J., Boulard, O., Thornton, E., Franchini, F., Szabady, R. L., Harrison, O., and Powrie, F. (2013). Innate lymphoid cells sustain colon cancer through production of interleukin-22 in a mouse model. J. Exp. Med. 210, 917-931.

Koyama, S., Akbay, E. A., L1, Y. Y., Herter-Sprie, G. S., Buczkowski, K. A., Richards, W. G., Gandhi, L., Redig, A. J., Rodig, S. J., Asahina, H., et al. (2016). Adaptive resistance to therapeutic PD-1 blockade is associated with upregulation of alternative immune checkpoints. Nat. Commun. 7, 10501.

Lazar-Molnar, E., Chen, B., Sweeney, K. A., Wang, E. J., Liu, W., Lin, J., Porcelli, S. A., Almo, S. C., Nathenson, S. G., and Jacobs, W. R., Jr. (2010). Programmed death-1 (PD-1)-deficient mice are extraordinarily sensitive to tuberculosis. Proc. Natl. Acad. Sci. USA 107, 13402-13407.

Lee, J., Kim, D. H., Lee, S., Yang, Q. H., Lee, D. K., Lee, S. K., Roeder, R. G., and Lee, J. W. (2009). A tumor suppressive coactivator complex of p53 containing ASC-2 and histone H3-lysine-4 methyltransferase MLL3 or its paralogue MLL4. Proc. Natl. Acad. Sci. USA 106, 8513-8518.

Liberzon, A., Birger, C., Thorvaldsdottir, H., Ghandi, M., Mesirov, J. P., and Tamayo, P. (2015). The molecular signatures database (MSigDB) hallmark gene set collection. Cell Syst. 1, 417-425.

Liberzon, A., Subramanian, A., Pinchback, R., Thorvaldsdottir, H., Tamayo, P., and Mesirov, J. P. (2011). Molecular signatures database (MSigDB) 3.0. Bioinformatics 27, 1739-1740.

Mariathasan, S., Turley, S. J., Nickles, D., Castiglioni, A., Yuen, K., Wang, Y., Kadel, E. E., III, Koeppen, H., Astarita, J. L., Cubas, R., et al. (2018). TGFbeta attenuates tumour response to PD-L1 blockade by contributing to exclusion of T cells. Nature 554, 544-548.

Menon, S., Dibble, C. C., Talbott, G., Hoxhaj, G., Valvezan, A. J., Takahashi, H., Cantley, L. C., and Manning, B. D. (2014). Spatial control of the TSC complex integrates insulin and nutrient regulation of mTORC1 at the lysosome. Cell 156, 771-785.

Miao, D., Margolis, C. A., Gao, W., Voss, M. H., L1, W., Martini, D. J., Norton, C., Bosse, D., Wankowicz, S. M., Cullen, D., et al. (2018). Genomic correlates of response to immune checkpoint therapies in clear cell renal cell carcinoma. Science 359, 801-806. 276 iScience 9, 258-277, Nov. 30, 2018

Mishalian, I., Bayuh, R., Levy, L., Zolotarov, L., Michaeli, J., and Fridlender, Z. G. (2013). Tumorassociated neutrophils (TAN) develop protumorigenic properties during tumor progression. Cancer Immunol. Immunother. 62, 1745-1756.

Niknafs, N., Kim, D., Kim, R., Diekhans, M., Ryan, M., Stenson, P. D., Cooper, D. N., and Karchin, R. (2013). MuPIT interactive: webserver for mapping variant positions to annotated, interactive 3D structures. Hum. Genet. 132, 1235-1243.

Rabello, D. D. A., Ferreira, V., Berzoti-Coelho, M. G., Burin, S. M., Magro, C. L., Cacemiro, M. D. C., Simoes, B. P., Saldanha-Araujo, F., de Castro, F. A., and Pittella-Silva, F. (2018). MLL2/KMT2D and MLL3/KMT2C expression correlates with disease progression and response to imatinib mesylate in chronic myeloid leukemia. Cancer Cell Int. 18, 26.

Riaz, N., Havel, J. J., Makarov, V., Desrichard, A., Urba, W. J., Sims, J. S., Hodi, F. S., Martin-Algarra, S., Mandal, R., Sharfman, W. H., et al. (2017). Tumor and microenvironment evolution during immunotherapy with Nivolumab. Cell 171, 934-949.e15.

Rizvi, N. A., Hellmann, M. D., Snyder, A., Kvistborg, P., Makarov, V., Havel, J. J., Lee, W., Yuan, J., Wong, P., Ho, T. S., et al. (2015). Cancer immunology. Mutational landscape determines sensitivity to PD-1 blockade in non-small cell lung cancer. Science 348, 124-128.

Saada-Bouzid, E., Defaucheux, C., Karabajakian, A., Coloma, V. P., Servois, V., Paoletti, X., Even, C., Fayette, J., Guigay, J., Loirat, D., et al. (2017). Hyperprogression during anti-PD-1/PD-L1 therapy in patients with recurrent and/or metastatic head and neck squamous cell carcinoma. Ann. Oncol. 28, 1605-1611.

Sagiv, J. Y., Michaeli, J., Assi, S., Mishalian, I., Kisos, H., Levy, L., Damti, P., Lumbroso, D., Polyansky, L., Sionov, R. V., et al. (2015). Phenotypic diversity and plasticity in circulating neutrophil subpopulations in cancer. Cell Rep. 10, 562-573.

Sharma, P., and Allison, J. P. (2015). Immune checkpoint targeting in cancer therapy: toward combination strategies with curative potential. Cell 161, 205-214.

Sharma, P., Hu-Lieskovan, S., Wargo, J. A., and Ribas, A. (2017). Primary, adaptive, and acquired resistance to cancer immunotherapy. Cell 168, 707-723.

Spits, H., Artis, D., Colonna, M., Diefenbach, A., Di Santo, J. P., Eberl, G., Koyasu, S., Locksley, R. M., McKenzie, A. N., Mebius, R. E., et al. (2013). Innate lymphoid cells—a proposal for uniform nomenclature. Nat. Rev. Immunol. 13, 145-149.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc. NatL. Acad. Sci. USA 102, 15545-15550.

Tauriello, D. V. F., Palomo-Ponce, S., Stork, D., Berenguer-Llergo, A., Badia-Ramentol, J., Iglesias, M., Sevillano, M., Ibiza, S., Canellas, A., Hernando-Momblona, X., et al. (2018). TGFbeta drives immune evasion in genetically reconstituted colon cancer metastasis. Nature 554, 538-543.

Teo, M. Y., Seier, K., Ostrovnaya, I., Regazzi, A. M., Kania, B. E., Moran, M. M., Cipolla, C. K., Bluth, M. J., Chaim, J., A I-Ahmadie, H., et al. (2018). Alterations in DNA damage response and repair genes as potential marker of clinical benefit from PD-1/PD-L1 blockade in advanced urothelial cancers. J. Clin. Oncol. 36, 1685-1694.

Topalian, S. L., Drake, C. G., and Pardoll, D. M. (2012). Targeting the PD-1/B7-H1(PD-L1) pathway to activate anti-tumor immunity. Curr. Opin. Immunol. 24, 207-212.

Tuting, T., and de Visser, K. E. (2016). CANCER. How neutrophils promote metastasis. Science 352, 145-146.

van Beek, J. J. P., Martens, A. W. J., Bakdash, G., and de Vries, I J. M. (2016). Innate lymphoid cells in tumor immunity. Biomedicines 4, 7-21.

Wallrapp, A., Riesenfeld, S. J., Burkett, P. R., Abdulnour, R. E., Nyman, J., Dionne, D., Hofree, M., Cuoco, M. S., Rodman, C., Farouq, D., et al. (2017). The neuropeptide NMU amplifies ILC2-driven allergic lung inflammation. Nature 549, 351-356.

Wartewig, T., Kurgyis, Z., Keppler, S., Pechloff, K., Hameister, E., Ollinger, R., Maresch, R., Buch, T., Steiger, K., Winter, C., et al. (2017). PD-1 is a haploinsufficient suppressor of T cell lymphomagenesis. Nature 552, 121-125.

Westin, J. R., Chu, F., Zhang, M., Fayad, L. E., Kwak, L. W., Fowler, N., Romaguera, J., Hagemeister, F., Fanale, M., Samaniego, F., et al. (2014). Safety and activity of PD1 blockade by pidilizumab in combination with rituximab in patients with relapsed follicular lymphoma: a single group, open-label, phase 2 trial. Lancet Oncol. 15, 69-77.

Yoshikawa, S., Kiyohara, Y., Otsuka, M., Kondou, R., Nonomura, C., Miyata, H., Iizuka, A., Ohshima, K., Urakami, K., Nagashima, T., et al. (2017). Multiomics profiling of patients with melanoma treated with Nivolumab in project HOPE. Anticancer Res. 37, 1321-1328.

Zaretsky, J. M., Garcia-Diaz, A., Shin, D. S., Escuin-Ordinas, H., Hugo, W., Hu-Lieskovan, S., Torrejon, D. Y., Abril-Rodriguez, G., Sandoval, S., Barthly, L., et al.

(2016). Mutations associated with acquired resistance to PD-1 blockade in melanoma. N. Engl. J. Med. 375, 819-829.

Zhang, J., Xu, X., Shi, M., Chen, Y., Yu, D., Zhao, C., Gu, Y., Yang, B., Guo, S., Ding, G., et al. (2017). CD13(hi) Neutrophil-like myeloid-derived suppressor cells exert immune suppression through Arginase 1 expression in pancreatic ductal adenocarcinoma. Oncoimmunology 6, e1258504.

Zoncu, R., Efeyan, A., and Sabatini, D. M. (2011). mTOR: from growth signal integration to cancer, diabetes and ageing. Nat. Rev. Mol. Cell Biol. 12, 21-35.

SUPPLEMENTAL REFERENCES

Abdin, S. M., Zaher, D. M., Arafa, E. A., and Omar, H. A. (2018). Tackling Cancer Resistance by Immunotherapy: Updated Clinical Impact and Safety of PD-1/PD-L1 Inhibitors. Cancers (Basel) 10.

Aguirre-Gamboa, R., Gomez-Rueda, H., Martinez-Ledesma, E., Martinez-Torteya, A., Chacolla-Huaringa, R., Rodriguez-Barrientos, A., Tamez-Pena, J. G., and Trevino, V. (2013). SurvExpress: an online biomarker validation tool and database for cancer gene expression data using survival analysis. PLoS One 8, e74250.

Benson, D. M., Jr., Bakan, C. E., Mishra, A., Hofmeister, C. C., Efebera, Y., Becknell, B., Baiocchi, R. A., Zhang, J., Yu, J., Smith, M. K., et al. (2010). The PD-1/PD-L1 axis modulates the natural killer cell versus multiple myeloma effect: a therapeutic target for CT-011, a novel monoclonal anti-PD-1 antibody. Blood 116, 2286-2294.

Budczies, J., Kosztyla, D., Torne, C. V., Stenzinger, A., Darb-Esfahani, S., Dietel, M., and Denkert, C. (2014). cancerclass: An R Package for development and validation of diagnostic tests from high-dimensional molecular data. J Stat Software 59, 1-19.

Champiat, S., Dercle, L., Ammari, S., Massard, C., Hollebecque, A., Postel-Vinay, S., Chaput, N., Eggermont, A., Marabelle, A., Soria, J. C., et al. (2017). Hyperprogressive Disease Is a New Pattern of Progression in Cancer Patients Treated by Anti-PD-1/PD-L1. Clin Cancer Res 23, 1920-1928.

Charoentong, P., Finotello, F., Angelova, M., Mayer, C., Efremova, M., Rieder, D., Hackl, H., and Trajanoski, Z. (2017). Pan-cancer Immunogenomic Analyses Reveal Genotype-Immunophenotype Relationships and Predictors of Response to Checkpoint Blockade. Cell Rep 18, 248-262.

Dang, H. X., White, B. S., Foltz, S. M., Miller, C. A., Luo, J., Fields, R. C., and Maher, C. A. (2017). ClonEvol: clonal ordering and visualization in cancer sequencing. Ann Oncol 28, 3076-3082.

Fried, I., Lossos, A., Ben Ami, T., Dvir, R., Toledano, H., Ben Arush, M. W., Postovski, S., Abu Kuidar, A., Yalon, M., Weintraub, M., et al. (2018). Preliminary results of immune modulating antibody MDV9300 (pidilizumab) treatment in children with diffuse intrinsic pontine glioma. J Neurooncol 136, 189-195.

Gu, Z., Eils, R., and Schlesner, M. (2016). Complex heatmaps reveal patterns and correlations in multidimensional genomic data. Bioinformatics 32, 2847-2849.

Haas, B. J., Papanicolaou, A., Yassour, M., Grabherr, M., Blood, P. D., Bowden, J., Couger, M. B., Eccles, D., Li, B., Lieber, M., et al. (2013). De novo transcript sequence reconstruction from RNA-seq using the Trinity platform for reference generation and analysis. Nat Protoc 8, 1494-1512.

Hakimi, A. A., Reznik, E., Lee, C. H., Creighton, C. J., Brannon, A. R., Luna, A., Aksoy, B. A., Liu, E. M., Shen, R., Lee, W., et al. (2016). An Integrated Metabolic Atlas of Clear Cell Renal Cell Carcinoma. Cancer Cell 29, 104-116.

Hanley, J. A., and McNeil, B. J. (1982). The meaning and use of the area under a receiver operating characteristic (ROC) curve. Radiology 143, 29-36.

Hanzelmann, S., Castelo, R., and Guinney, J. (2013). GSVA: gene set variation analysis for microarray and RNA-seq data. BMC Bioinformatics 14, 7. Jan, B., Kosztyla, D., von Törne, C., Stenzinger, A., Darb-Esfahani, S., Dietel, M., and Denkert, C. (2014). cancerclass: An R Package for Development and Validation of Diagnostic Tests from High-Dimensional Molecular Data. 2014 59, 19.

Jelinek, T., and Hajek, R. (2016). PD-1/PD-L1 inhibitors in multiple myeloma: The present and the future. Oncoimmunology 5, e1254856.

Kato, S., Goodman, A., Walavalkar, V., Barkauskas, D. A., Sharabi, A., and Kurzrock, R. (2017). Hyperprogressors after Immunotherapy: Analysis of Genomic Alterations Associated with Accelerated Growth Rate. Clin Cancer Res 23, 4242-4250.

Koboldt, D. C., Zhang, Q., Larson, D. E., Shen, D., McLellan, M. D., Lin, L., Miller, C. A., Mardis, E. R., Ding, L., and Wilson, R. K. (2012). VarScan 2: somatic mutation and copy number alteration discovery in cancer by exome sequencing. Genome Res 22, 568-576.

Langmead, B., Trapnell, C., Pop, M., and Salzberg, S. L. (2009). Ultrafast and memory-efficient alignment of short DNA sequences to the human genome. Genome Biol 10, R25.

Li, H., and Durbin, R. (2009). Fast and accurate short read alignment with Burrows-Wheeler transform. Bioinformatics 25, 1754-1760.

Liberzon, A., Birger, C., Thorvaldsdottir, H., Ghandi, M., Mesirov, J. P., and Tamayo, P. (2015). The Molecular Signatures Database (MSigDB) hallmark gene set collection. Cell Syst 1, 417-425.

Liberzon, A., Subramanian, A., Pinchback, R., Thorvaldsdottir, H., Tamayo, P., and Mesirov, J. P. (2011). Molecular signatures database (MSigDB) 3.0. Bioinformatics 27, 1739-1740.

McKenna, A., Hanna, M., Banks, E., Sivachenko, A., Cibulskis, K., Kernytsky, A., Garimella, K., Altshuler, D., Gabriel, S., Daly, M., et al. (2010). The Genome Analysis Toolkit: a MapReduce framework for analyzing next-generation DNA sequencing data. Genome Res 20, 1297-1303.

Miller, C. A., McMichael, J., Dang, H. X., Maher, C. A., Ding, L., Ley, T. J., Mardis, E. R., and Wilson, R. K. (2016). Visualizing tumor evolution with the fishplot package for R. BMC Genomics 17, 880.

Miller, C. A., White, B. S., Dees, N. D., Griffith, M., Welch, J. S., Griffith, O. L., Vij, R., Tomasson, M. H., Graubert, T. A., Walter, M. J., et al. (2014). SciClone: inferring clonal architecture and tracking the spatial and temporal patterns of tumor evolution. PLoS Comput Biol 10, e1003665.

Mkrtichyan, M., Najjar, Y. G., Raulfs, E. C., Abdalla, M. Y., Samara, R., Rotem-Yehudar, R., Cook, L., and Khleif, S. N. (2011). Anti-PD-1 synergizes with cyclophosphamide to induce potent anti-tumor vaccine effects through novel mechanisms. Eur J Immunol 41, 2977-2986.

Niknafs, N., Kim, D., Kim, R., Diekhans, M., Ryan, M., Stenson, P. D., Cooper, D. N., and Karchin, R. (2013).

MuPIT interactive: webserver for mapping variant positions to annotated, interactive 3D structures. Hum Genet 132, 1235-1243.

Olsson, A., Venkatasubramanian, M., Chaudhri, V. K., Aronow, B. J., Salomonis, N., Singh, H., and Grimes, H. L. (2016). Single-cell analysis of mixed-lineage states leading to a binary cell fate choice. Nature 537, 698-702.

Pei, M., Niu, J., L1, C., Cao, F., and Quan, S. (2016). Identification and expression analysis of genes related to calyx persistence in Korla fragrant pear. BMC Genomics 17, 132.

Riaz, N., Havel, J. J., Makarov, V., Desrichard, A., Urba, W. J., Sims, J. S., Hodi, F. S., Martin-Algarra, S., Mandal, R., Sharfman, W. H., et al. (2017). Tumor and Microenvironment Evolution during Immunotherapy with Nivolumab. Cell 171, 934-949 e915.

Rosenblatt, J., Glotzbecker, B., Mills, H., Vasir, B., Tzachanis, D., Levine, J. D., Joyce, R. M., Wellenstein, K., Keefe, W., Schickler, M., et al. (2011). PD-1 blockade by CT-011, anti-PD-1 antibody, enhances ex vivo T-cell responses to autologous dendritic cell/myeloma fusion vaccine. J Immunother 34, 409-418.

Saada-Bouzid, E., Defaucheux, C., Karabajakian, A., Coloma, V. P., Servois, V., Paoletti, X., Even, C., Fayette, J., Guigay, J., Loirat, D., et al. (2017). Hyperprogression during anti-PD-1/PD-L1 therapy in patients with recurrent and/or metastatic head and neck squamous cell carcinoma. Ann Oncol 28, 1605-1611.

Subramanian, A., Tamayo, P., Mootha, V. K., Mukherjee, S., Ebert, B. L., Gillette, M. A., Paulovich, A., Pomeroy, S. L., Golub, T. R., Lander, E. S., et al. (2005). Gene set enrichment analysis: a knowledge-based approach for interpreting genome-wide expression profiles. Proc Natl Acad Sci USA 102, 15545-15550.

Tappeiner, E., Finotello, F., Charoentong, P., Mayer, C., Rieder, D., and Trajanoski, Z. (2017). TIminer: NGS data mining pipeline for cancer immunology and immunotherapy. Bioinformatics 33, 3140-3141.

Wang, K., L1, M., and Hakonarson, H. (2010). ANNOVAR: functional annotation of genetic variants from high-throughput sequencing data. Nucleic Acids Res 38, e164.

Wang, X., Xiong, M., Lei, C., and Zhu, F. (2015). The developmental transcriptome of the synanthropic fly Chrysomya megacephala and insights into olfactory proteins. BMC Genomics 16, 20.

Westin, J. R., Chu, F., Zhang, M., Fayad, L. E., Kwak, L. W., Fowler, N., Romaguera, J., Hagemeister, F., Fanale, M., Samaniego, F., et al. (2014). Safety and activity of PD1 blockade by pidilizumab in combination with rituximab in patients with relapsed follicular lymphoma: a single group, open-label, phase 2 trial. Lancet Oncol 15, 69-77.

Xiong, D., Wang, Y., Kupert, E., Simpson, C., Pinney, S. M., Gaba, C. R., Mandal, D., Schwartz, A. G., Yang, P., de Andrade, M., et al. (2015). A recurrent mutation in PARK2 is associated with familial lung cancer. Am J Hum Genet 96, 301-308.

Example 2: Further Validation

In Example 1, we developed a 121-gene set to differentiate hyperprogressive patients from non-progressive patients in response to immune checkpoint therapy (ICT) and verified its prognostic value in two datasets. We further validated this signature using two independent datasets. The first one is a dataset of 28 patients who received either pembrolizumab or nivolumab as the anti-PD-1 therapy for their metastatic melanoma and had sufficient high quality pre-treatment melanoma RNA samples subjected to RNA sequencing (RNA-seq)[1]. We extracted the corresponding RNA-seq dataset under accession number GSE78220, which had pre-treatment gene expression data for 13 progressive vs 15 non-progressive melanoma patients in response to anti-PD-1 therapy. Then we tested the performance of the 121-gene signature in separating progressive patients from non-progressive patients. Our previously identified 121-gene expression signature had significantly high prognostic values for predicting the ICT outcome, which had an area under curve (AUC) value of 0.91 (95% confidence interval [CI], 0.86-0.97), a sensitivity of 0.80 (95% CI, 0.56-0.94), and a specificity of 0.85 (95% CI, 0.59-0.97) in predicting progressive versus non-progressive melanoma patients in the new dataset (FIG. 54). The second dataset comprised gene expression data of 10 skin tumors from a patient with melanoma who had been treated with anti-PD-1 (Nivolumab) and available under accession number GSE79691. The microarray gene expression data were generated for 4 progressed tumors and 6 non-progressive tumors by the Illumina HumanHT-12 WG-DASL V4.0 R2 expression beadchip platform. As shown in FIG. 55, the accurate prediction of the progressive tumors versus the non-progressive tumors was achieved by using the 121-gene expression signature, which had an area under curve (AUC) value of 1.00 (95% confidence interval [CI], 1.00-1.00), a sensitivity of 1.00 (95% CI, 0.74-1.00), and a specificity of 1.00 (95% CI, 0.61-1.00).

REFERENCES

1 Hugo, W. et al. Genomic and Transcriptomic Features of Response to Anti-PD-1 Therapy in Metastatic Melanoma. *Cell* 165, 35-44 (2016).

2 Ascierto, M. L. et al. Transcriptional Mechanisms of Resistance to Anti-PD-1 Therapy. *Clin Cancer Res* 23, 3168-3180 (2017).

We claim:
1. A method comprising:
    (a) processing a tumor sample from a patient to obtain nucleic acid data, the nucleic acid data comprising RNA expression level data for a plurality of genes;
    (b) measuring the RNA expression levels of a subset of selected genes from the plurality, the selected genes consisting of AAK1, ACOT1, ACOT2, ADAR, AFF1, ANKS6, ANXA5, ARID2, ARL1, ARMC9, ATF7IP, AITP11C, ATP5L, BAZ1B, BAZ2A, C17orf97, CAMSAP1, CARD8, CCNA1, CCNT1, CD63, CD96, CHD4, CLSTN3, COL4A1, COL4A2, COMMD9, CORO1C, CPT1A, CREBZF, CSNK1G1, CTLA4, CYP2D6, DGKD, DIAPH1, EID2, ELK4, EP300, ERN1, FAHD1, FAM104B, FBXL17, FPGT, FUBP3, FUCA2, GALNT10, GALNT2, GAPVD1, GATAD2B, GBF1, GOLIM4, GPR18, HADH, HHLA3, HIVEP1, HIVEP2, HMBS, HPGDS, HSPG2, KDM6B, KDR, KLHDC8B, LAMTOR3, LGALS12, LNPEP, LRP6, MAGEH1, MEF2D, MTIF3, NFE2L2, NOTCH3, NPLOC4, NSD1, NUP188, OBSCN, OTUD7B, PAK2, PCDHGB7, PHF8, PPM1L, PPP2R3C, PTPN3, PTS, RANGAP1, SATB1, SERPINF1, SETX, SLC25A34, SLC27A1, SLC38A6, SLC6A6, SMURF1, SNAPC4, SORT1, SPEN, SPIN2A, SPP1, SSBP2, OBFC1, SYTL4, TCF4, TEX261, TGOLN2, TIMM8B, TLN1, TMEM99, TNFRSF25, TNKS2, TRIO, TRIP12, TSC2, TSPAN3, UBTF, KIAA2018, VHL, WDR44, YWHAE, YWHAQ, ZFP36L1, ZNF609, and ZNF878;

(c) measuring the difference in expression level of the subset of selected genes in (b) compared to control expression levels;

(d) based on the measuring in (c), classifying a likelihood that the patient develops hyperprogesssive disease (HPD) in response to anti-PD-1 immunotherapy.

2. The method of claim 1, further comprising:
based on the classifying in (d),
administering anti-PD-1 immunotherapy to the patient.

3. The method of claim 1, wherein the method has an accuracy of at least 85%.

4. The method of claim 1, wherein step (a) comprises performing RNA sequencing of the patient tumor sample.

5. The method of claim 1, wherein the members of the subset are selected based on the tumor type.

6. The method of claim 5 wherein the patient tumor type is selected from the group consisting of bladder carcinoma, breast invasive carcinoma, colon adenocarcinoma, esophageal carcinoma, head and neck squamous cell carcinoma, kidney renal clear cell carcinoma, brain lower grade glioma, liver hepatocellular carcinoma, lung adenocarcinoma, lung squamous cell carcinoma, pancreatic adenocarcinoma, skin cutaneous melanoma, and stomach adenocarcinoma.

7. The method claim 1, wherein nucleic acid data comprises sequencing data, and wherein step (c) additionally comprises identifying a copy number variation or a variant in a nucleotide sequence of one or more members of the selected subset.

8. The method of claim 1, wherein control expression levels comprise a first dataset comprising combined tumor expression data of known HPD patients prior to therapy and a second dataset comprising combined tumor expression data of known non-HPD patients prior to therapy.

9. The method of claim 8 wherein control expression levels further comprise expression data of a normal tissue sample.

10. The method of claim 1, wherein the method has a sensitivity of at least 70%.

11. The method of claim 1, wherein the method has a specificity of at least about 90%.

12. The method of claim 1, wherein said patient tumor sample comprises melanoma tissue from a patient that developed hyperprogressive disease (HPD), and wherein the classifying in step (d) indicates the patient as likely to develop HPD.

13. The method of claim 1, wherein said patient tumor sample comprises melanoma tissue from a patient treated with anti-PD therapy that did not develop HPD, and wherein the classifying in step (d) indicates the patient as not likely to develop HPD.

14. A system for processing a patient tumor sample comprising:

(a) a computer capable of receiving input data comprising RNA expression levels of a plurality of biomarkers, (b) a classifier trained to
  (i) select a subset of the RNA expression level data from a group of biomarkers consisting of AAK1, ACOT1, ACOT2, ADAR, AFF1, ANKS6, ANXA5, ARID2, ARL1, ARMC9, ATF7IP, ATP11C, ATP5L, BAZ1B, BAZ2A, C17orf97, CAMSAP1, CARD8, CCNA1, CCNT1, CD63, CD96, CHD4, CLSTN3, COL4A1, COL4A2, COMMD9, CORO1C, CPT1A, CREBZF, CSNK1G1, CTLA4, CYP2D6, DGKD, DIAPH1, EID2, ELK4, EP300, ERN1, FAHD1, FAM104B, FBXL17, FPGT, FUBP3, FUCA2, GALNT10, GALNT2, GAPVD1, GATAD2B, GBF1, GOLIM4, GPR18, HADH, HHLA3, HIVEP1, HIVEP2, HMBS, HPGDS, HSPG2, KDM6B, KDR, KLHDC8B, LAMTOR3, LGALS12, LNPEP, LRP6, MAGEH1, MEF2D, MTIF3, NFE2L2, NOTCH3, NPLOC4, NSD1, NUP188, OBSCN, OTUD7B, PAK2, PCDHGB7, PHF8, PPM1L, PPP2R3C, PTPN3, PTS, RANGAP1, SATB1, SERPINF1, SETX, SLC25A34, SLC27A1, SLC38A6, SLC6A6, SMURF1, SNAPC4, SORT1, SPEN, SPIN2A, SPP1, SSBP2, OBFC1, SYTL4, TCF4, TEX261, TGOLN2, TIMM8B, TLN1, TMEM99, TNFRSF25, TNKS2, TRIO, TRIP12, TSC2, TSPAN3, UBTF, KIAA2018, VHL, WDR44, YWHAE, YWHAQ, ZFP36L1, ZNF609, and ZNF878;
  (ii) measure RNA expression levels of the selected subset of biomarkers;
  (iii) measure the difference between the RNA expression levels of the selected subset of biomarkers and control RNA expression levels;
  (iv) based on the measurements of (ii) and (iii) classifying the patient tumor sample with a likelihood that the patient develops hyperprogesssive disease (HPD) in response to anti-PD-1 immunotherapy;

(c) an output report from the classifier that identifies said classification as indicative of the likelihood that the patient develops hyperprogesssive disease in response to anti-PD-1 immunotherapy.

* * * * *

UNITED STATES PATENT AND TRADEMARK OFFICE
CERTIFICATE OF CORRECTION

PATENT NO. : 12,380,963 B2
APPLICATION NO. : 17/070668
DATED : August 5, 2025
INVENTOR(S) : Donghai Xiong et al.

It is certified that error appears in the above-identified patent and that said Letters Patent is hereby corrected as shown below:

In the Specification

Column 4, Line 9, "(95%" should be --[95%--.

Column 11, Line 58, "(a)" should be --(β)--.

Column 12, Line 28, "X" should be --λ--.

Column 26, Line 23, "TGF-3" should be --TGF-β--.

Columns 29-30, TABLE 2, Line 2, "Deleterions Somatic Mutatations" should be --Deleterious Somatic Mutations--.

Columns 29-30, TABLE 2, Line 44, "mutaton" should be --mutation--.

Column 32, Line 6, "(y6)" should be --(γδ)--.

Column 40, Line 15, "TGF-3" should be --TGF-β--.

Column 40, Line 30, "β2M" should be --B2M--.

Columns 43-44, TABLE 5, Line 12, "Pt'" should be --Pt1--.

Column 50, Line 45, "(L1" should be --(Li--.

Column 50, Line 47, "(L1" should be --(Li--.

Column 56, Line 56, "L1" should be --Li--.

Signed and Sealed this
Fourteenth Day of October, 2025

John A. Squires
*Director of the United States Patent and Trademark Office*

Column 58, Line 30, "A I-Ahmadie" should be --Al-Ahmadie--.

Column 59, Line 26, "Hofrneister" should be --Hofmeister--.

Column 59, Line 63, "L1" should be --Li--.

Column 61, Line 8, "L1" should be --Li--.

Column 61, Line 39, "L1" should be --Li--.

In the Claims

Claim 1, Column 62, Line 48, "AITP11C" should be --ATP11C--.